US008945855B2

(12) United States Patent
Iverson et al.

(10) Patent No.: US 8,945,855 B2
(45) Date of Patent: Feb. 3, 2015

(54) METHOD FOR ENGINEERING PROTEASES AND PROTEIN KINASES

(71) Applicant: Research Development Foundation, Carson City, NV (US)

(72) Inventors: Brent L. Iverson, Austin, TX (US); George Georgiou, Austin, TX (US); Joseph M. Taft, Austin, TX (US); Li Yi, Austin, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 13/926,749

(22) Filed: Jun. 25, 2013

(65) Prior Publication Data
US 2014/0017764 A1   Jan. 16, 2014

Related U.S. Application Data

(60) Provisional application No. 61/663,685, filed on Jun. 25, 2012, provisional application No. 61/720,461, filed on Oct. 31, 2012, provisional application No. 61/731,196, filed on Nov. 29, 2012.

(51) Int. Cl.
*C12N 15/81* (2006.01)
*C12N 9/12* (2006.01)
*C12N 9/50* (2006.01)
*C12N 15/10* (2006.01)

(52) U.S. Cl.
CPC .............. *C12N 9/50* (2013.01); *C12N 15/1037* (2013.01); *C12N 15/1058* (2013.01); *C12N 15/81* (2013.01); *C12N 9/12* (2013.01)
USPC ......... 435/7.1; 435/194; 435/219; 435/254.2; 435/320.1

(58) Field of Classification Search
CPC .................................. C12N 15/81; C12N 9/12
USPC ...................... 435/7.1, 194, 219, 254.2, 320.1
See application file for complete search history.

(56) References Cited

U.S. PATENT DOCUMENTS

2006/0029947 A1   2/2006  Georgiou et al.
2010/0075326 A1*  3/2010  Jin et al. .............................. 435/6

OTHER PUBLICATIONS

Aharoni et al., "High-Throughput Screening of Enzyme Libraries: Thiolactonases Evolved by Fluroescence-Activated Sorting of Single Cells in Emulsion Compartments," *Chem. Biol.*, 12(12):1281-1289, 2005.
Benatuil et al., "An improved yeast transformation method for the generation of very large human antibody libraries," *Protein Eng. Des. Sel.*, 23(4):155-159, 2010.
Boder, et al., "Yeast surface display for screening combinatorial polypeptide libraries," *Nature Biotechnology*, 15:553-557, 1997.
Chanalia et al., "Applications of microbial proteases in pharmaceutical industry: an overview," *Rev. Med. Microbiol.*, 22(4):96-101, 2011.
Chao et al., "Isolating and engineering human antibodies using yeast surface display," *Nat. Protoc.*, 1(2):755-768, 2006.
Chen, et al., "A general strategy for the evolution of bond-forming enzymes using yeast display," *Proc. Natl. Acad. Sci., USA*, 108(28):11399-11404, 2011.
Collen and Lijnen, "Basic and Clinical Aspects of Fibrinolysis and Thrombolysis," *Blood*, 78(12):3114-3124, 1991.
Copic et al., "Genomewide Analysis Reveals Novel Pathways Affecting Endoplasmic Reticulum Homeostasis, Protein Modification and Quality Control," *Genetics*, 182:757-769, 2009.
Craik, et al., "Proteases as therapeutics," *Biochem. J.*, 435:1-16, 2011.
Drag and Salvesen, "Emerging principles in protease-based drug discovery," *Nat. Rev. Drug Discov.*, 9(9):690-701, 2010.
Drummond et al., "Why High-error-rate Random Mutagenesis Libraries are Enriched in Functional and Improved Proteins," *J. Mol. Biol.*, 350(4):806-816, 2005.
Gould and Tawfik, "Directed Evolution of the Promiscuous Esterase Activity of Carbonic Anhydrase II," *Biochemistry*, 44(14):5444-5452, 2005.
Gray et al., "Activation of Specific Apoptotic Caspases with an Engineered Small-Molecule-Activated Protease," *Cell*, 142(4):637-646, 2010.
Gupta et al., "Bacterial alkaline proteases: molecular approaches and industrial applications," *Appl. Microbiol. Biotechnol.*, 59(1):15-32, 2002.
Hedstrom, "Serine Protease Mechanism and Specificity," *Chem. Rev.*, 102(12):4501-4524, 2002.
Hedstrom, et al., "Converting trypsin to chymotrypsin: the role of surface loops," *Science*, 255(5049):1249-1253, 1992.
Hegde and Keenan, "Tail-anchored membrane protein insertion into the endoplasmic reticulum," *Nat Rev Mol Cell Biol.*, 12(12):787-98, 2011.
Jung et al., "Aglycosylated IgG variants expressed in bacteria that selectively bind FcγRI potentiate tumor cell killing by monocyte-dendritic cells," *Proc. Natl. Acad. Sci. U. S. A.*, 107:604-609, 2010.
Kapust et al., "The P1' specificity of tobascco etch virus protease," *Biochem. Biophys. Res. Commun.*, 294(5):949-955, 2002.
Kim et al., "In Vivo Determination of Substrate Specificity of Hepatitis C Virus NS3 Protease: Genetic Assay for Site-Specific Proteolysis," *Anal. Biochem.*, 284(1):42-48, 2000.
Lim et al., "Swapping the Substrate Specificities of the Neuropeptidases Neurolysin and Thimet Oligopeptidase," *J. Biol. Chem.*, 282(13):9722-9732, 2007.
Mohanty et al., "Inhibition of tobacco etch virus protease activity by detergents," *Protein Expr. Purif.*, 27:109-114, 2003.

(Continued)

*Primary Examiner* — Karen Cochrane Carlson
(74) *Attorney, Agent, or Firm* — Parker Highlander PLLC

(57) ABSTRACT

Provided are methods for protein engineering, such as engineering proteases or kinases. The methods may utilize yeast display and/or ER sequestration of proteins or substrates. In some aspects, TEV proteases with altered substrate specificity, potency, and/or efficiency are provided.

84 Claims, 23 Drawing Sheets

(56) References Cited

OTHER PUBLICATIONS

Nallamsetty et al., "Efficient site-specific process of fusion proteins by tobacco vein mottling virus protease in vivo and in vitro," *Protein Expr. Purif.*, 38(1):108-15, 2004.

O'Loughlin et al., "Diversification and Specialization of HIV Protease Function During in Vitro Evolution," *Mol. Biol. Evol.*, 23(4):764-772, 2006.

Park and Rapoport, "Mechanisms of Sec61/SecY—Mediated Protein Translocation Acorss Membranes," *Annu Rev Biophys.*, 41:21-40, 2012.

PCT International Search Report and Written Opinion issued in International Application No. PCT/US2013/047663, mailed Dec. 10, 2013.

PCT Invitation to Pay Additional Fees issued in International Application No. PCT/US2013/047663, mailed Sep. 25, 2013.

Pelham, et al., "Sorting of soluble ER proteins in yeast," *EMBO Journal*, 7(6):1757-1762, 1988.

Phan et al., "Structural Basis for the Substrate Specificity of Tobacco Etch Virus Protease," *J. Biol. Chem.*, 277(52):50564-50572, 2002.

Pogson, et al., "Engineering next generation proteases," *Curr. Opin. Biotechnol.*, 20:390-397, 2009.

Rapoport, "Protein translocation across the eukaryotic endoplasmic reticulum and bacterial plasma membranes," *Nature*, 450(7170):663-9, 2007.

Schechter and Berger, "On the size of the active site in proteases. I. Papain," *Biochem. Biophys. Res. Commun.*, 27(2):157-162, 1967.

Sellamuthu et al., "An Engineered Viral Protease Exhibiting Substrate Specificity for a Polyglutamine Stretch Prevents Polyglutamine-Induced Neuronal Cell Death," *PloS One*, 6(7):e22554, 2011.

Sellamuthu et al., "Engineering of protease variants exhibiting altered substrate specificity," *Biochem. Biophys. Res. Commun.*, 371(1):122-126, 2008.

Semenza, et al., "ERD2, a yeast gene required for the receptor-mediated retrieval of luminal ER proteins from the secretory pathway," *Cell*, 61(7):1349-1357, 1990.

Small et al., "Predotar: A tool for rapidly screening proteomes for N-terminal targeting sequences," *Proteomics*, 4(6):1581-90, 2004.

Teasdale and Jackson, "Signal-Mediated Sorting of Membrane Proteins Between the Endoplasmic Reticulum and the Golgi Apparatus," *Cell Dev. Biol.* 12, 27-54, 1996.

Varadarajan et al., "Construction and flow cytometric screening of targeted enzyme libraries," *Nat. Protoc.*, 4(6):893-901, 2009.

Varadarajan, et al., "An Engineered Protease that Cleaves Specifically after Sulfated Tyrosine," *Angew. Chemie., Int. Ed.*, 47(41):7861-7863, 2008.

Varadarajan, et al., "Engineering of protease variants exhibiting high catalytic activity and exquisite substrate selectivity," *Proc. Natl. Acad. Sci.*, 102(19):6855-6860, 2005.

Varadarajan, et al., "Highly active and selective endopeptidases with programmed substrate specificities," *Nature Chemical Biology*, 4(5):290-294, 2008.

Varadarajan, et al., "Proteases that can distinguish among different post-translational forms of tyrosine engineering using multicolor flow cytometry," *J. Am. Chem. Soc.*, 131(50):18186-18190, 2009.

Villa et al., "Crtical Amino Acids in the Active Site of Meprin Metalloproteinases for Substrate and Peptide Bond Specificity," *J. Biol. Chem.*, 278(43):42545-42550, 2003.

Waugh, "An overview of enzymatic reagents for the removal of affinity tags," *Protein Expr. Purif.*, 80:283-293, 2011.

Waugh, "TEV Protease FAQ," Last Updated Sep. 2010, Macromolecular Crystallography Laboratory, National Cancer Institute, Accessed at: http://mcll.ncifcrf.gov/waugh_tech/faq/tev.pdf.

Wehr et al. "Monitoring regulated protein-protein interactions using split TEV," *Nat. Methods*, 3(12):985-993, 2006.

Yi, et al., "Engineering of TEV protease variants by yeast ER sequestration screening (YESS) of combinatorial libraries + Supporting Information," *Proc. Natl. Acad. Sci.*, 110(18):7229-7234(+ 12 pages of Supporting Information), 2013.

\* cited by examiner

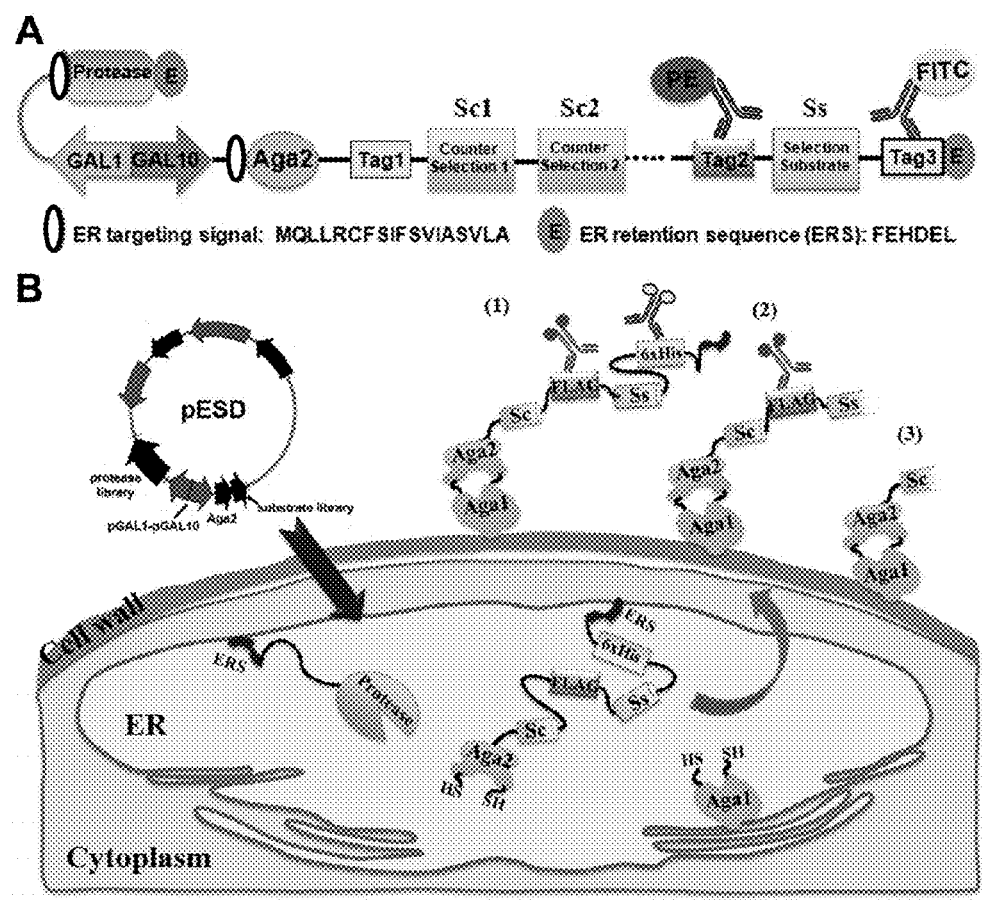
FIGS. 1A-B

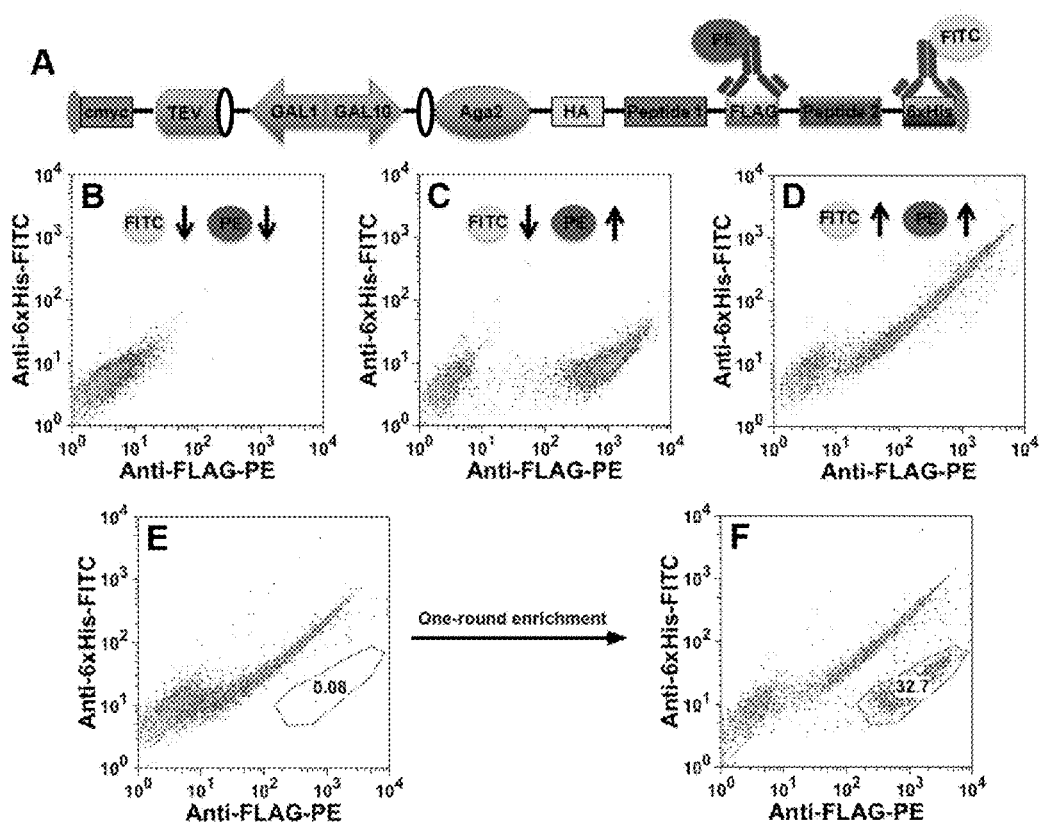
FIGS. 2A-F

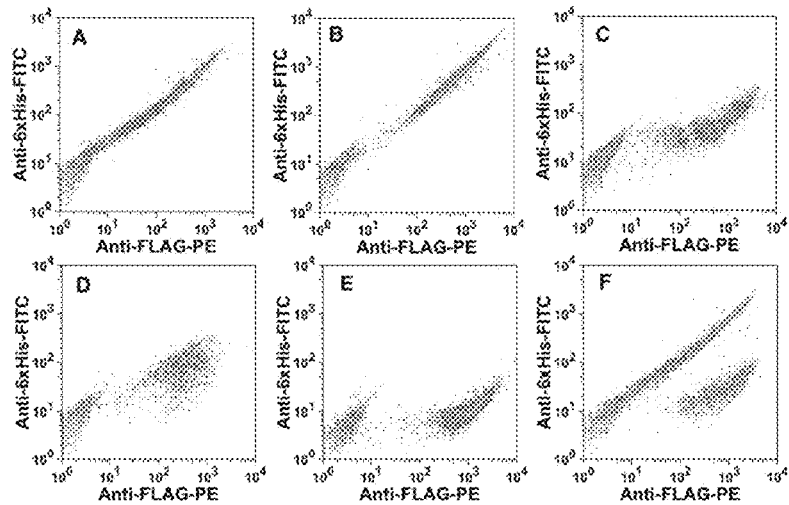
G  Vector Maps
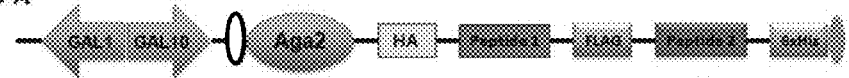
FIGS. 7A-G

A
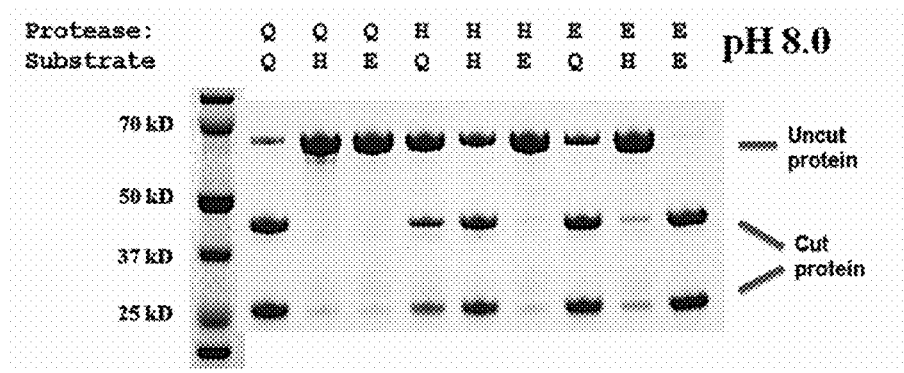
B
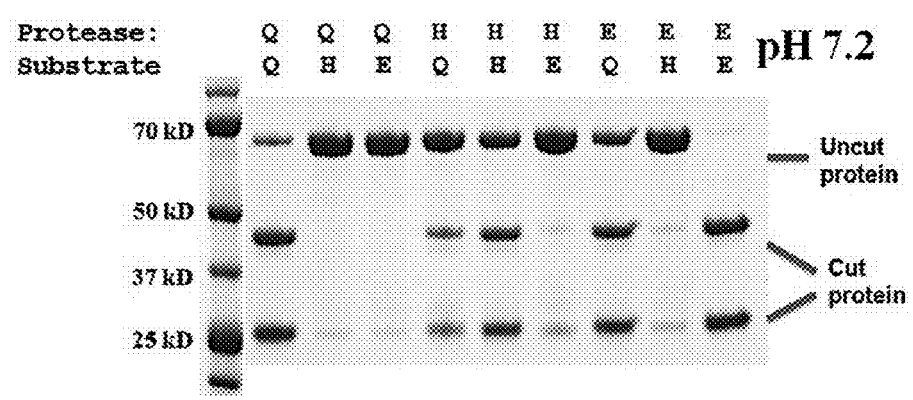
C
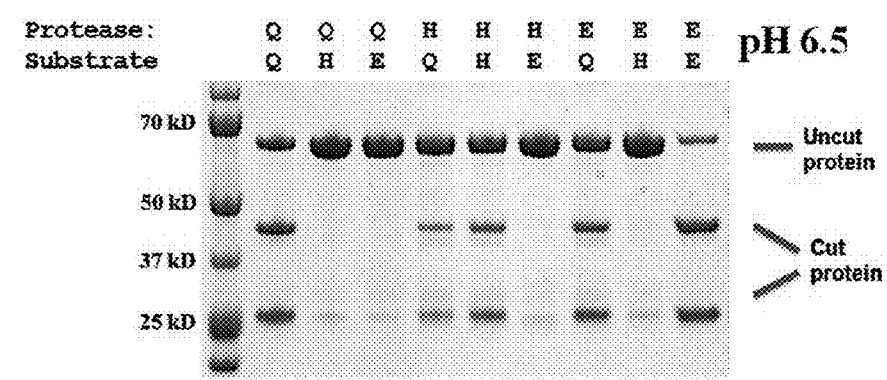
FIGS. 15A-C

Table of pESD Constructs

| Construct | E1 | TEV | Pep 1 | Pep 2 | E2 | Cutting position | PE | FITC |
|---|---|---|---|---|---|---|---|---|
| pESD-A | ✗ | ✗ | Pep A | Pep B | ✔ | Pep 2 | ↑↑ | ↑↑ |
| pESD-B | ✗ | ✔ | Pep A | Pep B | ✗ | Pep 2 | ↑↑ | ↑↑ |
| pESD-C | ✗ | ✔ | Pep A | Pep B | ✔ | Pep 2 | ↑↑ | ↓ |
| pESD-D | ✔ | ✔ | Pep A | Pep B | ✗ | Pep 2 | ↑↑ | ↑ |
| pESD-E | ✔ | ✔ | Pep A | Pep B | ✔ | Pep 2 | ↑↑ | ↓↓ |
| pESD-F | ✔ | ✔ | Pep B | Pep C | ✔ | Pep 1 | ↓↓ | ↓↓ |
| pESD-G | ✔ | ✔ | Pep C | Pep B | ✔ | Pep 2 | ↑↑ | ↓↓ |
| pESD-H | ✔ | ✔ | Pep A | Pep C | ✔ | None | ↑↑ | ↑↑ |

SEQUENCE LISTING

```
<160> NUMBER OF SEQ ID NOS: 53

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Glu Asn Leu Tyr Phe Glu Ser
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Glu Asn Leu Tyr Phe His Ser
1               5

<210> SEQ ID NO 3
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 3

Met Gln Leu Leu Arg Cys Phe Ser Ile Phe Ser Val Ile Ala Ser Val
1               5                   10                  15

Leu Ala
```

```
<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 4

Phe Glu His Asp Glu Leu
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 5

Lys Asp Glu Leu
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 6

His Asp Glu Leu
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 7

Arg Asp Glu Leu
1

<210> SEQ ID NO 8
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 8

Thr Glu Asn Leu Tyr Phe Gln Ser Gly Thr Arg Arg Trp
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 9

Thr Glu Asn Leu Tyr Phe His Ser Gly Thr Arg Arg Trp
1               5                   10
```

```
<210> SEQ ID NO 10
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 10

Thr Glu Asn Leu Tyr Phe Glu Ser Gly Thr Arg Arg Trp
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 11

Glu Asn Leu Tyr Phe Lys Ser
1               5

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15
<211> LENGTH: 13
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (6)..(6)
<223> OTHER INFORMATION: Xaa is Gln, Glu, or His

<400> SEQUENCE: 15

Glu Asn Leu Tyr Phe Xaa Ser His His His His His His
1               5                   10

<210> SEQ ID NO 16

<400> SEQUENCE: 16

000

<210> SEQ ID NO 17
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 17
```

Asp Glu Met Glu Glu Cys Ala Ser His Leu
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 18

Glu Asn Leu Tyr Phe Gln Ser
1               5

<210> SEQ ID NO 19
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 19

Cys Gly Tyr Gly Pro Lys Lys Lys Arg Lys Val Gly Gly
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(3)
<223> OTHER INFORMATION: Xaa can be any naturally occuring amino acid
<220> FEATURE:
<221> NAME/KEY: MISC_FEATURE
<222> LOCATION: (5)..(5)
<223> OTHER INFORMATION: Xaa can be any naturally occuring amino acid
<220> FEATURE:
<221> NAME/KEY: MISC_FEATURE
<222> LOCATION: (7)..(7)
<223> OTHER INFORMATION: Xaa is Gly or Ser

<400> SEQUENCE: 20

Glu Xaa Xaa Tyr Xaa Gln Xaa
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 21

Glu Asn Leu Tyr Phe Gln Gly
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 22

Asp Tyr Lys Asp Asp Asp Asp Lys

```
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (6)..(6)
<223> OTHER INFORMATION: Xaa is any residue

<400> SEQUENCE: 23

Glu Asn Leu Tyr Phe Xaa Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 24

His His His His His His
1               5

<210> SEQ ID NO 25
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 25

Gln Leu Leu Arg Cys Phe Ser Ile Phe Ser Val Ile Ala Ser Val Leu
1               5                   10                  15

Ala

<210> SEQ ID NO 26
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 26

Lys Glu Glu Leu
1

<210> SEQ ID NO 27
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 27

Lys Lys Xaa Xaa
1

<210> SEQ ID NO 28
```

```
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 28

Val Glu Lys Pro Phe Ala Ile Ala Lys Glu
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 29

Glu Gln Lys Leu Ile Ser Glu Glu Asp Leu
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 30

Tyr Pro Tyr Asp Val Pro Asp Tyr Ala
1               5

<210> SEQ ID NO 31
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 31

Tyr Thr Asp Ile Glu Met Asn Arg Leu Gly Lys
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 32

Gln Pro Glu Leu Ala Pro Glu Asp Pro Glu Asp
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 33

Gly Lys Pro Ile Pro Asn Pro Leu Leu Gly Leu Asp Ser Thr
1               5                   10

<210> SEQ ID NO 34
<211> LENGTH: 8
```

```
<212> TYPE: PRT
<213> ORGANISM: Artificial Sequence
<220> FEATURE:
<223> OTHER INFORMATION: Synthetic Peptide

<400> SEQUENCE: 34

Asp Tyr Lys Asp Asp Asp Asp Lys
1               5

<210> SEQ ID NO 35
<211> LENGTH: 43
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t

<400> SEQUENCE: 35
ggaagcattg gattcaanns aagnnsgggc agtgtggcag tcc            43

<210> SEQ ID NO 36
<211> LENGTH: 37
<212> TYPE: DNA
<213> ORGANISM: Artificial Sequence
<220> FEATURE:
<223> OTHER INFORMATION: Synthetic Primer

<400> SEQUENCE: 36
attagtatca actagagatg ggttcattgt tggtata                  37

<210> SEQ ID NO 37
<211> LENGTH: 36
<212> TYPE: DNA
<213> ORGANISM: Artificial Sequence
<220> FEATURE:
<223> OTHER INFORMATION: Synthetic Primer

<400> SEQUENCE: 37
atctctagtt gatactaatg gactgccaca ctgccc                   36

<210> SEQ ID NO 38
<211> LENGTH: 47
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 38
tttgtgttgg tgaaattsnn tgctgasnnt ataccaacaa tgaaccc       47

<210> SEQ ID NO 39
<211> LENGTH: 21
<212> TYPE: DNA
<213> ORGANISM: Artificial Sequence
```

-continued

```
<220> FEATURE:
<223> OTHER INFORMATION: Synthetic Primer

<400> SEQUENCE: 39
ttgaatccaa tgcttccaga a                                              21

<210> SEQ ID NO 40
<211> LENGTH: 20
<212> TYPE: DNA
<213> ORGANISM: Artificial Sequence
<220> FEATURE:
<223> OTHER INFORMATION: Synthetic Primer

<400> SEQUENCE: 40
aatttcacca acacaaacaa                                                20

<210> SEQ ID NO 41
<211> LENGTH: 37
<212> TYPE: DNA
<213> ORGANISM: Artificial Sequence
<220> FEATURE:
<223> OTHER INFORMATION: Synthetic Primer

<400> SEQUENCE: 41
taccatctgc agagcgacgg cgacgacgat tcatgag                             37

<210> SEQ ID NO 42
<211> LENGTH: 43
<212> TYPE: DNA
<213> ORGANISM: Artificial Sequence
<220> FEATURE:
<223> OTHER INFORMATION: Synthetic Primer

<400> SEQUENCE: 42
atggttggta ccgaaaatct ttattttagc ggtcatcatc atc                      43

<210> SEQ ID NO 43
<211> LENGTH: 136
<212> TYPE: DNA
<213> ORGANISM: Artificial Sequence
<220> FEATURE:
<223> OTHER INFORMATION: Synthetic Primer

<400> SEQUENCE: 43
cgtcaaggag aaaaaacccc ggatccgtaa tacgactcac tatagggccc gggcgtcgac     60
atgcaacttt tgagatgctt cagtattttc agcgtcatcg ccagtgtgct ggccagcttg    120
tttaaggggc cgcgtg                                                   136

<210> SEQ ID NO 44
<211> LENGTH: 157
<212> TYPE: DNA
<213> ORGANISM: Artificial Sequence
<220> FEATURE:
<223> OTHER INFORMATION: Synthetic Primer

<400> SEQUENCE: 44
gtacagtggg aacaaagtcg attttgttac atctacactg ttgttatcag atctcgagcg     60
gtaccttact cattacaatt cgtcgtgttc gaaactaccc aagtcctctt cagaaataag    120
cttttgttcg gatccattca tgagttgagt cgcttcc                             157

<210> SEQ ID NO 45
<211> LENGTH: 39
<212> TYPE: DNA
```

```
<213> ORGANISM: Artificial Sequence
<220> FEATURE:
<223> OTHER INFORMATION: Synthetic Primer

<400> SEQUENCE: 45
atggctggcc cagccggcca gcttgtttaa ggggccgcg                              39

<210> SEQ ID NO 46
<211> LENGTH: 49
<212> TYPE: DNA
<213> ORGANISM: Artificial Sequence
<220> FEATURE:
<223> OTHER INFORMATION: Synthetic Primer

<400> SEQUENCE: 46
gtccatggcc cccgaggcct taattcatga gttgagtcgc ttccttaac                   49

<210> SEQ ID NO 47
<211> LENGTH: 97
<212> TYPE: DNA
<213> ORGANISM: Artificial Sequence
<220> FEATURE:
<223> OTHER INFORMATION: Synthetic Primer

<400> SEQUENCE: 47
gtacagtggg aacaaagtcg attttgttac atctacactg ttgttatcag atctcgagcg       60
gtaccttact cattaattca tgagttgagt cgcttcc                                97

<210> SEQ ID NO 48
<211> LENGTH: 106
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (60)..(61)
<223> OTHER INFORMATION: n is a, c, g, or t

<400> SEQUENCE: 48
gagctcacaa ttcgtcgtgt tcgaaactac catgatgatg atgatgatga ctgccagasn       60
ngaaatacaa attttcactg cctttatcgt cgtcatcttt ataatc                      106

<210> SEQ ID NO 49
<211> LENGTH: 43
<212> TYPE: DNA
<213> ORGANISM: Artificial Sequence
<220> FEATURE:
<223> OTHER INFORMATION: Synthetic Primer

<400> SEQUENCE: 49
cgaattcaac cctcactaaa gggcggccgc actagtatcg atg                         43

<210> SEQ ID NO 50
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 50

Glu Asn Leu Tyr Glu Ser
1               5

<210> SEQ ID NO 51
```

```
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 51

Ser Gly Thr Arg Arg Trp
1               5

<210> SEQ ID NO 52
<211> LENGTH: 234
<212> TYPE: PRT
<213> ORGANISM: Artificial Sequence
<220> FEATURE:
<223> OTHER INFORMATION: Synthetic Peptide

<400> SEQUENCE: 52

Ser Leu Phe Lys Gly Pro Arg Asp Tyr Asn Pro Ile Ser Ser Thr Ile
1               5                   10                  15

Cys His Leu Thr Asn Glu Ser Asp Gly His Thr Thr Ser Leu Tyr Gly
            20                  25                  30

Ile Gly Phe Gly Pro Phe Ile Ile Thr Asn Lys His Leu Phe Arg Arg
        35                  40                  45

Asn Asn Gly Thr Leu Leu Val Gln Ser Leu His Gly Val Phe Lys Val
    50                  55                  60

Lys Asn Thr Thr Thr Leu Gln Gln His Leu Ile Asp Gly Arg Asp Met
65                  70                  75                  80

Ile Ile Ile Arg Met Pro Lys Asp Phe Pro Pro Phe Pro Gln Lys Leu
                85                  90                  95

Lys Phe Arg Glu Pro Gln Arg Glu Glu Arg Ile Cys Leu Val Thr Thr
            100                 105                 110

Asn Phe Gln Thr Lys Ser Met Ser Ser Met Val Ser Asp Thr Ser Cys
        115                 120                 125

Thr Phe Pro Ser Ser Asp Gly Ile Phe Trp Lys His Trp Ile Gln Thr
    130                 135                 140

Lys Asp Gly Gln Cys Gly Ser Pro Leu Val Ser Thr Arg Asp Gly Phe
145                 150                 155                 160

Ile Val Gly Ile His Ser Ala Ser Asn Phe Thr Asn Thr Asn Asn Tyr
                165                 170                 175

Phe Thr Ser Val Pro Lys Asn Phe Met Glu Leu Leu Thr Asn Gln Glu
            180                 185                 190

Ala Gln Gln Trp Val Ser Gly Trp Arg Leu Asn Ala Asp Ser Val Leu
        195                 200                 205

Trp Gly Gly His Lys Val Phe Met Pro Lys Pro Glu Glu Pro Phe Gln
    210                 215                 220

Pro Val Lys Glu Ala Thr Gln Leu Met Asn
225                 230

<210> SEQ ID NO 53
<211> LENGTH: 234
<212> TYPE: PRT
<213> ORGANISM: Artificial Sequence
<220> FEATURE:
<223> OTHER INFORMATION: Synthetic Peptide

<400> SEQUENCE: 53

Ser Leu Phe Lys Gly Pro Arg Asp Tyr Asn Pro Ile Ser Ser Thr Ile
1               5                   10                  15
```

```
Cys His Leu Thr Asn Glu Ser Asp Gly His Thr Thr Ser Leu Tyr Gly
            20              25                  30

Ile Gly Phe Gly Pro Phe Ile Ile Thr Asn Lys His Leu Phe Arg Arg
        35              40              45

Asn Asn Gly Thr Leu Leu Val Gln Ser Leu His Gly Val Phe Lys Val
    50              55              60

Lys Asn Thr Thr Thr Leu Gln Gln His Leu Ile Asp Gly Arg Asp Met
65                  70              75                      80

Ile Ile Ile Arg Met Pro Lys Asp Phe Pro Pro Phe Pro Gln Lys Leu
                85              90                      95

Lys Phe Arg Glu Pro Gln Arg Glu Glu Arg Ile Cys Leu Val Thr Thr
            100             105             110

Asn Phe Gln Thr Lys Arg Met Ser Ser Met Val Ser Asp Thr Ser Cys
        115             120             125

Thr Phe Pro Ser Ser Asp Gly Ile Phe Trp Lys His Trp Ile Gln Thr
        130             135             140

Lys Arg Gly Gln Cys Gly Ser Pro Leu Val Ser Thr Arg Asp Gly Phe
145             150             155                     160

Ile Val Gly Ile His Ser Ala Ser Asn Phe Ala Asn Thr Asn Lys Tyr
            165             170             175

Phe Thr Ser Val Pro Lys Asn Phe Met Glu Leu Leu Thr Asn Gln Glu
            180             185             190

Ala Gln Gln Trp Val Ser Gly Trp Arg Leu Asn Ala Asp Ser Val Leu
            195             200             205

Trp Gly Gly His Lys Val Phe Ile Pro Lys Pro Glu Glu Pro Phe Gln
    210             215             220

Pro Val Lys Glu Ala Thr Gln Leu Met Asn
225                 230
```

METHOD FOR ENGINEERING PROTEASES AND PROTEIN KINASES

This application claims the benefit of U.S. Provisional Patent Application No. 61/731,196, filed Nov. 29, 2012, U.S. Provisional Patent Application No. 61/720,461, filed Oct. 31, 2012, and U.S. Provisional Patent Application No. 61/663,685, filed Jun. 25, 2012, the entirety of which are incorporated herein by reference.

This invention was made with government support under Grant Nos. R01 GM065551 and R01 GM073089, awarded by the National Institutes of Health. The government has certain rights in the invention.

BACKGROUND OF THE INVENTION

1. Field of the Invention

The present invention relates generally to the field of molecular biology and medicine. More particularly, it concerns therapeutic proteases and methods for engineering proteases and protein kinases.

2. Description of Related Art

More than 600 proteases have been annotated so far, constituting the largest enzyme family in the human genome (Overall and Blobel, 2007; Marnett and Craik, 2005; Schilling and Overall, 2008). Because of their unique ability to catalyze the hydrolysis of peptide bonds and thus activate or inactivate proteins, proteases have the potential to be used in a number of applications in biotechnology and medicine (Chanalia et al., 2011; Gupta et al., 2002; Craik et al., 2011). For example, on the medical intervention side, recombinant tissue plasminogen activator (rTPA) protease is commonly used to specifically activate plasminogen to plasmin and thereby prevent or reverse clotting in embolic or thrombotic stroke (Collen and Lijnen, 1991). In addition, thrombin, Factor VII, and Factor IX are approved drugs for the therapeutic modulation of thrombosis and haemostasis (Collen and Lijnen, 1991; Craik et al., 2011; Drag and Salvesen, 2010). Looking toward the future, protease therapies can be envisioned that would involve the specific hydrolysis of validated disease targets (Craik et al., 2011). Because they exhibit catalytic turnover, a therapeutic protease would promise a substantially lower required dose compared with an antibody hitting the same target, since an antibody is expected to operate in stoichiometric fashion. Additionally, proteases find numerous applications as reagents in biotechnology, ranging from analytical to preparative biochemistry (Wehr et al., 2006; Gray et al., 2010; Waugh, 2011).

The list of potential practical applications of proteases, however, is severely limited if one is constrained to the catalytic specificities found in naturally occurring proteases. What is needed, therefore, is a general approach to the engineering of protease specificity (Varadarajan et al., 2008; Gray et al., 2010) and activity. Some previous attempts at rationally redesigning proteases for altered specificity based upon swapping binding site regions between known proteases (Hedstrom et al., 1992; Lim et al., 2007; Villa et al., 2003) have been successful. However, this approach cannot be considered general because its utility is confined to known protease specificities among structurally homologous proteins. Some examples of novel protease specificities, including several reports from the inventor's lab, have been achieved using directed evolution approaches (Sellamuthu et al., 2011; Varadarajan et al., 2005; Varadarajan et al., 2008). Despite this notable progress, two substantial challenges continue to frustrate attempts to use directed evolution to engineer proteases in a more general way.

The first challenge is that multiple mutations are often required to alter protease substrate specificity, necessitating the use of large libraries and therefore a high-throughput screen, such as flow cytometry. For example, in the case of the engineered bacterial protease OmpT, changing the P1 specificity (based on the nomenclature of Schechter and Berger (1967)) required screening a library of $2 \times 10^8$ variants and resulted in improved variants with as many as nine mutations in and around the binding pocket (Varadarjan et al., 2009a). The relatively large number of required mutations makes sense because proteases generally take part in extensive interactions with several different amino acids of their substrates and each substrate amino acid binding pocket is comprised of multiple residues (Schechter and Berger, 1967; Hedstrom, 2002). In addition, changing specificity at a given position may require simultaneous mutation of several contacts and sometimes even second shell binding pocket residues.

The second challenge to engineering specificity is that directed evolution of enzyme function commonly leads to enzyme variants displaying relaxed specificity rather than truly altered specificity (Gould and Tawfik, 2005; Aharoni et al., 2005). Engineered proteases with relaxed specificity may not be suitable for applications involving complex systems or mixtures in which the non-specific activity could have deleterious effects, including in vivo medical applications. To solve this problem, Varadarajan and coworkers demonstrated a simultaneous selection and counter selection strategy for protease activity that resulted in protease variants capable of reacting with new substrates, while maintaining a relatively narrow overall substrate specificity (Varadarjan et al., 2005). Their screening method, however, requires display of the protease on the surface of E. coli, thus limiting the method to proteases that can be expressed in E. coli, transported to the surface, and are active in the extracellular environment. Clearly, there is a need for new methods for engineering proteases.

SUMMARY OF THE INVENTION

The present invention overcomes limitations in the prior art by providing, in various aspects, methods for engineering proteases or protein kinases having an altered substrate specificity, activity, and/or potency. These methods may be used in a variety of applications ranging from biomedical research to disease therapy. In some aspects, the methods involve targeted interaction of a protease variant with a substrate in the endoplasmic reticulum (ER) of eukaryotic cells such as, e.g., yeast. The methods may involve screening a library of proteases against a library of substrates. In various aspects, engineered therapeutic proteases are provided.

As described in the below examples, a yeast cell-based high-throughput screening method is provided that can efficiently identify evolved proteases or protein kinases having altered substrate specificity or potency, and yeast cells displaying desirable protease or kinase variants can be separated, e.g., using fluorescence activated cell sorting (FACS). The method generally involves the targeted interaction of the protease or kinase variant with substrates in the yeast endoplasmic reticulum (ER). Following reaction with protease or kinase in the ER, substrate cleavage or phosphorylation products are directed to the yeast surface then detected with labeled antibodies. This method is demonstrated in the examples below by altering the P1 substrate specificity of the TEV protease. In particular, two engineered TEV proteases were isolated that recognize and cleave ENLYFES (SEQ ID NO:1) and ENLYFHS (SEQ ID NO:2) substrates, exhibiting 5000-fold and 1100-fold increases in activity with these substrates, respectively, compared to the wild-type TEV protease.

An aspect of the present invention relates to a nucleic acid vector, wherein the nucleic acid encodes: (i) a first endoplasmic reticulum (ER) targeting sequence and a first endoplasmic reticulum (ER) retention sequence; (ii) a surface expression sequence; (iii) a first peptide sequence; (iv) a first epitope tag sequence; (v) a second peptide sequence; (vi) a second epitope tag sequence; (vii) an enzyme, wherein the enzyme is a protease or a kinase; and (viii) a second endoplasmic reticulum (ER) targeting sequence and a second endoplasmic reticulum (ER) retention sequence; wherein (i), (ii), (iii), (iv), (v), and (vi) are expressed as a first fusion construct, wherein the first endoplasmic reticulum targeting sequence is located at or near the N-terminus of the first fusion construct and wherein the first endoplasmic reticulum retention sequence is located at or near the C-terminus of the first fusion construct; and wherein (vii) and (viii) are expressed as a second fusion construct, wherein the second endoplasmic reticulum targeting sequence is located at or near the N-terminus of the second fusion construct, and wherein the second endoplasmic reticulum retention sequence is located at or near the C-terminus of the second fusion construct. In some embodiments, the enzyme is a sortase or a glycosyltransferase. In some embodiments, (i), (ii), (iii), (iv), (v), and (vi) are operably linked to a first promoter, and (vii) and (viii) may be operably linked to a second promoter. The first peptide sequence may be a counter selection substrate. At least a portion of the first peptide may be randomized. The first peptide may be the native substrate of the protease or kinase. In some embodiments, the first peptide is a sequence that is unrelated to the native substrate or shares no or essentially no sequence identity with the native substrate. The first peptide may be a mutated native substrate of the protease or kinase. The first peptide may have 1, 2, 3, 4, 5 or more mutations, such as substitution mutations, additions, or deletions as compared to the native substrate of the protease or kinase but otherwise shares complete amino acid sequence with the protease or kinase.

In some embodiments, the second peptide sequence is a selection substrate. At least a portion of the second peptide may be randomized. The second peptide may be the native substrate of the protease or kinase. The first peptide may be a mutated native substrate of the protease or kinase. The first peptide may have 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, additions, or deletions as compared to the native substrate of the protease or kinase but otherwise shares complete amino acid sequence with the protease or kinase. In some embodiments, a first promoter controls expression of the first fusion protein, and a second promoter controls expression of the second fusion protein. The first promoter and the second promoter may be expressible in yeast. In some embodiments, the first promoter is Gal1 or Gal10. In some embodiments, the second promoter is Gal1 and Gal10. The nucleic acid may comprise one or more enhancers. The nucleic may also encode a third epitope tag sequence. The third epitope tag sequence may be a hemagglutinin epitope tag. The third epitope tag may be comprised in the first fusion construct. The third epitope tag may be located between (ii) and (iii). The protease or kinase may be a human protease or kinase. The protease may be a TEV-protease, rTPA, human trypsin, a granzyme, a caspase, trypsin, human granzyme K, or a human caspase. The kinase may be a tyrosine kinase. At least a portion of the protease or kinase may be randomized. The first endoplasmic reticulum (ER) targeting sequence and the second endoplasmic reticulum (ER) targeting sequence may be MQLLRCFSIFSVIASVLA (SEQ ID NO:3). The first endoplasmic reticulum (ER) retention sequence and the second endoplasmic reticulum (ER) retention sequence may be FEHDEL (SEQ ID NO:4), KDEL (SEQ ID NO:5), HDEL (SEQ ID NO:6), or RDEL (SEQ ID NO:7).

In some embodiments, the nucleic acid may comprise one or more of the following: (1) the first and/or second ER retention sequences may be removed from the nucleic acid, (2) a stronger promoter may be used for expression of the first and second peptide sequences and/or a weaker promoter may be used to express the protease or kinase, and/or (3) multiple copies of the first and second peptide sequence may be expressed in the nucleic acid vector. To achieve differential expression levels of the first and second peptide sequences versus the protease or kinase, the first and second promoters may be variants of the same promoter, e.g., a Gal1 promoter and a mutant Gal1 promoter that is more or less active than the wild-type Gal1 promoter. Alternatively, the first and second promoters may be different promoters, e.g., a Gal1 promoter and a Gal10 promoter. In either case, the first and second promoters may have relative strengths that are different, e.g., between at least about 1.5- and 100-fold different, between about 2- and 20-fold different, between about 10- and 50-fold different, and any ranges derivable therein.

Another aspect of the present invention relates to a cell comprising a nucleic acid vector of the present invention. The cell may be a yeast cell.

Yet another aspect of the present invention relates to an isolated TEV protease comprising a point mutation at T146, D148, H167, or S170, wherein the protease selectively cleaves an amino acid substrate or a peptide substrate. In some embodiments, the protease is selected from the group consisting of Table 2, Table 3, Table 4, and Table 5. In some embodiments, the amino acid substrate is selected from the list consisting of TENLYFQSGTRRW (SEQ ID NO:8), and TENLYFHSGTRRW (SEQ ID NO:9), TENLYFESGTRRW (SEQ ID NO:10). The protease may be comprised in a pharmaceutical preparation. In some embodiments, the protease is comprised in a kit.

Another aspect of the present invention relates to an isolated TEV protease, wherein the protease comprises at least one point mutation, and wherein the protease selectively cleaves an amino acid substrate selected from the group consisting of ENLYFKS (SEQ ID NO:11), ENLYFES (SEQ ID NO:1), and ENLYFHS (SEQ ID NO:2). The protease may be selected from the group consisting of Table 2, Table 3, Table 4, and Table 5. The protease may be comprised in a pharmaceutical preparation. In some embodiments, the protease is comprised in a kit.

Yet another aspect of the present invention relates to a method for producing a protease, a kinase, a glycosyltransferase, or a sortase, comprising: (i) expressing one or more nucleic acid of the present invention in a plurality of cells; and (ii) purifying or separating cells based on the presence or absence of an antibody that selectively binds the first epitope tag sequence or the second epitope tag sequence. The eukaryotic cell may be a yeast cell. The nucleic acid may further comprise a third epitope tag. The method may further comprise purifying cells that express the third epitope tag. The antibody may be labeled with a fluorophore. The purifying or separating may comprise FACS. The method may comprise isolating the nucleic acid. The method may comprise further randomizing the nucleic acid. The method may comprise further characterizing the protease or kinase encoded by the nucleic acid. The method may comprise repeating steps (i) and (ii).

In some aspects, the methods may be used to generate a modified protease or kinase with increased potency or efficiency as compared to a wild-type protease or kinase. For example, in order to identify a protease or kinase with increased efficiency or potency, one or more of the following strategies may be employed: (1) the first and/or second ER retention sequences may be removed from the nucleic acid, (2) a stronger promoter may be used for expression of the first and second peptide sequences and/or a weaker promoter may be used to express the protease or kinase, and/or (3) multiple copies of the first and second peptide sequence may be expressed in the nucleic acid vector. Thus, one may modify the methods to insure that only a protease or kinase with only at least a certain level of activity is identified as a result of the methods. These approaches may be particularly suited for subsequent rounds of evolution or when steps (i)-(iii) are repeated. These methods may also be used to generate a modified sortase or glycosyltransferase that displays a modified or increased potency or efficiency as compared to a wild-type sortase or a wild-type glycosyltransferase, respectively.

Another aspect of the present invention relates to a protease or kinase produced by a method of the present invention. The protease or kinase may be comprised in a pharmaceutical formulation. In some embodiments, the protease is an rTPA protease. In some embodiments, the kinase is a rAbl tyrosine kinase.

Unless defined otherwise, all technical and scientific terms used herein have the meaning commonly understood by one of ordinary skill in the art relevant to the invention. The definitions below supplement those in the art and are directed to the embodiments described in the current application.

As used herein, an "amino molecule" or "amino acid" refers to any amino acid, amino acid derivative, or amino acid mimic as would be known to one of ordinary skill in the art. In certain embodiments, the residues of the protease or proteinaceous molecule are sequential, without any non-amino molecule interrupting the sequence of amino molecule residues. In other embodiments, the sequence may comprise one or more non-amino molecule moieties. In particular embodiments, the sequence of residues of the protease or proteinaceous molecule may be interrupted by one or more non-amino molecule moieties.

The term "antibody" is used herein in the broadest sense and specifically encompasses at least monoclonal antibodies, polyclonal antibodies, multi-specific antibodies (e.g., bispecific antibodies), naturally polyspecific antibodies, chimeric antibodies, humanized antibodies, human antibodies, and antibody fragments. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes.

"Antibody fragments" comprise a portion of an intact antibody, for example, one or more portions of the antigen-binding region thereof. Examples of antibody fragments include Fab, Fab', F(ab')2, and Fv fragments, diabodies, linear antibodies, single-chain antibodies, and multi-specific antibodies formed from intact antibodies and antibody fragments.

An "intact antibody" is one comprising full-length heavy- and light-chains and an Fc region. An intact antibody is also referred to as a "full-length, heterodimeric" antibody or immunoglobulin.

The term "variable" refers to the portions of the immunoglobulin domains that exhibit variability in their sequence and that are involved in determining the specificity and binding affinity of a particular antibody.

As used herein, the term "complementary nucleotide sequence" refers to a sequence of nucleotides in a single-stranded molecule of DNA or RNA that is sufficiently complementary to that on another single strand to specifically hybridize to it with consequent hydrogen bonding.

An "expression vector" is intended to be any nucleotide molecule used to transport genetic information.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-D: The yeast endoplasmic reticulum sequestration screening system (YESS). FIG. 1A: Salient features of the substrate and protease fusion genes used in the YESS system. FIG. 1B: Schematic showing the rationale for the YESS system. The protease library and the Aga2-substrate fusion polypeptide are expressed from the pESD shuttle vector. The two polypeptides are translocated into the ER, where proteolytic cleavage of the substrate fusion polypeptide gives rise to a product that is displayed on the cell surface by virtue of the N-terminal Aga2. The presence of epitope tags in the processed substrate fusion is detected with fluorescently labeled antibodies to reveal whether selection substrate, the counter selection substrate, or both, had been cleaved. FIG. 1C: An overview diagram or rationale of the YESS method. The TEV-P library and the Aga2-fused TEV-P peptide substrate library were integrated into pESD shuttle vector, which lead to the co-expression and escort of the protease and substrates into the yeast ER. After the enzymatic digestion, the Aga2-fused TEV-P substrates were transported to the yeast cell surface, where the epitope tags associated with the substrates were labeled with different fluorophore-conjugated antibodies on the cell surface, providing a fast and efficient method for cell sorting. FIG. 1D: Scheme of the general strategy for screening the evolved protease. The general steps of the protease library sorting using the YESS system. Step (1): Generating the substrate and protease gene libraries. Step (2): Performing the yeast transformation to incorporate the substrate and protease gene libraries. Step (3): Sorting the yeast cells via FACS analysis. Step (4): Obtaining the initial evolved proteases. Step (5): Sub-cloning the evolved proteases obtained in Step (4) into the expression vector. Step (6): Initial characterization of the evolved proteases obtained in Step (4) to identify the desired variants. Step (7): Based on the results of Step (6), the desired variants were chosen for the second round of library sorting. New protease gene libraries based on these variants were generated and incorporated into the new construct, in which the ER retention sequence was removed from the C-terminus of the protease to generate a more stringent proteolytic condition. Step (2) to Step (7) were repeated until the desired variants were obtained. Step (8): Detailed kinetic analysis was performed for the obtained protease variants.

FIGS. 2A-F: The YESS system was validated using the TEV-P with its canonical substrate ENLYFQS (SEQ ID NO:18) and mutated substrate ENLYFKS (SEQ ID NO:11). All the constructs were generated based on the pESD vector model (see detailed vector information in FIG. 21). After induction with galactose, all the cells were labeled with anti-FLAG-PE and anti-6xHis-FITC antibodies followed by FACS analysis. FIG. 2A: The base pESD vector model. FIG. 2B: Cells containing the construct pESD-I. FIG. 2C: Cells containing the construct pESD-J. FIG. 2D: Cells containing the construct pESD-K. FIG. 2E: Cells containing either pESD-I, pESD-J, or pESD-K were mixed with a cell density ratio of 500:1:500, respectively. The sorting gate was drawn based on the signals presented by the cells containing construct pESD-J. FIG. 2F: Cells after one round of sorting the mixture shown in FIG. 2E. Cells falling in the gate were sorted, grown on an agar plate, and randomly picked for sequencing. Six out of 10 sequences were identified as the target protease vector (pESD-J). The enrichment is from 1:1000 to 6:10, which gives the number of 600.

FIGS. 3A-J: Preparation of the TEV-P substrate P1 position library. Representative FACS data from sorting the TEV-P S1 binding pocket library. FIG. 3A: Pre-screening of the TEV-P substrate library based on the vector pESD-L (FIG. 7G). Cells were labeled with the anti-6xHis-FITC antibody, and the plasmid DNA of the top 3.0% of the cells presenting the highest fluorophore was collected. FIG. 3B: The starting cells after the TEV-P S1 binding pocket library was integrated with the TEV-P substrate library. FIG. 3C-FIG. 3E: FACS data of the cells after the first-, second-, and third-round enrichment. Four gates (P1-P4) were drawn to collect cells after the third-round enrichment. FIG. 3F-FIG. 3I: The fourth-round enrichment of the cells collected from the P1-P4 regions, respectively. FIG. 3J: The vector model of the constructs used in the pre-screening of the TEV-P substrate library (pESD-L, FIG. 21, without the TEV-P S1 pocket library), and the screening of the TEV-P S1 pocket library (pESD-M, FIG. 21, with the TEV-P S1 pocket library). Sequences depicted correspond to SEQ ID NOs: 12 and 23.

FIGS. 7A-G: The ER retention effects in the YESS-YPD system. Five constructs were generated to evaluate the ER retention effects in the YESS-YPD system. All the cells were grown, induced, antibody labeled, and analyzed. FIG. 7A: Cells containing the construct pESD-A; FIG. 7B: Cells containing the construct pESD-B; FIG. 7C: Cells containing the construct pESD-C; FIG. 7D: Cells containing the construct pESD-D; FIG. 7E: Cells containing the construct pESD-E; FIG. 7F: Cells containing either pESD-A or pESD-E were mixed with a cell density ratio of 1:1, respectively; FIG. 7G: Vector maps of the pESD constructs. ER signaling peptide MQLLRCFSIFSVIASVLA (SEQ ID NO:3) and ER retention sequence FEHDEL (SEQ ID NO:4) are shown in FIG. 7G. Peptide 1 and 2 correspond to SEQ ID NOs: 17 and 18, respectively.

FIG. 9A: Cells expressing the TEV-PE3; FIG. 9B: Cells expressing the mutated TEV-PE3 in which the ER-retention signal peptide was removed from the C-terminus of the protease; FIG. 9C: The starting cells after the TEV-PE3 error-prone library was integrated with the ENLYFES(SEQ ID NO:1)-containing pESD vector. FACS data of the cell sorting of the TEV-PE3 based error-prone PCR library. Data were recorded after the first-, second-, third-, and fourth-round enrichment.

FIG. 10A: Cells expressing the TEV-PH7; FIG. 10B: Cells expressing the mutated TEV-PH7 in which the ER-retention signal peptide was removed from the C-terminus of the protease; FIG. 10C: The starting cells after the TEV-PE7 error-prone library was integrated with the ENLYFHS (SEQ ID NO:2) containing pESD vector. FACS data of the cell sorting of the TEV-PH7 based error-prone PCR library. Data were recorded after the first-, second-, third-, and fourth-round enrichment.

FIG. 13A: Diagrams of the protein substrate purification constructs (MBP-ENLYF XS-6xHis-GST, MBP-SEQ ID NO:15-GST) and the protease purification constructs (MBP-ENLYFXS-6xHis-TEV-P, MBP-SEQ ID NO:15-TEV-P). X can be Q, E, and H, correspondent to TEV-P, TEV-PE10, and TEV-PH21, respectively. FIG. 13B: The SDS-PAGE analysis of the purified TEV-P, TEV-PE10, and TEV-PH21. Lane 1: molecular mass ladders; Lane 2: 10 µg purified TEV-P; Lane 3: 10 µg purified TEV-PE10; Lane 4: 10 µg purified TEV-PH21.

FIG. 14A: HPLC analysis of the digestion of peptide substrates by the TEV-P, TEVPE10, and TEV-PH21. 1: 0.1 µM TEV-P incubated with 100 µM TENLYFQSGTRRW ($PepS_Q$, SEQ ID NO:8); 2: 0.1 µM TEV-PE10 incubated with 100 µM TENLYFQSGTRRW ($PepS_Q$, SEQ ID NO:8); 3: 0.5 µM TEV-PH21 incubated with 100 µM TENLYFQSGTRRW ($PepS_Q$, SEQ ID NO:8); 4: 1 µM TEV-P incubated with 100 µM TENLYFESGTRRW ($PepS_E$, SEQ ID NO:10); 5: 0.1 µM TEV-PE10 incubated with 100 µM TENLYFESGTRRW ($PepS_E$, SEQ ID NO:10); 6: 1 µM TEV-P protease incubated with 100 µM TENLYFHSGTRRW ($PepS_H$, SEQ ID NO:9); 7: 0.5 µM TEV-PH21 incubated with 100 µM TENLYFHSGTRRW ($PepS_H$, SEQ ID NO:9). The sequence for peak indicated as SGTRRW is provided as SEQ ID NO:51. The corresponding products were confirmed using Mass Spectrometry. Plots of substrate concentration versus rate of FIG. 14B: the TEV-P against the TENLYFQSGTRRW ($PepS_Q$, SEQ ID NO:8); FIG. 14C: the TEV-P against the TENLYFESGTRRW ($PepS_E$, SEQ ID NO:10); FIG. 14D: the TEV-P against the TENLYFHSGTRRW ($PepS_H$, SEQ ID NO:9); FIG. 14E: the TEV-PE10 against the TENLYFQSGTRRW ($PepS_Q$, SEQ ID NO:8); FIG. 14F: the TEV-PE10 against the TENLYFESGTRRW ($PepS_E$, SEQ ID NO:10); FIG. 14G: the TEV-PH21 against the TENLYFQSGTRRW ($PepS_Q$, SEQ ID NO:8); FIG. 14H: the TEV-PH21 against the TENLYFHSGTRRW ($PepS_H$, SEQ ID NO:9).

FIGS. 15A-C: Protein substrate digestion by the TEV-P, TEV-PE10, and TEV-PH21 under different pH conditions. The SDS-PAGE analysis of the protein substrate digestion by the TEV-P and its variants. Protein substrate digestion reactions were incubated at 30° C. for 1 h with 5 µg protein substrates mixed with 0.1 µg proteases in 20 µL reaction buffer. FIG. 15A: reactions performed at pH 8.0; FIG. 15B: reactions performed at pH 7.2; FIG. 15C: reactions performed at pH 6.5.

FIG. 17A: Cells expressing substrate fusion only (construct pESD-A in FIG. 17F); FIG. 17B: Cells co-expressing protease and substrate fusion both containing ER retention sequences (construct pESD-B in FIG. 17F); FIG. 17C: Cells as in FIG. 17B except that TEV-P lacks the ER retention sequence (construct pESD-C in FIG. 17F); FIG. 17D: Cells as in FIG. 17B except that both TEV-P and the substrate fusion lack the ER retention sequences (construct pESD-D in FIG. 17F); FIG. 17E: A 1:1 mixture of cells from FIG. 17A and FIG. 17B above; FIG. 17F: Schematic of the constructs pESD-A, pESDE-B, pESD-C, and pESD-D. The counter selection encodes the substrate of HCV protease (DEMEECASHL, SEQ ID NO:17), and the selection substrate encodes the substrate of TEV-P (ENLYFQS, SEQ ID NO:18).

FIG. 18A: Two-color FACS analysis of the library cells. FIGS. 18B-D: Two-color FACS of cells after the first, second, and third round of sorting. FIG. 18E: The TEV-PE3 variant. FIG. 18F: The TEV-PH7 variant. FIG. 18G: Molecular model of the S1 pocket of the wild-type TEV-P, and the amino acid substitutions introduced in the TEV-PE10 variant. The P1 residue (Gln) of the substrate peptide interacts with the TEV-P S1 pocket residues (emphasized in rectangular boxes) through the hydrogen bonds (dotted line, heavy shading) and the hydrophobic interactions (dotted line, light shading). In the TEV-PE10, mutations that are close to the new S1 pocket (P1 residue is replaced with Glu) were annotated. Image is generated based on the PDB file 1LVB.

FIG. 19A: HCV protease was assayed in the YESS system. Light shade data indicates negative control consisting of the HCV protease preferred substrate construct with no HCV protease (construct pESD-N, FIG. 21; data points clustered in a line at the center of the FIG). Heavy shade data indicates HCV protease expressed along with its preferred substrate construct (construct pESD-O, FIG. 21; data points shifted to the right). FIG. 19B: Human granzyme K was assayed in the YESS system. Light shade data indicates negative control consisting of the human granzyme K preferred substrate construct with no human granzyme K (construct pESD-P, FIG. 21; data points clustered in a line at the center of the FIG). Heavy shade data indicates human granzyme K expressed along with its preferred substrate construct (construct pESD-Q, FIG. 21; data points shifted to the right). FIG. 19C: Human Abelson tyrosine kinase (AblTK) was assayed in the YESS system. Light shade data indicates human AblTK expressed along with its preferred substrate construct (construct pESD-R, FIG. 21; data points clustered in a line at the center of the FIG). Heavy shade data indicates negative control consisting of the human AblTK preferred substrate construct with no human AblTK (construct pESD-S, FIG. 21; data points shifted to the right).

FIG. 20A: The vector model of the constructs used in the time-course experiments to evaluate the ER retention effects of different ER retention sequences (e.g., MQLLRCFSIFS-VIASVLA (SEQ ID NO:3)). The counter selection encodes the substrate of HCV protease (DEMEECASHL, SEQ ID NO:17), and the selection substrate encodes the substrate of TEV-P (ENLYFQS, SEQ ID NO:18). FIG. 20B: The time-course experiments. Cells containing different vectors were grown, induced, and analyzed using FACS. Line indicated with diamonds: vector contains no protease gene and no ER retention sequence at the C-terminal of substrate (construct pESD-E, FIG. 21). Line indicated with squares: vector contains no protease gene but the KDEL (SEQ ID NO:5) ER retention sequence at the C-terminal of substrate (construct pESD-F, FIG. 21). Line indicated with triangles: vector contains no protease gene but the FEHDEL (SEQ ID NO:4) ER retention sequence at the C-terminal of substrate (construct pESD-G, FIG. 21). Line indicated with crosses: vector contains TEV-P gene with the FEHDEL (SEQ ID NO:4) ER retention sequence anchored at its C-terminus, and also the FEHDEL (SEQ ID NO:4) ER retention sequence at the C-terminus of the substrate (construct pESD-H, FIG. 21). The existence of the TEV-P will cause the cleavage at the selection substrate region, removing the ER retention sequence from the C-terminus of the substrate.

DESCRIPTION OF ILLUSTRATIVE EMBODIMENTS

The present invention provides, in various aspects, a yeast ER sequestration (YESS) approach for screening large libraries of protease or kinase variants for altered specificity and/or high overall catalytic activity. This general approach may be used to generate proteases, such as modified TEV proteases, or kinases, such as modified Abl tyrosine kinases, that exhibit modified specificity, potency, or efficiency. In various aspects, specific modified TEV proteases that exhibit altered specificity are provided.

As shown in the below examples, the YESS approach may be utilized to allow for protease and substrate sequences to be co-expressed and targeted (Pelham et al., 1988; Semenza et al., 1990) to the yeast endoplasmic reticulum (ER) in order to facilitate protease-substrate interaction in a relatively confined environment. Following the encounter with a protease variant in the ER, the cleaved/uncleaved substrate can be transported to the yeast surface using, e.g., the Aga2p yeast display system (Boder and Wittrup, 1997). A set of internal immunotag sequences on the substrate can be used in conjunction with the corresponding fluorescently labeled antibodies to report the location and extent of cleavage during ratiometric fluorescence activated cell sorting (FACS) of the library. In order to screen against unwanted promiscuous protease variants, the substrate construct can be designed to contain a single selection substrate sequence along with one or more counter selection substrate sequences. An advantage of this strategy is that intracellular expression of both the protease and substrate are used such that a library of protease variants can be screened against a library of substrate sequences in a "library-on-library" experiment. The library on library approach should increase the odds that a highly active engineered protease-novel substrate pair can be identified through directed evolution. Using the YESS library-on-library approach, 52 different TEV-P variants that can recognize six different peptide substrates were isolated. Two variants, TEV-PE10 and TEV-PH21, which recognize E and H in P1, respectively, were further characterized. A 5000-fold change in substrate specificity was obtained with TEV-PE10, and an 1100-fold change was obtained for TEV-PH21 compared to wild-type TEV-P. These results demonstrate that the YESS system can be very effectively used for protease engineering in eukaryotic cells.

I. YESS SYSTEM FOR PROTEASE OR PROTEIN KINASE ENGINEERING

Figure 1C:
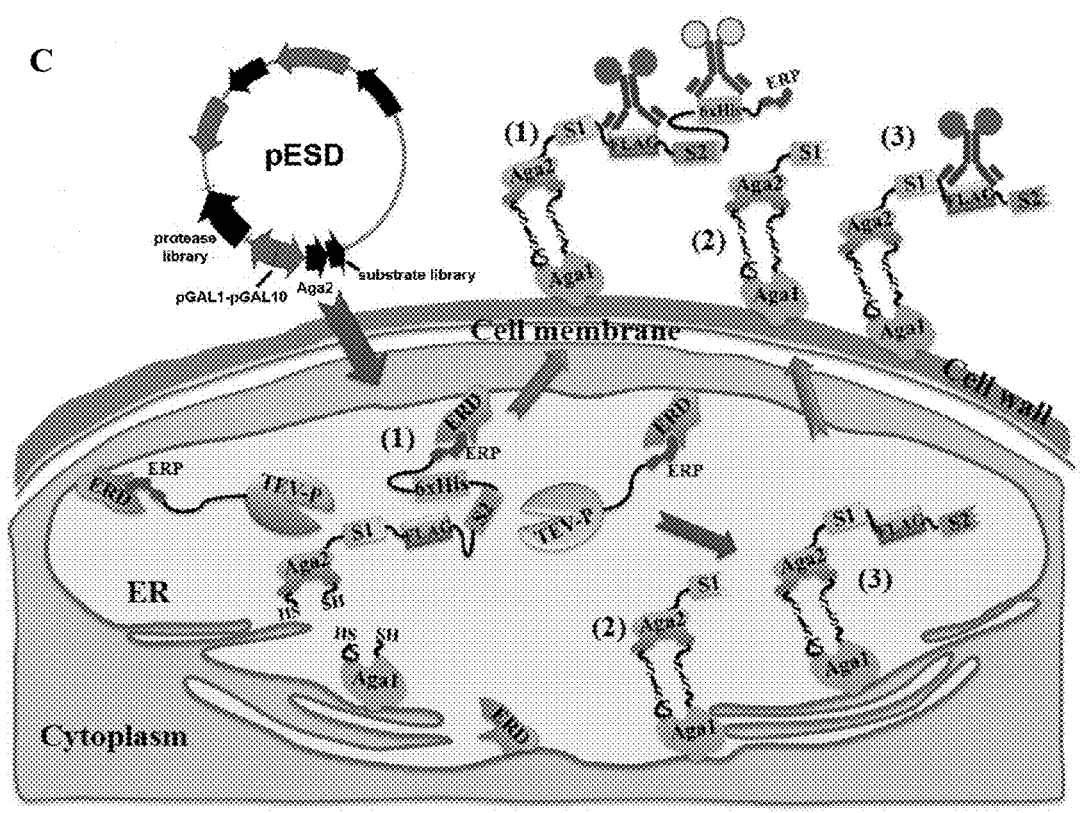

An overview of the YESS protease engineering strategy used in the below examples is presented in FIG. 1B and FIG. 1C. In some embodiments, a protease variant and a cell-surface display (e.g., Aga2)-fused peptide substrate are co-expressed, transported into the yeast endoplasmic reticulum (ER) due to an N-terminal ER signal sequence (e.g., MQLL-RCFSIFSVIASVLA, SEQ ID NO:3), and anchored on the ER inner membrane through a C-terminal fusion to the ER retention signal peptide (e.g., FEHDEL, SEQ ID NO:4). In some embodiments, a protein kinase variant may be substituted for the protease variant using these methods. Without wishing to be bound by any theory, the ER targeting may be used to increase the opportunity for a protease-substrate interaction to occur in the confined environment of the ER, thus improving the sensitivity of the assay. Due to a cell-surface (e.g. Aga2) fusion in the substrate construct, the cleaved/uncleaned substrate can be subsequently transported then attached to the yeast surface Where it can be labeled with antibodies to detect and quantify the location and extent of cleavage. On the pESD vector (FIG. 6), co-expression of the protease and its substrates are under the control of the galactose inducible GAL1 and GAL10 promoters, respectively. The bidirectional GAL1-GAL10 hybrid promoter, in which GAL1 promoter has a similar individual strength with GAL10 promoter, is used to drive relatively high-level expression of both the protease and the substrate constructs, although they are expressed as entirely separate polypeptides.

In some aspects, a modified kinase may be generated by these methods. The kinase is preferably a protein kinase, such as, e.g., a tyrosine kinase, a serine/threonine-specific protein kinase, a protein-dual-specificity protein kinase, a protein histidine protein kinase, a protein-histidine pros-kinase, a protein-histidine tele-kinase, or a histidine kinase. As shown in the below examples, a mutant Abl tyrosine kinase with modified activity was generated. It is anticipated that virtually any kinase may be used with the methods disclosed herein. For example, if one has one or more enzymes that can distinguish between phosphorylated and unphosphorylated peptides or proteins, then one or more cells expressing a mutant kinase may be identified, e.g., via FACS. Specific kinases types that may be generated include, e.g. the various members of the eukaryotic protein kinases superfamily including the AGC, CAMK (CaM Kinases), CMGC, CK1, STE, TKL, and thymidine kinases (TK kinases).

In some embodiments, methods of the present invention may be used to generate an engineered sortase. The sortases are an enzyme class characterized by the ability to ligate two different peptide sequences together. In the sortase reaction mechanism, a first substrate peptide sequence is recognized and cleaved at a specific site to produce a free carboxylic acid group, then the amine terminus of a second specific peptide is attached to this carboxyl group to give the ligated construct. Adapted to the YESS approach, a first peptide substrate sequence containing the sortase cleavage site may be attached or fused to a sequence to allow for yeast cell surface attachment (e.g., such as the AGA2 sequence in some preferred embodiments), and a second peptide substrate sequence that can serve as the peptide to (possibly) be ligated at its amine terminus is preferably fused to an antibody epitope. Both of these substrate sequences may be targeted to the ER for expression via an ER specific signal sequence similar to those used in the protease and kinase embodiments. Only if a sortase, also expressed in the same yeast cell and targeted to the ER, ligates the first peptide substrate sequence to the second peptide substrate sequence, will the epitope be attached to the cell surface via the AGA2 linkage. The presence of epitopes (from the second sequence) attached to the yeast surface will therefore be a direct measure of sortase activity, that can be identified though binding of a labeled antibody that recognizes the epitope (e.g., via FACS). Sequences in the engineered sortase may be randomized, e.g., at or near sites involved sequence recognition, cleavage, and/or ligation, etc. Thus, a sortase may be included as the enzyme in a nucleic acid vector of the present invention and used to engineer a modified sortase that displays, e.g., modified activity, potency, or specificity. In addition, one or both of the substrate sequences can be randomized to develop a comprehensive profile of the substrate specificity of a sortase of interest.

In some embodiments, methods of the present invention may be used to generate an engineered glycosyltransferase. For example, methods used to engineer a glycosyltransferase may be very similar to a the methods used to generate an engineered kinase; however, instead of using an antibody to recognize the presence or absence of a phosphorylation event, an antibody that recognizes the presence or absence of a glycosylation event (e.g., transfer of a carbohydrate, glycoside, oligosaccharide, or a polysaccharide to an amino acid sequence) may be used to identify and or separate one or more glycosyltransferases that exhibit a desired activity. Sequences in an engineered glycosyltransferase may be randomized, e.g., at or near sites involved in sequence recognition or activity, etc. Thus, a glycosyltransferase may be substituted for a kinase in nucleic acid vectors of the present invention and used to engineer a modified glycosyltransferases that displays, e.g., modified activity, potency, or specificity.

A major problem encountered in early protease engineering work was that often, attempts to alter protease specificity only resulted in the production of promiscuous enzymes. As shown in the below examples, the inventors were able to overcome this difficulty by incorporating one or more counter selection substrate sequences into the screening protocol (Varadarajan et al., 2008; Varadarajan et al., 2009a). In a simultaneous selection/counter selection screen, only those proteases are isolated that maximize cleavage of a desired new substrate sequence while minimizing promiscuous cleavage of the original wild-type or other unwanted substrate sequence. In various aspects, the protease itself may on occasion act as an effective counter selection substrate in the sense that any protease variant with specificity relaxed to the point that it efficiently cleaves itself will not exhibit a positive signal.

A simultaneous selection/counter selection FACS assay may be achieved by placing elements in the following order: An N-terminal Aga2P anchoring sequence followed by the wild-type preferred counter selection substrate sequence (Peptide 1), the FLAG epitope tag sequence, the selection substrate sequence, a 6xHis sequence, and a C-terminal ER retention signal (See FIG. 2). Note that the 6xHis sequence serves as an epitope tag owing to the ready availability of anti-6xHis antibodies. The anti-FLAG and anti-6xHis antibodies may be purchased as the phycoerythrin (PE) and FITC conjugates, respectively. Specific cleavage at the desired new substrate sequence (only Peptide 2) would result in a product that maintains the FLAG epitope, but not the 6xHis sequence. Thus, a yeast cell harboring a protease variant with a desired new substrate activity would have high PE fluorescence, but relatively low FITC fluorescence. A nonspecific protease would lead to cleavage at both the counter selection and selection sequences, leading to no signal with either antibody. Similarly, an enzyme with unaltered wild-type specificity would give a similar lack of signal with either antibody due to cleavage at the Peptide 1 sequence. Protease variants with no activity with either sequence would have similarly high PE and FITC signals. These three outcomes are easily separated by FACS using a two-dimensional analysis in which gates are set for high signal in the PE channel, but low signal in the FITC channel.

In some aspects, the YESS approach can display a very significant or unprecedented versatility and a tunable dynamic range. It is straightforward to vary the sequence of the protease, or the selection substrate cleavage sequence, or both simultaneously. Thus, the YESS system may be used to carry out a variety of experiments, including, e.g., the following three distinct types of experiments: 1) A protease library could be screened in an effort to identify activity with a single, desirable new target sequence. 2) A single protease could be screened against a library of substrate sequences to identify the overall substrate preferences of a protease. 3) In an attempt to maximize the chances of finding a protease variant with altered sequence specificity, a protease library could be screened against a library of potential target substrate sequences, a so-called "library-on-library" experiment. An advantage of the YESS approach is that the dynamic range of the assay can be adjusted by subtracting the ER retention sequences on either the protease or substrate sequences, or both. In this way, the stringency of the assay can be significantly increased by reducing the amount of time the protease and substrate can interact in the confines of the ER.

In addition, the compartmental nature of eukaryotic cells makes possible the specific targeting of both protease and substrate to the same compartment, namely the ER. Having the protease interact with substrate in the relatively confined environment of the ER provides a considerable level of control that is not possible in the cytoplasmic milieu. In particular, by adding a C-terminal ER retention sequence, both the protease and substrate can be anchored on the ER membrane, increasing ER residence time, local protease/substrate concentrations, and therefore assay sensitivity. Increased assay sensitivity may be particularly helpful during initial library screens. When intermediate sensitivity is needed, for example during the middle rounds of library optimization/screening, the ER retention signal can be left off of either the protease or substrate. At the end of a screening experiment, when only the most active variants are being sought, the assay can be made even less sensitive by leaving off the ER retention sequences altogether. Consistent with the assay design criteria, wild-type TEV-P gave a maximum FACS signal with its preferred substrate when both the protease and substrate had the ER retention signals attached (FIGS. 7A-G). Intermediate FACS signals were seen when only one component had the ER retention signal and the least intense FACS signal was seen when no ER retention signal was present (FIGS. 7A-G). To the knowledge of the inventors, such precise control over the dynamic range of a high-throughput enzyme library-screening assay is unprecedented. The strong signal correlation of FACS signal with ER retention signals supports the idea that the protease-substrate interaction can occur primarily, if not entirely, within the ER.

The YESS approach incorporates two additional powerful features useful for library screening. Simultaneous selection and counter selection screens may be used to avoid isolating variants with relaxed specificity (Varadarajan et al., 2005; Varadarajan et al., 2008; Sellamuthu et al., 2008; O'Loughlin et al., 2006). Any number of counter selection substrate sequences (e.g., 1, 2, 3, 4, 5, 6, 7, 8, 9, 10, or more) can be added to the YESS substrate construct to refine specificity. Additionally, because both the protease and substrate constructs are typically genetically encoded in the YESS approach, a library can be used for either one. Thus, a novel protease substrate specificity for a single desired substrate can be sought, e.g., by using a protease library with one substrate construct. The converse situation, in which a single protease is used in conjunction with a substrate library, can be used to identify the substrate specificity profile of a protease. In order to improve the chances of finding a new protease-substrate combination, a protease library can be screened against a substrate library. The inventors used this "library-on-library" approach to alter the P1 substrate specificity of the TEV-P. As shown in the below examples, all four contact residues in the putative 51 subsite of TEV-P were randomized as well as the P1 residue of the substrate in attempt to isolate TEV variants with novel P1 specificities. Combinatorial saturation of the residues that form the 51 subsite of TEV-P enables the isolation of enzyme variants capable of accepting six different amino acids other than Gln in P1. Notably, TEV-P mutants were identified that display selectivity for a new amino acid over the Gln that is overwhelmingly preferred by the wild-type enzyme at that position.

Figures 1, 3A:
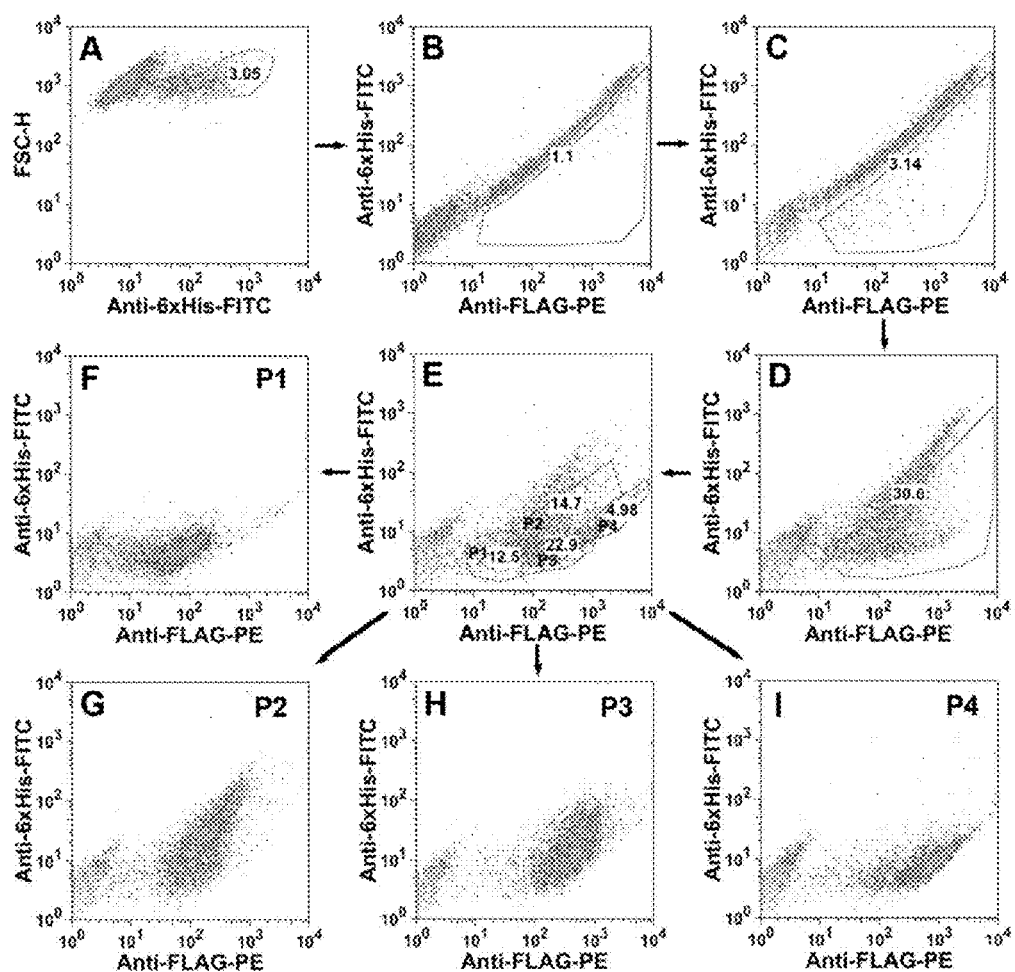
Figure 3J:
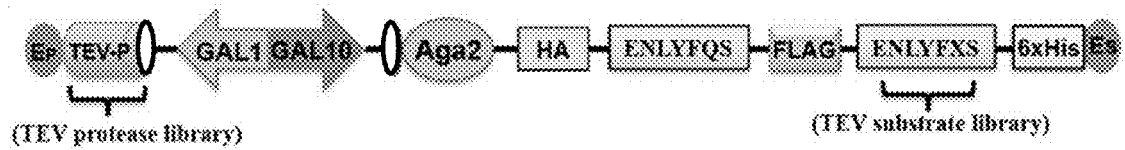

As shown in Table 3, 52 different active variants with activity toward six different substrates were obtained from the initial library screening. Without wishing to be bound by any theory, several factors likely lead to this success. The wild-type preferred sequence, including Gln at P1, was used as the counter selection portion of the substrate construct in an effort to maximize overall specificity by minimizing wild-type activity. Notably, a stop codon inserted in the substrate sequence or an otherwise truncated construct, such as a frame-shift, would give a false positive FACS signal by mimicking a cleaved product. For this reason, all stop codon containing or frame-shifted substrate constructs were removed in a preliminary FACS screen (FIG. 3A). The pre-screened substrate library was then combined with the TEV S1 library, followed by FACS screening. In order to cast a "wide net" in the initial screens, assay sensitivity was increased by including the C-terminal ER retention signals in both the protease and substrate constructs.

Figure 13:
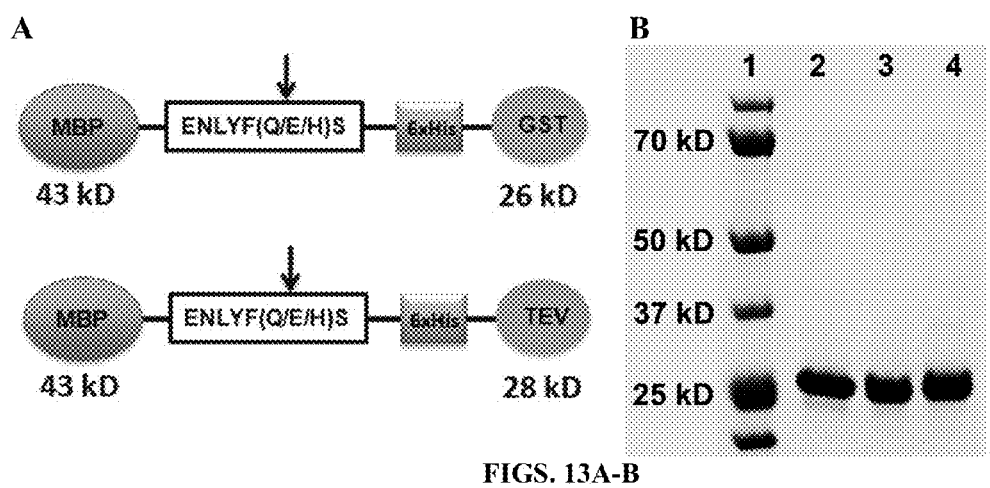
FIGS. 13A-B: Protein purification of wild-type TEV protease and its variants.
Figure 19:
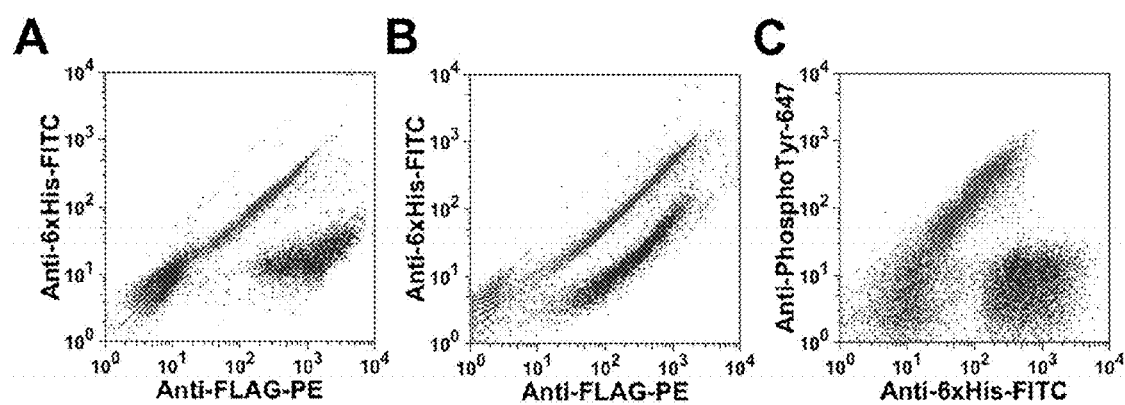
FIGS. 19A-C: Detection of granzyme K and the HCV protease by YESS.

As shown in the below examples, the tunability of the YESS assay was used to advantage while screening the second generation error-prone PCR libraries constructed from the two most promising isolated clones, one specific for Glu and the other specific for His at P1. In particular, by removing the ER retention sequences from the C-terminus of the protease, only variants with relatively high levels of activity produced a significant FACS signal. Once again, wild-type preferred Gln at P1 was used as counter selection. As a result, two clones (TEV-PE10 and TEV-PH21) displaying substrate specificity reversals of 5,000-fold and 1,100-fold, respectively, along with relatively high overall catalytic activity were identified. In fact, the TEV-PE10 variant displayed a $k_{cat}/K_M$ that was roughly 2-fold higher than that of even TEV-P reacting with its preferred substrate, verifying that new specificity did not come at the expense of overall catalytic activity. As further evidence of successful protease engineering, TEV-PE10 and TEV-PH21 were shown to be efficient in the processing of GST-MBP fusions containing their preferred recognition sequences, namely MBP-ENLYF ES-GST (MBP-SEQ ID NO:1-GST) and MBP-ENLYF HS-GST (MBP-SEQ ID NO:2-GST) respectively (FIG. 4: FIG. 13). Importantly, the generality of the YESS approach was demonstrated by showing that a human (granzyme K) and another viral (HCV) protease are also amenable to expression and quantitative assay using the YESS system (FIG. 19).

Most applications of proteases involve the cleavage of proteins, not peptides. Notably, the altered specificities measured for TEV-PE10 and TEV-PH21, using peptide substrates, translated into similar results when cleaving the corresponding GST-MPB fusion proteins (FIG. 4; FIG. 15). Thus, these results indicate that the methods disclosed herein may be used to generate a wide variety of specific proteases, e.g., based upon engineered versions of TEV-P or other proteases.

Figure 5:
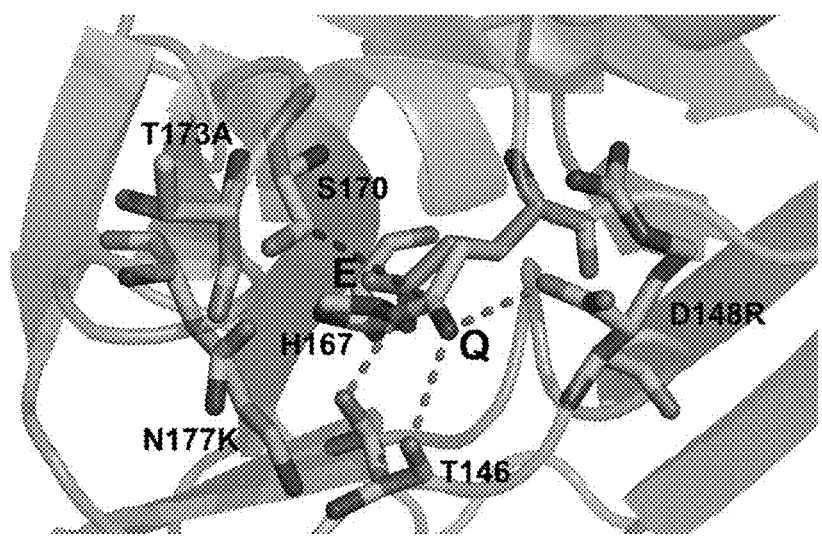
FIG. 5: Mutations of the TEV-PE10 responsible for substrate binding. The residues that might be involved in the interactions between the TEV-PE10 and the Glu residue in the $PepS_E$ substrate are labeled. The hydrogen bonds (dotted line, light shading) and the hydrophobic interactions (dotted line, heavy shading) between the S1 binding pocket residues of the TEV-P and the Gln residue in the $PepS_Q$ substrate are also marked. All the residues are shown with nitrogen in blue and oxygen in red. Image is generated based on the PDB file 1LVB.

Without wishing to be bound by any theory, the origin of substrate specificity in the isolated variant TEV-PE10 was predicted (FIG. 5) and may be useful for interpreting the engineered TEV proteases identified in the below examples. The negatively-charged D148 was mutated to the positively-charged residue Arg, likely favoring interaction with the presumably deprotonated and therefore negatively-charged Glu residue at P1. This theory was further supported by the TEV-PE1 (D148K) variant (Table 3). In addition to the D148R replacement, two other mutations, T173A and N177K, which were not present in the S1 binding pocket of the TEV-P (Phan et al., 2002), might also be involved in the binding of the TEV-PE10 against with an E residue at P1 (FIG. 5). Compared to the TEV-PE10 variant, it is less clear how the observed mutations in TEV-PH21 favor reaction with His at P1 since the TEV-PH variants did not show any consistent mutations that were obviously charge-related. However, all the TEV-PH variants contained mutations of T146 and D148 to residues, such as Ala, Pro, Cys, and Ser. These mutations might be involved in the expanding of the docking space for the His residue in the new S1 binding pocket.

In summary, the below data demonstrates that the YESS system can be used to generate proteases with significantly altered substrate specificity while maintaining high overall catalytic activity. It is anticipated that assay dynamic range tunability and the incorporation of a counter selection substrate sequence may be very helpful for success. The YESS system may be used in other applications of protease engineering, including the development of potential therapeutic proteases. In addition, the methods disclosed herein may be used to detect other enzymatic reactions compatible with reaction in the ER, where the reaction product is displayed and detected on the yeast outer surface.

II. PROTEASES

The present invention may be used in various aspects to engineer a protease. A variety of proteases may be generated via these methods, such as, e.g., a TEV protease, a tissue plasminogen activator, such as a recombinant tissue plasminogen activator (rTPA), a protease that targets or affects the function of a proteinase-activated receptor (PAR), or any protease capable of expression in yeast. In some embodiments, the engineered protease may be used in research to cleave a peptide linker, e.g., to separate protein entities in a fusion protein. In some embodiments, the engineered protease is a therapeutic protease. The therapeutic protease may be useful in treating diseases, including, but not limited to, cardiovascular disease, sepsis, a digestive disorder, inflammation, cystic fibrosis, a retinal disorder, psoriasis, cancer, a cell proliferative disease, diabetes, blood coagulation disorders (e.g., hemophelia, a deficiency in factor 7 and/or factor 9), an autoimmune disorder (e.g., psoriasis, lupus, etc.), an inflammatory lung disease (e.g., cystic fibrosis, emphysema, sarcoidosis, etc.), or asthma, as well as in disorders of the cardiovascular, musculoskeletal, gastrointestinal, respiratory, and/or central nervous system.

The methods provided herein may be used as a fast and efficient high-throughput screening method to identify new proteases. The YESS system may be used to isolate desired variants from large protease libraries, and may be used in a wide range of potential applications for proteases. Several proteases, such as the important protease rTPA, are currently used clinically (Craik et al., 2011; Ramachandran et al., 2012), but the therapeutic application of proteases has thus far been limited to situations in which a naturally occurring protease cleavage specificity is of therapeutic benefit. The ability to precisely engineer a desired new sequence specificity into a human protease may facilitate the investigation of proteases as a general alternative to antibody therapeutics (Craik et al., 2011; Ramachandran et al., 2012). Compared to antibodies, which are relatively large molecules that bind/inactivate their therapeutic targets in stoichiometric fashion, a properly engineered therapeutic protease may require a much lower dose because it is significantly smaller and capable of catalytic inactivation of its target. Moreover, other proteases, such as TEV-P and subtilisin, have found significant academic as well as commercial application, and adding one or more new specificities would dramatically increase their potential uses.

TEV Proteases

In some embodiments, the protease is a TEV protease. TEV protease is a catalytic part of the Nuclear Inclusion protein "a" (NIa) from tobacco etch virus (TEV). TEV is a cysteine protease that specifically recognizes and cleaves a linear epitope with the general sequence E-X-X-Y-X-Q-(G/S) (where X is any amino acid, SEQ ID NO:20) (Dougherty et al., 1989; Dougherty and Parks, 1989; Dougherty et al., 1988; Kapust et al., 2002a). For a native TEV protease, the cleavage typically occurs between Q and G/S. The most common sequence is ENLYFQG (SEQ ID NO:21) or ENLYFQS (SEQ ID NO:18). As shown in the present invention, modified TEV proteases may be generated that exhibit altered specificity, efficiency, and/or potency. For reference, the wild-type TEV protease (TEV-P) preferably has the sequence (SEQ ID NO:52). In some preferred embodiments, the wild-type TEV-P contains the S219P mutation. Another wild-type TEV protease (TEV-E) that may contain one or more mutation as indicated herein preferably has the sequence (SEQ ID NO:53).

TEV proteases may be resistant to many widely used serine and cysteine protease inhibitors, such as PMSF, AEBSF, TLCK, E-64, or "Complete" protease inhibitor cocktail (Roche). Robust enzyme activity may be observed in a wide range of different buffers (with NaCl varied from 0 to 0.4 M and in pH from 4 to 9, enzyme tolerates MES, acetate, phosphate, glycerol, and sorbitol).

TEV proteases may be used for tag removal from thermolabile proteins. TEV proteases may be active in a broad temperature range, e.g., from about 4° C. to about 30° C. (although the native enzyme is about three times less active at 4° C. than at 30° C.) (Nallamsrtty et al., 2004). TEV proteases may be sensitive to some detergents (Mohanty et al., 2003).

TEV proteases may be particularly useful for removing affinity tags from fusion proteins in conditions friendly for a target protein. TEV proteases may be genetically modified to reduce autolysis (self-cleavage) and increase catalytic activity, as compared to the wild-type enzyme.

III. CONSTRUCTS COMPRISING OR ENCODING AN ENGINEERED PROTEASE

Certain aspects of the present invention involve nucleic acids that encode a protease and/or an amino acid substrate. The protease and the substrate may be expressed as a fusion protein with one or more additional sequences, such as an ER targeting sequence, an ER retention sequence, a cell-surface sequence, and/or one or more immunotag sequences. In some embodiments, a single nucleic acid may be used to express both a protease and an amino acid substrate in a cell. It is generally anticipated that, although expressing both a protease and an amino acid substrate from a single vector or construct may effectively allow for interactions between the protease and amino acid substrate in a cell, in some embodiments the protease and amino acid substrate may be encoded by two different or separate nucleic acids or vectors, and the two nucleic acids may be expressed in a cell, such as a yeast cell.

As shown in the below examples, the following construct may be generated. Under the control of the GAL10 promoter and after the Aga2 gene used for yeast surface display, a five-part cassette may be cloned consisting of (1) the native substrate of a protease (e.g., TEV-P, ENLYFQS, SEQ ID NO:18); (2) a first epitope tag sequence (e.g., a FLAG tag, DYKDDDDK, SEQ ID NO:22); (3) the designed peptide substrate library (e.g., ENLYFXS, X can be any residue, SEQ ID NO:23); (4) a second epitope tag (e.g., 6xHis tag, HHH-HHH, SEQ ID NO:24); and (5) an ER retention signal peptide (e.g., FEHDEL, SEQ ID NO:4). Under the control of the GAL1 promoter, the protease library (such as the TEV-P library, see below) may be cloned along with a designed N-terminal ER targeting signal peptide (QLLRCFSIFSVI-ASVLA, SEQ ID NO:25) and with or without a C-terminal ER retention signal peptide.

Endoplasmic Reticulum (ER) Targeting Sequences

The construct may comprise 1, 2, or more sequences for targeting an amino acid sequence (e.g., comprising a protease or a substrate sequence) to the endoplasmic reticulum (ER). In some embodiments, the HDEL (SEQ ID NO:6) system may be used as described in Monnat et al. (2000), which is incorporated by reference herein in its entirety. In some embodiments, the ER targeting signal peptide (QLLRCF-SIFSVIASVLA, SEQ ID NO:25) is used. The ER targeting signal peptide may be at or near the N-terminal portion such that an amino acid comprising a protease or substrate sequence can be targeted to the ER.

Without wishing to be bound by any theory, the ER targeting sequence may bind a ribosome and allow for the amino acid to be transported into the ER. Generally, an ER targeting sequence may promote entry of an amino acid sequence, peptide, or protein, by promoting entry of the protein into the ER through the translocon, e.g., via a protein-conducting channel formed by a conserved, heterotrimeric membrane-protein complex referred to as the Sec61 or SecY complex. In some embodiments, a sequence disclosed as an ER targeting sequence of Rapoport (2007), Hedge and Keenan (2011), or Park and Rapoport (2012) may be used with the present invention. In some embodiments, an N-terminal targeting sequence for promoting entry into the endoplasmic reticulum may be identified via the Predotar (Prediction of Organelle Targeting sequences) method disclosed in Small et al. (2004).

Endoplasmic Reticulum (ER) Retention Sequences

Once in the ER, in certain embodiments, it may be preferable to include an ER retention sequence or peptide in order to allow or promote an amino acid (e.g., comprising a protease or a substrate sequence) to remain in the interior of the ER.

In some embodiments, the ER retention signal peptide is FEHDEL (SEQ ID NO:4). The HDEL (SEQ ID NO:6) system may be used as described in Monnat et al. (2000). In some embodiments, a protein chimera may be generated that contains a C-terminal tetrapeptide sequences of (-KDEL (SEQ ID NO:5), -HDEL (SEQ ID NO:6), or -RDEL (SEQ ID NO:7)) to promote retention in the ER. If only a partial retention in the ER is desired, a protein chimera may be generated that contains C-terminal sequence (-KEEL, SEQ ID NO:26). In some embodiments where it is desirable a mammalian cell line for expression of constructs, it may be useful to use the mammalian (-KDEL, SEQ ID NO:5) sequence in a fusion protein with a protease or a substrate. The particular ER retention sequence used may be chosen based on the amount of retention in the ER produced in a particular eukaryotic cell type. In some embodiments, an upstream sequence beyond the C-terminal tetrapeptide may be included that can influence or may be part of the structure of reticuloplasmin retention signals. In various aspects, a sequence may be included in a chimeric protease or in a chimeric substrate that promotes retention of the protein or peptide in the ER by affecting one or more of the following mechanisms: sorting of exported protein, retention of residents, and/or retrieval of escapees.

HDEL (SEQ ID NO:6) sequences are further described in Denecke et al. (1992). In some embodiments, an ER targeting sequence or ER retention sequence of Copic et al. (2009) may be used. In some embodiments, an ER-targeting sequence, such as the cytoplasmic KKXX (SEQ ID NO:27) or RR of Teasdale and Jackson (1996), may be used. The ER-targeting sequence may be a Kar2p retention mutant, e.g., as described in Copic et al. (2009). In some embodiments, the C-terminal sequence -VEKPFAIAKE (SEQ ID NO:28) described in Arber et al. (1992), may be used to promote localization to a subcompartment of the ER. Each of the foregoing references is incorporated by reference in its entirety.

Epitope Tag Sequences

A construct of the present invention may comprise one, two, or more epitope tag or immunotag sequences conjugated to or expressed as a fusion protein with the substrate target in or on the surface of a cell. It is anticipated that virtually any epitope tag may be used in various embodiments of the present invention. For example, epitope tags that may be included in a peptide or encoded by a nucleic acid of the present invention include, e.g., FLAG®, 6xHis, hemagglutinin (HA), HIS, c-Myc, VSV-G, V5 HSV, and any peptide sequence for which a monoclonal antibody is available. Antibodies that selectively bind one, two, or more of the epitope tag sequences may be used to detect the presence or absence of the epitope tag(s). In some embodiments, the antibodies are labeled with a dye, such as a fluorophore, and used for cell sorting. As would be appreciated by one of skill in the art, a wide variety of antibodies that selectively recognize an epitope tag and are labeled with a fluorophore are commercially available. Antibodies that selectively bind different epitope tags may be labeled with different fluorophores; in this way, cells may be separated or purified based on the presence or absence of one, two, three, or more fluorescent signals, e.g., using ratiometric FACS.

Many different epitope tags have been engineered into recombinant proteins. These include FLAG®, HA, HIS, c-Myc, VSV-G, V5, and HSV. Select epitope tags that may be used with the present invention are listed below.

TABLE 1

Select Epitope Tag Sequences

| Tag | Sequence | SEQ ID NO: |
|---|---|---|
| HIS | HHHHHH | SEQ ID NO: 24 |
| c-MYC | EQKLISEEDL | SEQ ID NO: 29 |
| HA | YPYDVPDYA | SEQ ID NO: 30 |
| VSV-G | YTDIEMNRLGK | SEQ ID NO: 31 |
| HSV | QPELAPEDPED | SEQ ID NO: 32 |
| V5 | GKPIPNPLLGLDST | SEQ ID NO: 33 |
| FLAG | DYKDDDDK | SEQ ID NO: 34 |

Cell Surface Display Sequence

The construct may comprise a sequence for expression on the cell surface. For example, after Golgi-derived vesicle to plasma membrane fusion occurs where the vesicle contains a substrate (containing a ER targeting sequence and an ER retention sequence), a cell-surface display sequence may be used to retain an amino acid (e.g., comprising one or more cleaved or uncleaved substrate sequences) on the surface of a eukaryotic cell, such as, e.g., a yeast cell.

In some embodiments, an Aga2p sequence can be used to display an amino acid sequence, such as a cleaved or uncleaved substrate amino acid sequence, on the surface of a eukaryotic cell, such as a yeast. For example, yeast cells can display a substrate from a randomized library extracellularly as a fusion to the Aga2p cell surface mating factor, which is covalently bound to the Aga1p mating factor via disulfide bonds (e.g., see FIG. 1). Expression of a fusion construct comprising Aga2p on the surface of yeast. Aga2p is an adhesin protein that is involved in agglutinin interaction mediated by Aga1p-Aga2p complexes and Sag1p (Huang et al., 2009), and Aga2p may be used for extracellular expression of a fusion protein in yeast (e.g., Kim et al., 2010; Boder and Wittrup, 1997). The Aga2p approach for expression of fusion proteins on the surface of yeast may be used for expression of a wide variety of proteins (Gai et al., 2007).

In other embodiments, an amino acid sequence, such as a cleaved or uncleaved substrate, may be displayed on the cell surface of a cell, such as a yeast using a glycosylphosphatidylinositol (GPI) anchor attachment signal sequence.

A mammalian mannosetypeMan5GlcNAc2 N-linked glycans may also be used to display a substrate. For example, a glycoengineered *Pichia pastoris* host strain that is genetically modified to secrete glycoproteins may be particularly useful for displaying a glycoprotein via this method as described, e.g., in Lin et al. (2011). This surface display method may use a linker (e.g., a pair of coiled-coil peptides) while using a GPI-anchored cell surface protein as an anchoring domain, such as, e.g., the *Saccharomyces cerevisiae* Sed1p GPI-anchored cell surface protein.

A self-assembled amyloid-like oligomeric-cohesin scaffoldin may be used for protein display on a yeast, such as, e.g., *Saccharomyces cerevisiae*. For example, the cellulosomal scaffolding protein cohesin and its upstream hydrophilic domain (HD) may be genetically fused with the yeast Ure2p N-terminal fibrillogenic domain consisting of residues 1 to 80

(Ure2p1-80). The resulting Ure2p1-80-HD-cohesin fusion protein may be expressed in *Escherichia coli* to produce self-assembled supramolecular nanofibrils that can serve as a protein scaffold. The excess cohesin units on the nanofibrils provide ample sites for binding to dockerin fusion protein, such as a dockerin-substrate fusion protein. Self-assembled supramolecular cohesin nanofibrils created by fusion with the yeast Ure2p fibrillogenic domain can provide a protein scaffold that can be effectively used for yeast cell surface display. Related methods are described in additional detail in Han et al. (2012).

In some embodiments, the construct may comprise an Aga2p sequence. The Aga2p yeast display system (Boder and Wittrup, 1997) has been previously characterized and may be used in various aspects of the present invention. Non-limiting examples of proteins that may be used as cell-surface proteins are described in Chen et al. (2011); Lee et al. (2011); Lin et al. (2012); Han et al. (2012); Gai et al. (2007); and article in press as: Gera et al. (2012), each of which are incorporated by reference in their entirety.

Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques. In certain preferred embodiments, the vector can express a nucleic acid sequence in a eukaryotic cell, such as, e.g., a yeast cell.

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well, such as those described herein.

An expression vector may comprise, for example, one or two or more promoters, enhancers, initiation signals, internal ribosome binding sites, multiple cloning site (MCS), RNA splicing sites, termination signals, polyadenylation signals, origins of replication (often termed "ori"), or selectable or screenable markers.

IV. EXPRESSION IN EUKARYOTIC CELLS

In certain aspects of the present invention, a protease and protease substrate may be expressed in eukaryotic cells. Cells that may be used with the present invention include, e.g., yeast, mammalian cells, insect cells, stem cells, human cells, primate cells, induced pluripotent stem cells, cancerous cells, and embryonic cell lines (e.g., HEK 293 cells, etc.). In certain preferred examples, yeast cells are used. It is anticipated that, in various embodiments, virtually any cell that contains an endoplasmic reticulum (ER) may be used to selectively target a protease and a substrate to the ER of the cell.

Using eukaryotic cells, such as yeast, can offer significant advantages over using bacteria. Building upon previous experience with *E. coli*-based protease engineering systems (Varadarajan et al., 2008) as well as yeast surface expression (Boder and Wittrup, 1997), the YESS approach uses eukaryotic cells and thus can offer several potential advantages for protease engineering. For example, the eukaryotic expression machinery in yeast can be more compatible with mammalian proteases, especially human proteases, as compared with bacteria, such as *E. coli*.

In some embodiments, yeast cells are used for selection of a protease. Yeast cells may in some embodiments be advantageously used since, e.g., they are capable of dividing quickly and are relatively robust and allow for a reasonably simple culture. Yeast cell lines that may be used with the present invention include, e.g., GS115 cells, INVSc1 cells, KM71H cells, SMD1168 cells, SMD1168H cells, and X-33 cells. It is anticipated that virtually any strain of yeast may be used with the present invention. In some embodiments the yeast may be, e.g., *Saccharomyces cerevisiae* or *Pichia pastoris*. The yeast may be an Ascomycota, such as a Saccharomycotina (referred to as "true yeasts"), or a Taphrinomycotina, such as Schizosaccharomycetales (the "fission yeasts").

Various insect cell lines may be used with the present invention. For example, insect cells that may be used with the present invention include, e.g., *Drosophila* cells, Sf9 cells, and Sf21 cells.

Mammalian cell lines that may be used with the present invention include, e.g., HEK 293 cells, CHO cells, 3T3 cells, BHK cells, CV1 cells, Jurkat cells, and HeLa cells. In some embodiments, a human cell line may be used.

V. CELL SORTING

Cells may be sorted based on the presence of one or more sequences on the surface of the cell. For example, cells may be sorted using fluorescence-activated cell sorting (FACS) or magnetic-activated cell sorting (MACS).

Subsequent to cell sorting, the specific protease produced by a yeast may be determined by genotyping nucleic acids from a colony of the yeast. A variety of known methods may be used for nucleotide sequencing. Virtually any sequencing method, such as, for example, traditional methods of sequencing or next-generation sequencing methods, may be used to determine one or more of the proteases expressed in a cell. In some embodiments, the nucleotide sequencing can be determined, e.g., by pyrosequencing or by chain termination sequencing.

Magnetic-Activated Cell Sorting (MACS)

Cells that selectively express a particular target sequence on the surface of the cells (e.g., due to expression of a protease that selectively cleaves a target substrate) may be isolated from other cells using a magnetic-activated cell sorter (MACS). MACS typically utilizes an antibody (e.g., an antibody that selectively binds an epitope tag sequence located within an expressed protein or peptide), in combination with magnetic beads to separate cells over a column. MACS may, in certain embodiments, be relatively gentle on cells and favorably affect cell viability and integrity of certain mammalian cell lines as compared to FACS.

Various MACS products are commercially available, including MACS MicroBeads™ columns or AutoMACS™ (Miltenyi Biotec, Calif., USA), and may be used according to the manufacturer's instructions. PBS/0.5% BSA (without EDTA) may used as the buffer for cell isolation. In some experiments, a Dead Cell Removal Kit (Miltenyi Biotec) may be used to remove dead cells prior to isolation of cells that express a cleaved target sequence. Repeated MACS columns may be used if necessary.

Fluorescence-Activated Cell Sorting (FACS)

Fluorescence-activated cell sorting (FACS) may also be used to separate cells that express a particular target sequence, e.g., that has been cleaved by a protease. FACS utilizes the degree of fluorescence exhibited by a cell to separate cells. In certain embodiments, one, two, or more anti-epitope tag antibodies comprising different fluorescent labels may be used to separate or purify a cell, such as a yeast cell, that expresses a cleaved or uncleaved substrate on the surface of the cell (indicating the presence of a protease with a particular specificity, activity, or potency).

In some embodiments, FACS screening or other automated flow cytometric techniques may be used for the efficient isolation of a eukaryotic cell (e.g., a yeast cell) comprising a protease that exhibits a desired specificity, potency, or efficiency. Instruments for carrying out flow cytometry are known to those of skill in the art and are commercially available to the public. Examples of such instruments include FACStar™ Plus, FACScan™, and FACSort™ instruments from Becton Dickinson (Foster City, Calif.), Epics C from Coulter Epics Division (Hialeah, FA), and MOFLO™ from Cytomation (Colorado Springs, Colo.).

FACS may be used for sorting of cells. In various embodiments, the presence or absence of 1, 2, or more antibodies, which recognize 1, 2, or more epitope tags on the surface of a cell, reflects the activity of a protease. For example, the absence of a signal may indicate undesired activity of a protease, no activity of a protease, or desired activity of a protease. FACS may also be used to separate cells that have been transformed with a desired construct from cells that do not contain or have not been transformed with a desired construct.

Flow cytometric techniques in general involve the separation of cells or other particles in a liquid sample. Typically, the purpose of flow cytometry is to analyze the separated particles for one or more characteristics, such as, e.g., presence of a labeled ligand or other molecule. FACS generally involves the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparatuses permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls.

FACS is described further, e.g., in U.S. Pat. Nos. 3,826,364; 4,284,412; 4,989,977; 4,498,766; 5,478,722; 4,857,451; 4,774,189; 4,767,206; 4,714,682; 5,160,974; and 4,661,913, each of which are specifically incorporated herein by reference.

In some embodiments, flow cytometry can be used repeatedly during multiple rounds of screening that are carried out sequentially. Cells may be isolated from an initial round of sorting and immediately reintroduced into the flow cytometer and screened again to improve the stringency of the screen. In some embodiments, non-viable cells can be advantageously recovered or separated using flow cytometry. Since flow cytometry generally involves a particle sorting technology, the ability of a cell to grow or propagate is not necessary in various embodiments of the present invention. Techniques for the recovery of nucleic acids from such non-viable cells are well known in the art and may include, for example, use of template-dependent amplification techniques, including PCR.

Bioreactors and Robotic Automation

One or more steps for the culture or separation of cells may be automated. Automating a process using robotic or other automation can allow for more efficient and economical methods for the production, culture, and differentiation of cells. For example, robotic automation may be utilized in conjunction with one or more of the culture of stem cells, passaging, addition of media, and separation of cell type, e.g., using MACS or FACS.

A bioreactor may also be used in conjunction with the present invention to culture or maintain cells. Bioreactors provide the advantage of allowing for the "scaling up" of a process in order to produce an increased amount of cells. Various bioreactors may be used with the present invention, including batch bioreactors, fed batch bioreactors, continuous bioreactors (e.g., a continuous stirred-tank reactor model), and/or a chemostat.

VI. PHARMACEUTICAL PREPARATIONS

In select embodiments, it is contemplated that a protease of the present invention may be comprised in a pharmaceutical composition and administered to a subject to treat a disease. The protease may, in some embodiments, be a modified or mutated rTPA protease.

The phrases "pharmaceutical," "pharmaceutically acceptable," or "pharmacologically acceptable" refers to molecular entities and compositions that do not produce an adverse, allergic, or other untoward reaction when administered to an animal, such as, for example, a human, as appropriate. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington: The Science and Practice of Pharmacy, 21st edition, Pharmaceutical Press, 2011, incorporated herein by reference). Except insofar as any conventional carrier is incompatible with the active ingredient, its use in the compositions of the present invention is contemplated.

A person having ordinary skill in the medical arts will appreciate that the actual dosage amount of a pharmaceutical composition comprising a protease administered to an animal or human patient can be determined by physical and physiological factors, such as body weight, severity of condition, the type of disease being treated, previous or concurrent therapeutic interventions, idiopathy of the patient, and on the route of administration. The practitioner responsible for administration will, in any event, determine the concentration of active ingredient(s) in a composition and appropriate dose(s) for the individual subject.

A pharmaceutical composition of the present invention may comprise different types of carriers depending on whether it is to be administered in solid, liquid, or aerosol form, and whether it needs to be sterile for such routes of administration as injection. A pharmaceutical composition disclosed herein can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctivally, intravesicularlly, mucosally, intrapericardially, intraumbilically, intraocularly, orally, topically, locally, and by inhalation, injection, infusion, continuous infusion, lavage, and localized perfusion. A pharmaceutical composition may also be administered to a subject via a catheter, in cremes, in lipid compositions, by ballistic particulate delivery, or by other method or any combination of the forgoing as would be known to one of ordinary skill in the art (see, for example, Remington: The Science and Practice of Pharmacy, 21$^{st}$ Ed. Lippincott Williams and Wilkins, 2005, incorporated herein by reference).

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax, or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

In some embodiments, a pharmaceutical composition may comprise, e.g., a lipid microsphere, a lipid nanoparticle, an ethosome, a liposome, a niosome, a phospholipid, a sphingosome, a surfactant, a transferosome, an emulsion, or a combination thereof. The formation and use of liposomes and other lipid nano- and microcarrier formulations is generally known to those of ordinary skill in the art, and the use of liposomes, microparticles, nanocapsules, and the like have gained widespread use in delivery of therapeutics (e.g., U.S. Pat. No. 5,741,516, specifically incorporated herein in its entirety by reference). Numerous methods of liposome and liposome-like preparations as potential drug carriers, including encapsulation of peptides, have been reviewed (U.S. Pat. Nos. 5,567,434; 5,552,157; 5,565,213; 5,738,868; and 5,795,587, each of which is specifically incorporated in its entirety by reference).

A protease may, in certain instances, be formulated into a composition in a neutral or salt form. Pharmaceutically acceptable salts include the acid addition salts (formed with the free amino groups of the protein), which are formed with inorganic acids, such as, for example, hydrochloric or phosphoric acids, or such organic acids as acetic, oxalic, tartaric, mandelic, and the like. Salts formed with the free carboxyl groups can also be derived from inorganic bases, such as, for example, sodium, potassium, ammonium, calcium, or ferric hydroxides, and such organic bases as isopropylamine, trimethylamine, histidine, procaine, and the like.

In any case, the composition may comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal, or combinations thereof.

Sterile injectable solutions may be prepared by incorporating the active proteases in the required amount in the appropriate solvent with various amounts of the other ingredients enumerated above, as required, utilizing filtered sterilization. Generally, dispersions may be prepared by incorporating the various sterilized active ingredients into a sterile vehicle that contains the basic dispersion medium and/or the other ingredients. In the case of sterile powders for the preparation of sterile injectable solutions, suspensions, or emulsion, the preferred methods of preparation are vacuum-drying or freeze-drying techniques, which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

In particular embodiments, prolonged absorption of an injectable composition can be brought about by the use in the compositions of agents delaying absorption, such as, for example, aluminum monostearate, gelatin, or combinations thereof.

VII. MODIFIED PROTEASES

Some embodiments concern modified proteins and polypeptides, particularly a modified protein or polypeptide that exhibits at least one functional activity that is comparable to the unmodified version, yet the modified protein or polypeptide possesses an additional advantage over the unmodified version, such as altering protease specificity, potency, or efficiency, decreasing degradation in the body, reduced antigenicity, easier or cheaper to produce, eliciting fewer side effects, and/or having better or longer efficacy or bioavailability. Thus, when the present application refers to the function or activity of "modified protein" or a "modified polypeptide" one of ordinary skill in the art would understand that this includes, for example, a protein or polypeptide that 1) performs at least one of the same activities or has at least one of the same specificities as the unmodified protein or polypeptide, but that may have a different level of another activity or specificity; and 2) possesses an additional advantage over the unmodified protein or polypeptide. Determination of activity may be achieved using assays familiar to those of skill in the art, particularly with respect to the protein's activity, and may include for comparison purposes, for example, the use of native and/or recombinant versions of either the modified or unmodified protein or polypeptide. It is specifically contemplated that embodiments concerning a "modified protein" may be implemented with respect to a "modified polypeptide," and vice versa. In addition to the modified proteins and polypeptides discussed herein, embodiments may involve domains, polypeptides, and proteins described in WO 2008/137475, which is hereby specifically incorporated by reference.

Aspects of the present invention relate to one or more of the below modified proteases, e.g., a TEV protease as shown Table 2, Table 3, Table 4, and/or Table 5. These modified proteases are further discussed in the examples below. In some embodiments, a modified TEV protease may comprise one or more of the mutations listed below.

TABLE 2

Engineered TEV-P variants obtained after sorting the S1 pocket library

| Variant Number | (P1) | T146 | D148 | H167 | S170 | Other mutations |
|---|---|---|---|---|---|---|
| TEV-PE1 | E | T | K | H | S | |
| TEV-PH1 | H | A | A | H | S | V228A |
| TEV-PL1 | L | C | A | V | T | T173N |
| TEV-PN1 | N | A | S | H | T | |
| TEV-PP1 | P | T | D | Y | L | G213C |
| TEV-PT1 | T | V | R | Q | A | T113A, T173A |

TABLE 3

Evolved TEV-P variants obtained after the cell sorting of the S1 pocket library and the error-prone PCR libraries

| Variant Number | (P1) | T146 | D148 | H167 | S170 | Other mutations |
|---|---|---|---|---|---|---|
| TEV-PE1 | E | T | K | H | S | |
| TEV-PE2 | E | T | P | H | R | |
| TEV-PE3 | E | T | R | H | S | |
| TEV-PE4 | E | T | R | H | A | T22A, L56W, F172L, T173A, Q197R |
| TEV-PE5 | E | T | R | H | A | V125A, T173A, N174H |
| TEV-PE6 | E | T | R | H | A | K65R, T173A, N177K, F186L M218I |
| TEV-PE7 | E | T | R | H | A | P92L, R108H, M121L, S122P, T173A, N177K |
| TEV-PE8 | E | T | R | H | S | N171S |
| TEV-PE9 | E | T | R | H | S | N177K |
| TEV-PE10 | E | T | R | H | S | S120R, T173A, N177K, M218I |
| TEV-PE11 | E | A | P | H | A | T173A, N177K |
| TEV-PE12 | E | A | P | H | A | T173A, N177K, V199D |
| TEV-PE13 | E | A | P | H | A | T173A, N177K, Q196R |
| TEV-PE14 | E | A | P | H | A | K65E, T173A, N177K, F179L |
| TEV-PE15 | E | A | P | H | A | N12D, I163V, T173A, N177K, M218I |
| TEV-PE16 | E | A | P | H | A | M124I, T173A, N177K, K184R, P221S |
| TEV-PE17 | E | A | P | H | A | C110R, R159G, T173A, N177K, N192D, E223G |
| TEV-PH1 | H | A | A | H | S | V228A |
| TEV-PH2 | H | A | A | H | T | |
| TEV-PH3 | H | A | A | H | T | R203Q |
| TEV-PH4 | H | A | S | H | T | |
| TEV-PH5 | H | A | P | H | A | |
| TEV-PH6 | H | A | P | H | A | E106G, T173A |
| TEV-PH7 | H | A | P | H | A | T173A, M218I |
| TEV-PH8 | H | A | P | H | S | |
| TEV-PH9 | H | A | P | H | S | K89R, T173A |
| TEV-PH10 | H | A | P | H | S | Q96R |
| TEV-PH11 | H | A | P | H | T | |
| TEV-PH12 | H | C | P | H | T | |
| TEV-PH13 | H | C | Q | H | S | N171D |
| TEV-PH14 | H | V | A | H | S | |
| TEV-PH15 | H | V | P | H | A | N171S |
| TEV-PH16 | H | V | P | H | S | T128S, D136G |
| TEV-PH17 | H | V | P | H | S | D136G |
| TEV-PH18 | H | V | P | H | T | K147T |
| TEV-PH19 | H | V | R | H | S | |
| TEV-PH20 | H | A | P | H | A | T173A |
| TEV-PH21 | H | A | P | H | A | T17A, S153C, S168T, T173A |
| TEV-PH22 | H | A | P | H | A | Y11F, C110R, I144T, T173A, F186L, M218I |
| TEV-PL1 | L | C | A | V | T | T173N |
| TEV-PL2 | L | C | A | V | T | T173N, N192S |
| TEV-PL3 | L | C | P | V | T | T17A, T173N, K184R |
| TEV-PL4 | L | C | R | V | T | T70M, T173N |
| TEV-PL5 | L | Q | R | V | T | Q58K, K99E, T173N |
| TEV-PN1 | N | A | S | H | T | |
| TEV-PN2 | N | V | E | H | T | Q104R, T173A |
| TEV-PN3 | N | V | P | H | S | D136G |
| TEV-PN4 | N | V | P | H | S | P39H, D136G |
| TEV-PN5 | N | V | P | H | A | N171S |
| TEV-PN6 | N | V | R | H | S | |
| TEV-PP1 | P | T | D | Y | L | G213C |
| TEV-PT1 | T | V | R | Q | A | T113A, T173A |

Variants TEV-PE4, to TEV-PE17, and TEV-PH20 to TEV-PH21 were obtained from the error-prone PCR libraries.

TABLE 4

Engineered TEV-P variants obtained after sorting the error-prone libraries

| Variant Number | (P1) | T146 | D148 | H167 | S170 | Other mutations |
|---|---|---|---|---|---|---|
| TEV-PE10 | E | T | R | H | S | S120R, T173A, N177K, M218I |
| TEV-PH21 | H | A | P | H | A | T17A, S153C, S168T, T173A |

TABLE 5

Engineered TEV protease variants obtained after the cell sorting of the error-prone PCR libraries

| Number | Variant (P1) | T146 | D148 | H167 | S170 | Other mutations |
|---|---|---|---|---|---|---|
| TEV-PE4 | E | T | R | H | A | T22A, L56W, F172L, T173A, Q197R |
| TEV-PE5 | E | T | R | H | A | V125A, T173A, N174H |
| TEV-PE6 | E | T | R | H | A | K65R, T173A, N177K, F186L, M218I |
| TEV-PE7 | E | T | R | H | A | P92L, R108H, M121L, S122P, T173A, N177K |
| TEV-PE8 | E | T | R | H | S | N171S |
| TEV-PE9 | E | T | R | H | S | N177K |
| TEV-PE10 | E | T | R | H | S | S120R, T173A, N177K, M218I |
| TEV-PE11 | E | A | P | H | A | T173A, N177K |
| TEV-PE12 | E | A | P | H | A | T173A, N177K, V199D |
| TEV-PE13 | E | A | P | H | A | T173A, N177K, Q196R |
| TEV-PE14 | E | A | P | H | A | K65E, T173A, N177K, F179L |
| TEV-PE15 | E | A | P | H | A | N12D, I163V, T173A, N177K, M218I |
| TEV-PE16 | E | A | P | H | A | M124I, T173A, N177K, K184R, P221S |
| TEV-PE17 | E | A | P | H | A | C110R, R159G, T173A, N177K, N192D, E223G |
| TEV-PH20 | H | A | P | H | A | T173A |
| TEV-PH21 | H | A | P | H | A | T17A, S153C, S168T, T173A |
| TEV-PH22 | H | A | P | H | A | Y11F, C110R, I144T, T173A, F186L, M218I |

Modified proteins may possess deletions and/or substitutions of amino acids; thus, a protein with a deletion, a protein with a substitution, and a protein with a deletion and a substitution are modified proteins. In some embodiments these modified proteins may further include insertions or added amino acids, such as with fusion proteins or proteins with linkers, for example. A "modified deleted protein" lacks one or more residues of the native protein, but possesses the specificity and/or activity of the native protein. A "modified deleted protein" may also have reduced immunogenicity or antigenicity. An example of a modified deleted protein is one that has an amino acid residue deleted from at least one antigenic region, that is, a region of the protein determined to be antigenic in a particular organism, such as the type of organism that may be administered the modified protein.

Substitutional or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a native polypeptide are included, provided the biological activity of the protein is maintained. A modified protein may be biologically functionally equivalent to its native counterpart.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure with or without appreciable loss of interactive binding or enzymatic capacity with structures, such as, for example, binding sites to substrate molecules. Since it is the interactive capacity and nature of a protein that defines that protein's biological functional activity, certain amino acid substitutions can be made in a protein sequence and in its underlying DNA coding sequence, and nevertheless produce a protein with like properties. It is thus contemplated by the inventors that various changes may be made in the DNA sequences of genes without appreciable loss of their biological utility or activity, as discussed below. A proteinaceous molecule has "homology" or is considered "homologous" to a second proteinaceous molecule if one of the following "homology criteria" is met: 1) at least 30% of the proteinaceous molecule has sequence identity at the same positions with the second proteinaceous molecule; 2) there is some sequence identity at the same positions with the second proteinaceous molecule and at the nonidentical residues, at least 30% of them are conservative differences, as described herein, with respect to the second proteinaceous molecule; or 3) at least 30% of the proteinaceous molecule has sequence identity with the second proteinaceous molecule, but with possible gaps of nonidentical residues between identical residues. As used herein, the term "homologous" may equally apply to a region of a proteinaceous molecule, instead of the entire molecule. If the term "homology" or "homologous" is qualified by a number, for example, "50% homology" or "50% homologous," then the homology criteria, with respect to 1), 2), and 3), is adjusted from "at least 30%" to "at least 50%." Thus it is contemplated that there may be homology of at least 30%, 35%, 40%, 45%, 50%, 55%, 60%, 65%, 70%, 75%, 80%, 85%, 90%, 95%, or more between two proteinaceous molecules or portions of proteinaceous molecules.

Alternatively, a modified polypeptide may be characterized as having a certain percentage of identity to an unmodified polypeptide or to any polypeptide sequence disclosed herein, including an engineered or modified protease, such as a TEV protease. The percentage identity may be at most or at least 50%, 55%, 60%, 65%, 70%, 75%, 80%, 85%, 90%, 95%, 96%, 97%, 98%, 99%, 99.5%, 99.9%, or 100% (or any range derivable therein) between two proteinaceous molecules or portions of proteinaceous molecules. For example, a modified protease may have from 85% to 99.5% homology as compared to the wild-type protease. Generally, a modified polypeptide or modified protease will have at least one mutation, substitution mutation, addition, or deletion, as compared to the wild-type polypeptide or protease such that the amino acid sequences of the modified polypeptide or protease are not identical to the wild-type polypeptide or protease. It is contemplated that the percentage of identity discussed above may relate to a particular region of a polypeptide compared to an unmodified region of a polypeptide. In some embodiments, a modified protease or a modified protein kinase may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more mutations, substitution mutations, additions, or deletions as compared to the native or wild-type protease or kinase, respectively, but otherwise share complete amino acid sequence identity with the protease or kinase.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine, and isoleucine.

Fusion and Conjugated Proteins

A specialized kind of insertional variant is the fusion protein. This molecule generally has all or a substantial portion of the native molecule, linked at the N- or C-terminus, to all or a portion of a second polypeptide.

Embodiments also concern conjugated polypeptides, such as translated proteins, polypeptides, and peptides that are linked to at least one agent to form a modified protein or polypeptide. In order to increase the efficacy of molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety that may be detected using an assay. Non-limiting examples of reporter molecules that have been conjugated to antibodies include enzymes, radio-labels, haptens, fluorescent labels, phosphorescent molecules, chemiluminescent molecules, chromophores, luminescent molecules, photoaffinity molecules, colored particles, or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti-cellular agent, and may be termed "immunotoxins."

Amino acids, such as selectively-cleavable linkers, synthetic linkers, or other amino acid sequences, may be used to separate proteinaceous moieties.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Construction and Transformation of Yeast Vectors for Library Sorting

Figure 6:
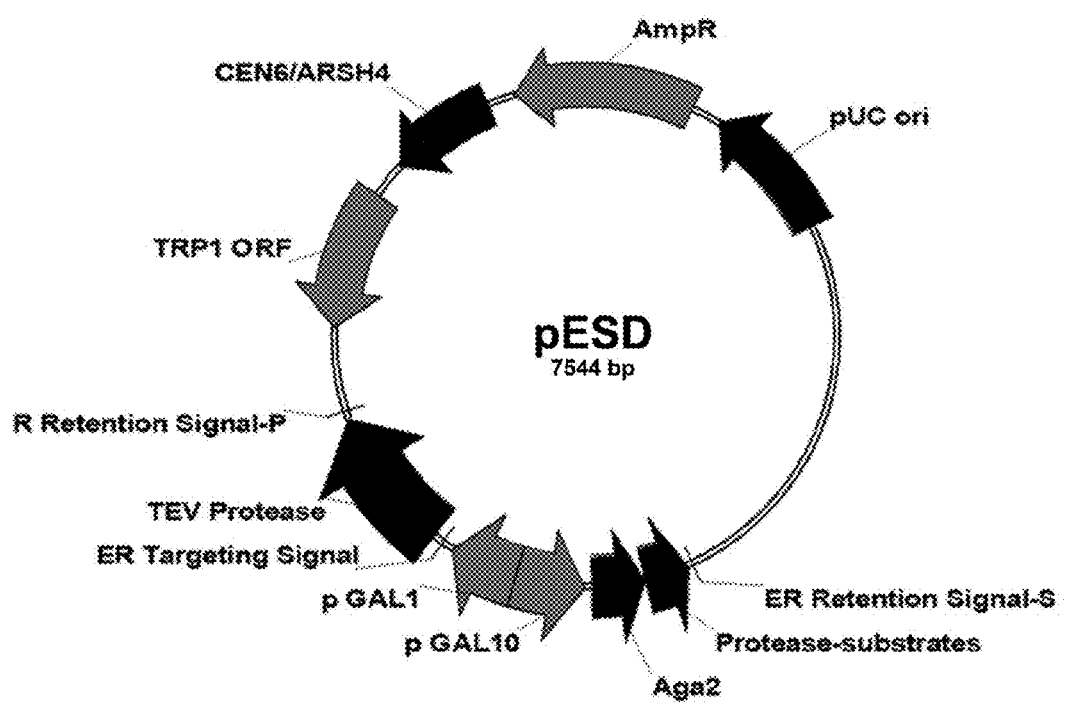
FIG. 6: Map of the vector pESD.

The pESD plasmid was constructed based on the pCTCon2 (generously contributed by Dr. Dane K. Wittrup at MIT) and the pESC-TRP vectors (Agilent Technologies, Santa Clara Calif.; generously contributed by Dr. Edward W. Marcotte at UT Austin) (FIG. 6). The GAL1/10 bidirectional promoter in the pCTCon2 plasmid was replaced by the dual GAL1-GAL10 promoter that transcribes in both directions, establishing a co-expressing system. The strength ratio of the GAL1:GAL10 in this bi-directional promoter is around 0.8:1.0 based on the company manual. The TEV-P substrate library was inserted downstream of the GAL10 promoter in the pESD vector. Under the control of the GAL10 promoter and after the Aga2 gene used for yeast surface display, a five-part cassette was cloned consisting of (1) the native substrate of TEV-P, ENLYFQS (SEQ ID NO:18); (2) a FLAG tag, DYKDDDDK (SEQ ID NO:22); (3) the designed peptide substrate library, ENLYFXS (X can be any residue) (SEQ ID NO:23); (4) a 6xHis tag; and (5) the ER retention signal peptide, FEHDEL (SEQ ID NO:4). Under the control of the GAL1 promoter, the TEV-P S1 pocket library (see below) was cloned by homologous recombination along with a designed N-terminal ER targeting signal peptide (QLLRCFSIFSVI-ASVLA, SEQ ID NO:25) and with or without a C-terminal ER retention signal peptide. EBY100 cells (URA+, leu–, trp–, *Saccharomyces cerevisiae*) were transformed with pESD (TRP+) vector by electroporation using the protocol previously described (Benatuil et al., 2010).

Construction of TEV-P P1 Pocket Library and Error-Prone Library.

A saturation mutagenesis library of TEV-P, termed the 51 pocket library, was constructed using a previously described method (Varadarajan et al., 2009b). Four residues in the 51 substrate-binding pocket—T146, D148, H167, and S170—were chosen for mutagenesis based on the known structure of TEV-P (Phan et al., 2002). Briefly, for the construction of the 51 pocket library of TEV-P, PAGE-purified primers (Primers 1-Primer 8, Table 6), which contained a randomized NNS codon (N=A, T, G, or C; S=G or C) in place of the wild-type codon at these four positions, were used to amplify the TEV-P gene by splicing overlap extension PCR (Kim et al., 2000). The PCR product was digested with KpnI and PstI, gel purified, and ligated into similarly digested vector pTrc99A-MBP. The ligation product was used to electroporate electrocompetent *E. coli* MC1061 [F⁻ Δ(ara-leu)7697 [araD139]$_{B/r}$ Δ(codB-lacI)3 galK16 galE15 λ⁻e14⁻ mcrA0 relA1 rpsL150 (strR) spoT1 mcrB1 hsdR2(r⁻m⁺)] cells, and the library was plated on selective media. Plasmid DNA was isolated from the pooled clones using a QIAprep Spin Miniprep kit (QIAGEN, Valencia, Calif., USA).

The TEV-P S1 pocket library DNA was then PCR-amplified using Primer 9 and Primer 10 (Table 6). A sequence encoding the ER retention peptide (FEHDEL (SEQ ID NO: 4)) was fused in frame to the 3' by overlap extension PCR. The library DNA was fused to a sequence encoding the Aga2 signal peptide QLLRCFSIFSVIASVLA (SEQ ID NO:25). The DNA product was inserted downstream of the GAL1 promoter in pESD vector by homologous recombination, in the *Saccharomyces cerevisiae* EBY100 strain (URA+, leu–, trp–) (Benatuil et al., 2010).

TABLE 6

Primers

| Primers | Sequences |
|---|---|
| Primer 1 | 5'-GGAAGCATTGGATTCAANNSAAGNNSGGGCAGTGTGGCAGTCC-3' (SEQ ID NO: 35) |
| Primer 2 | 5'-ATTAGTATCAACTAGAGATGGGTTCATTGTTGGTATA-3' (SEQ ID NO: 36) |
| Primer 3 | 5'-ATCTCTAGTTGATACTAATGGACTGCCACACTGCCC-3' (SEQ ID NO: 37) |
| Primer 4 | 5'-TTTGTGTTGGTGAAATTSNNTGCTGASNNTATACCAACAATGAACCC-3' (SEQ ID NO: 38) |
| Primer 5 | 5'-TTGAATCCAATGCTTCCAGAA-3' (SEQ ID NO: 39) |
| Primer 6 | 5'-AATTTCACCAACACAAACAA-3' (SEQ ID NO: 40) |
| Primer 7 | 5'-TACCATCTGCAGAGCGACGGCGACGACGATTCATGAG-3' (SEQ ID NO: 41) |
| Primer 8 | 5'-ATGGTTGGTACCGAAAATCTTTATTTTAGCGGTCATCATCATC-3' (SEQ ID NO: 42) |
| Primer 9 | 5'-CGTCAAGGAGAAAAAACCCCGGATCCGTAATACGACTCACTATAGGGCCCGGGCGTCGA CATGCAACTTTTGAGATGCTTCAGTATTTTCAGCGTCATCGCCAGTGTGCTGGCCAGCTTG TTTAAGGGGCCGCGTG-3' (SEQ ID NO: 43) |
| Primer 10 | 5'-GTACAGTGGGAACAAAGTCGATTTTGTTACATCTACACTGTTGTTATCAGATCTCGAGCG GTACCTTACTCATTACAATTCGTCGTGTTCGAAACTACCCAAGTCCTCTTCAGAAATAAGC TTTTGTTCGGATCCATTCATGAGTTGAGTCGCTTCC-3' (SEQ ID NO: 44) |
| Primer 11 | 5'-ATGGCTGGCCCAGCCGGCCAGCTTGTTTAAGGGGCCGCG-3' (SEQ ID NO: 45) |
| Primer 12 | 5'-GTCCATGGCCCCCGAGGCCTTAATTCATGAGTTGAGTCGCTTCCTTAAC-3' (SEQ ID NO: 46) |
| Primer 13 | 5'-GTACAGTGGGAACAAAGTCGATTTTGTTACATCTACACTGTTGTTATCAGATCTCGAGCG GTACCTTACTCATTAATTCATGAGTTGAGTCGCTTCC-3' (SEQ ID NO: 47) |
| Primer 14 | 5'-GAGCTCACAATTCGTCGTGTTCGAAACTACCATGATGATGATGATGATGACTGCCAGASN NGAAATACAAATTTTCACTGCCTTTATCGTCGTCATCTTTATAATC-3' (SEQ ID NO: 48) |
| Primer 15 | 5'-CGAATTCAACCCTCACTAAAGGGCGGCCGCACTAGTATCGATG-3' (SEQ ID NO: 49) |

Error-Prone PCR Library Construction.

Random mutagenesis was performed by error-prone PCR amplification (Drummond et al., 2005) using the selected TEV-P variants as templates and Primers 11 and 12 (Table 6). The error-prone PCR libraries were then constructed in the pMOPAC12 vector (Jung et al., 2010) for library confirmation and storage. The error-prone PCR libraries were amplified for yeast transformation using Primer 9 and Primer 13 (Table 6). The ER retention peptide was removed during the PCR amplification process. The amplified library was then integrated into the pESD vector during yeast transformation by homologous recombination.

Substrate Library Construction.

For the construction of the TEV-P substrate library, PAGE-purified primers (Primer 14 and Primer 15, Table 6), which contained a randomized NNS codon correspondent to the residue Q in the wild-type TEV-P substrate (ENLYFQS, SEQ ID NO:18), were used to amplify the whole substrate fusion gene. The whole substrate fusion gene is comprised of Aga2, selection and counter selection substrate sequences, multiple intervening epitope tag sequences, and a C-terminal ER retention sequence. The PCR products were then inserted downstream of the GAL10 promoter in the pESD vector by homologous recombination, in the *Saccharomyces cerevisiae* EBY100 strain (URA+, leu−, trp−) (Benatuil et al., 2010). The substrate library was labeled with anti-6xHis-FITC antibody and pre-sorted to remove any undesired mutations, including possible stop codons or shifted reading frames.

Library Sorting with Flow Cytometry.

The constructed libraries were integrated into corresponding pESD vectors during the transformation into yeast cells EBY100 by electroporation (Benatuil et al., 2010). The cells were grown and induced as previously described with slight modification (Chao et al., 2006). The yeast cells were grown to an $OD_{600}$ of 2.0-3.0 in 1 L YNB-CAA+glucose medium, followed by induction through switching the medium to YNB-CAA+galactose medium with a final $OD_{600}$ of 0.5. The cells were then grown at 30° C. overnight with shaking. The induced cells ($2-5\times10^8$ cells, which is around 10-fold larger than the library sizes) were washed and then labeled with anti-FLAG-PE antibody (ProZyme, Hayward, Calif., USA) followed by anti-6xHis-FITC antibody (Genscript, Piscataway, N.J., USA). During the antibody labeling steps, the cells were resuspended into 1×PBS solution containing 0.5% BSA with a final cell density of $10^5$ cells/μL. The amounts of antibody used for labeling were 0.02 μg/μL and 0.01 μg/μL for anti-FLAG-PE antibody and anti-6xHis-FITC antibody, respectively. The antibody-labeled cells were washed and resuspended in 1×PBS buffer and analyzed by BD Biosciences FACS Aria II flow cytometer (BD Biosciences San Jose, Calif., USA). Library sorting was performed using gates set on FSC/SSC and 575/30 nm as well as 510/20 nm emission filters. A total of about $2\times10^8$ cells were screened. To avoid bacterial contamination, penicillin and streptomycin were added into the growth and inducing media, with the final concentration of 100 units and 100 μg/mL, respectively. After 4-5 rounds of cell sorting and resorting, the cells were plated on selective medium plates, and individual colonies were re-analyzed and confirmed by flow cytometry. The DNA was extracted from the confirmed yeast single colonies, then transformed into *E. coli* and sequenced to obtain the mutated gene sequence information.

In similar steps, human AblTK expressing cells were labeled using Alexa Fluor® 647 anti-Phosphotyrosine antibody (BioLegend, San Diego, Calif., USA) and anti-6xHis-FITC antibody (Genscript, Piscataway, N.J., USA) with final concentrations of 0.03 μg/μL and 0.01 μg/μL, respectively. The gates were set on 660/20 nm emission filter for Alexa Fluor® 647 as well as 510/20 nm emission filter for FITC in the BD Biosciences FACS Aria II flow cytometer (BD Biosciences San Jose, Calif., USA).

Purification of TEV Proteases and their Protein Substrates.

The wild-type TEV-P and its variants were expressed and purified as previously described (Tropea et al., 2009). To monitor the cleavage of fusion proteins by TEV-P or its variants, protein substrates were constructed by anchoring the different peptide sequences between the maltose binding protein (MBP) and the glutathione-S-transferase (GST) proteins. The protein substrate Q ($ProS_Q$), protein substrate E ($ProS_E$), and protein substrate H ($ProS_H$), contained ENLYFQS (SEQ ID NO:18), ENLYFES (SEQ ID NO:1), and ENLYFHS (SEQ ID NO:2) peptide sequences, respectively, between the MBP and GST proteins. The respective fusions were designated MBP-ENLYFQS-GST (MBP-SEQ ID NO: 18-GST), MBP-ENLYFES-GST (MBP-SEQ ID NO:1-GST), and MBP-ENLYFHS-GST (MBP-SEQ ID NO:2-GST). For kinetic analysis, the different substrate peptides, including TENLYFQSGTRRW ($PepS_Q$, SEQ ID NO:8), TENLYFESGTRRW ($PepS_E$, SEQ ID NO:10), and TENLYFHSGTRRW ($PepS_H$, SEQ ID NO:9), were synthesized by and purchased from Genscript (Genscript, Piscataway, N.J., USA).

Kinetic Measurement of Wild-Type TEV-P and its Variants.

All purified enzymes were >95% pure as determined by SDS-PAGE with Coomassie staining (Tropea et al., 2009). Kinetic assays were carried out in 50 mM Tris-HCl buffer, pH 8.0, containing 1 mM EDTA and 2 μM freshly prepared DTT. Five micromolar to 6 mM substrates were incubated with 0.025-5 μM purified enzymes at 30° C. for 10 to 30 minutes. The reactions were quenched with freshly prepared 0.5% trifluoroacetic acid (TFA) followed by freezing at −80° C. All the enzymatic reactions were analyzed by HPLC on a Phenomenex $C_{18}$ reverse-phase column (Phenomenex, Torrance, Calif., USA) using an acetonitrile gradient from 15% to 90%, and a flow rate of 1 mL/min. The cleavage products were collected and confirmed by LC-MS (ESI) on a Magic 2002 instrument (Micron Bioresources, Auburn, Calif.). The product amount was calculated upon the integration area at 280 nm and fitted to nonlinear regression of the Michaelis-Menten equation using KaleidaGraph software (Synergy Software, Reading, Pa., USA).

Example 2

Protease Engineering Using Yeast ER Sequestering (YESS)

YESS Method Validation

The expression of both the protease and substrate as separate fusions allows for at least three different types of experiments using the YESS format. A single new substrate can be used as the selection substrate along with one or more counter selection substrates in the presence of a protease library in order to isolate a protease variant with a desired new sequence specificity. Alternatively, a single protease of interest can be used with a library of substrate sequences in order to profile protease cleavage positional specificity. Finally, a "library-on-library" approach can be used in which a library of proteases is expressed in conjunction with a library of substrates, potentially increasing the odds of identifying highly active/specific new engineered protease-substrate pairs.

Figure 17:
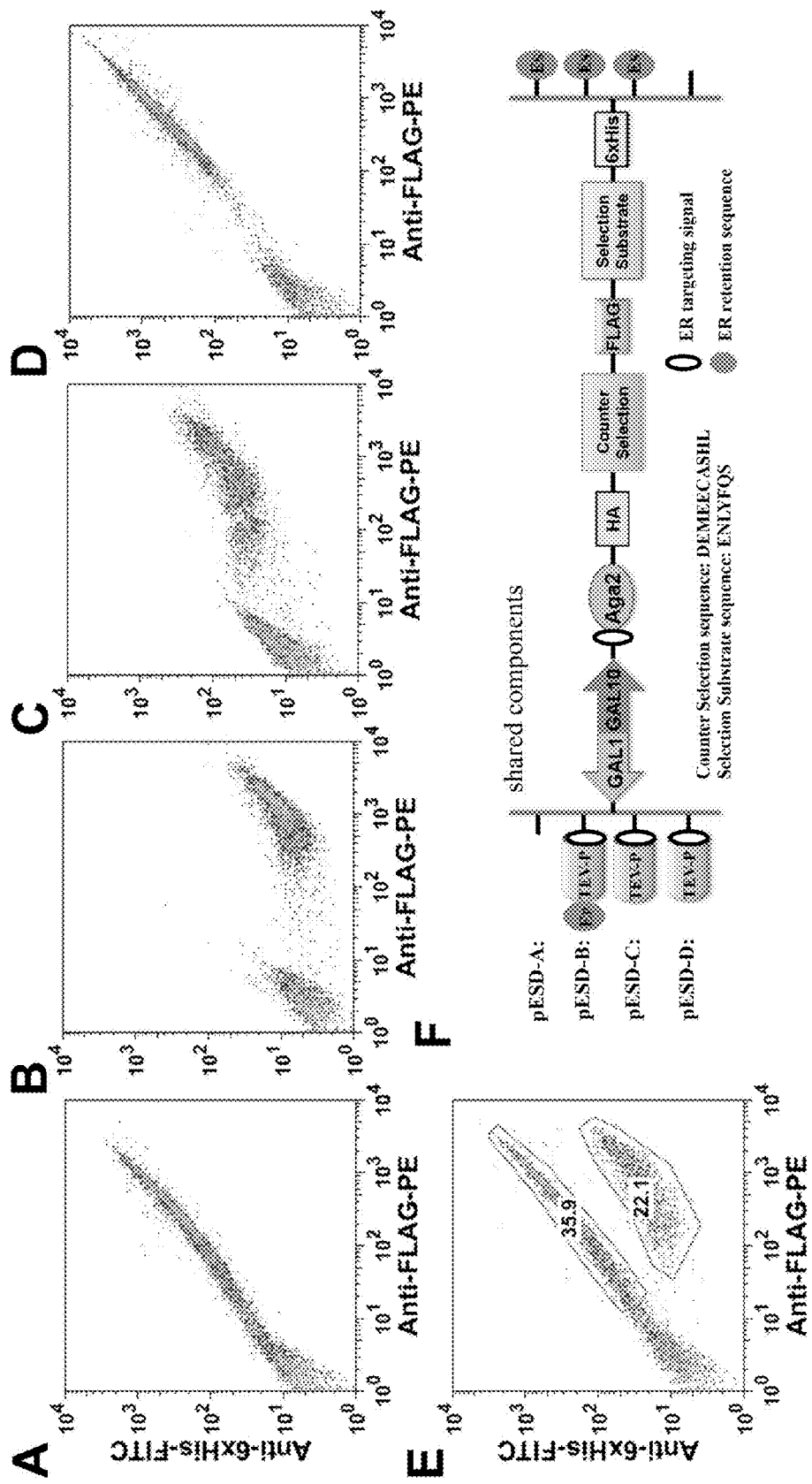
FIGS. 17A-F: Two-color FACS analysis of cells with and without ER retention signals in the substrate fusion and protease. All cells were grown, induced, antibody labeled, and analyzed under the same conditions.
Figure 18:
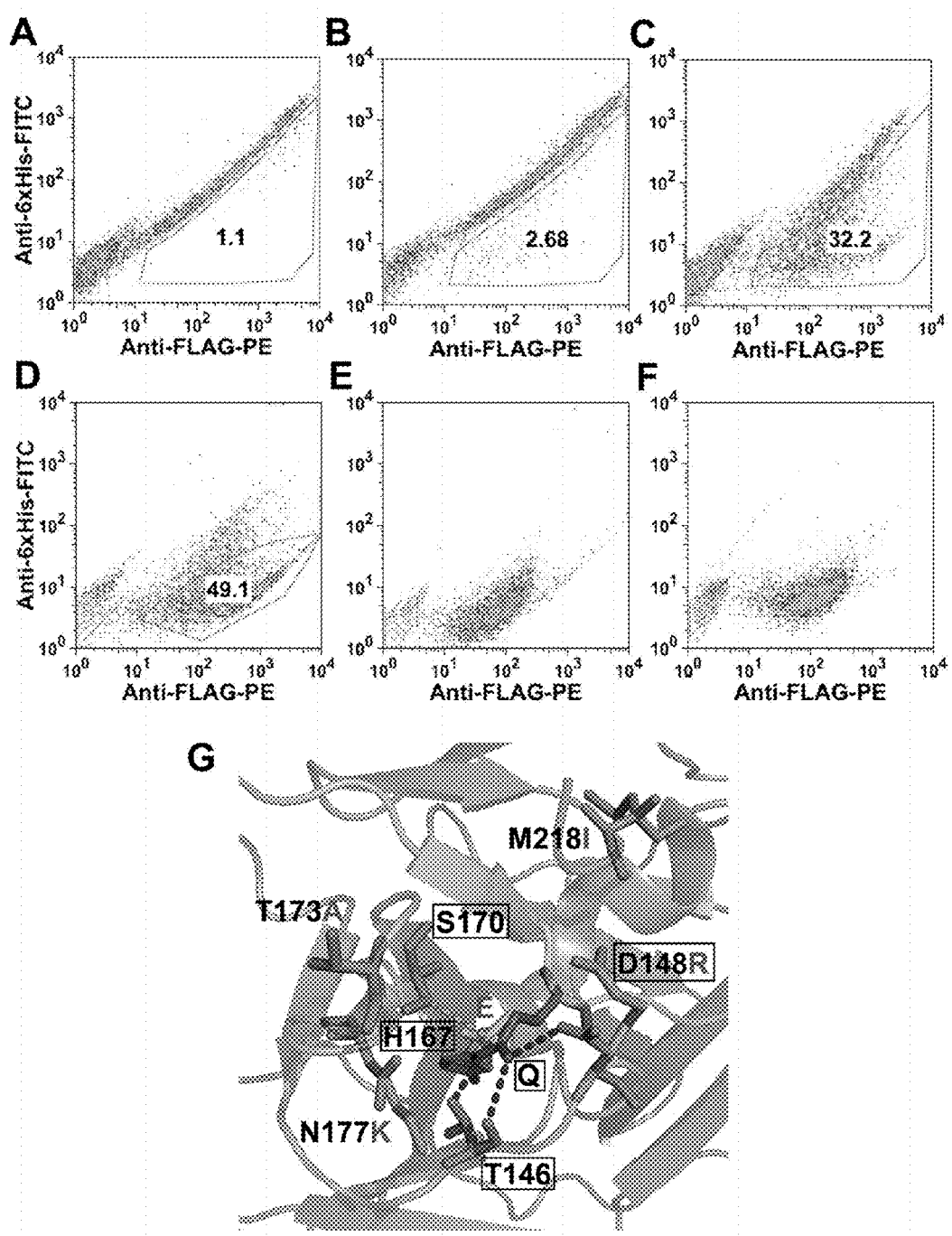
FIGS. 18A-G: FACS analysis of TEV-P S1 subsite library using the YESS system.

A number of experiments were carried out to validate the YESS system. Throughout, the TEV-P was used as a model protease due to its broad application in research and industry as well as its relatively high level of substrate specificity. The substrate construct consisted of Aga2 fused at its C-terminus to the HA epitope tag (for internal expression level calibration), a flexible linker (GGGS)4, a counter selection peptide sequence (the canonical hepatitis C virus NS4A/NS4B protease (HCV-P) substrate DEMEECASHL, SEQ ID NO:17), the FLAG epitope tag, the wild-type TEV-P preferred substrate peptide ENLYFQS (SEQ ID NO:18), the 6xHis epitope tag, and finally the ER retention signal at the C-terminus. Following induction of expression of the protease and substrate fusion constructs in media with galactose as the carbon source, the cells were incubated with the PE-labeled, anti-FLAG antibody as well as the FITC-labeled, anti-6xHis antibody. When the TEV-P was not expressed, the cells were labeled with both antibodies and hence occupy the diagonal in the two dimensional FACS plot (FIGS. 17A and F). The presence of the TEV-P anchored with a C-terminal ER retention sequence gave rise to a cell population exhibiting high PE but low FITC fluorescence, consistent with the expected selective cleavage at the ENLYFQS (SEQ ID NO:18) sequence that results in loss of the C-terminal 6xHis tag (FIG. 17B). Removal of the ER retention sequence from the C-terminus of TEV-P or from both the TEV-P and the substrate construct gave rise to markedly higher FITC (6xHis) fluorescence relative to the positive control (FIGS. 17C and D). A 1:1 mixture of positive control cells with cells lacking the TEV-P gene showed a fluorescence profile identical to the sum of the respective single cell populations (compare FIGS. 17A and B with FIG. 17E) indicating that any adventitious release of TEV-P in the culture supernatant does not lead to cleavage of the substrate construct in other cells. Further, TEV-P could not be detected in the growth medium by western blotting presumably because, if present at all, its concentration must have been below the detection limit. After single colony sequencing of enriched cells, an enrichment factor of approximately 600-fold was observed in a single round of YESS using yeast cells co-expressing TEV-P and a substrate fusion polypeptide mixed with a 1.000-fold excess of cells that either lacked protease activity or in which the selection and counter selection substrate sequences were in the wrong slots (FIGS. 2B-F).

Figure 16:
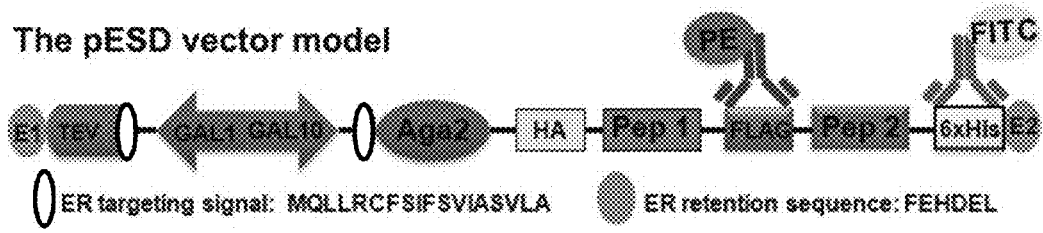
FIG. 16: Table of pESD constructs. ER signaling peptide MQLLRCFSIFSVIASVLA (SEQ ID NO:3) and ER retention sequence FEHDEL (SEQ ID NO:4) are shown in the figure. Abbreviations in the table are as follows: E1: ER retention signal at C-terminus of TEV-P; E2: ER retention signal at C-terminus of substrates Pep A: Unrelated sequence (DEMEECASHL, SEQ ID NO:17); Pep B: TEV-P native substrate (ENLYFQS, SEQ ID NO:18) Pep C: mutated TEV-P substrate (ENLYFKS, SEQ ID NO:11)

Six vectors based on the pESD plasmid were constructed to evaluate various details of ER retention effects in the YESS system (FIG. 16; FIGS. 7A-G). The construct pESD-E, in which both the TEV-P and its peptide substrates contain the C-terminal FEHDEL (SEG ID NO: 4) ER retention peptide, presented high PE but low FITC signals in the FACS analysis, indicating efficient cleavage at the peptide 2 sequence, which in this case was the TEV-P native peptide substrate (FIG. 7E). Both high PE and FITC signals were exhibited in the construct pESD-A, which is a control vector containing only the substrate construct and no TEV-P (FIG. 7A). Constructs pESD-C and pESD-D lack the ER retention signals in the protease and substrate constructs, respectively. Compared to construct pESD-E, constructs pESD-C and pESD-D have similar high PE signals but with the FITC signals exhibit intensities between those seen with constructs pESD-A and pESD-E (FIGS. 7C and D). Finally, construct pESD-B, lacking either ER retention signal, exhibited the same high PE and high FITC signals as seen with construct pESD-A, consistent with a requirement for the ER targeting peptides to maximize substrate cleavage in the ER (FIG. 7B). To verify that signal does not transfer from positive to negative yeast cells, two widely separated cell populations were observed after the mixing of the construct pESD-A containing cells with the construct pESD-E-containing cells (FIG. 7F).

A cell-enrichment study was carried out in order to evaluate the efficiency of the YESS screen (FIG. 2). Based on the model vector, three different plasmids, constructs pESD-F, pESD-G, and pESD-H, were generated (FIG. 16), each containing the TEV-P with its preferred sequence in the peptide 1, peptide 2, or neither position, respectively. Construct pESD-F presented both low PE and FITC signals with its cutting site at peptide 1 position (FIG. 2B); construct pESD-G exhibited high PE but low FITC signals with its cutting site at peptide 2 position (FIG. 2C); and construct pESD-H cuts neither of those two positions, presenting both high PE and FITC signals (FIG. 2D). Cells containing construct pESD-F, pESD-G, and pESD-H were then mixed with a cell ratio of 500:1:500, respectively (FIG. 2E). Sort gates were set to the PE/FITC signal pattern seen with the construct pESD-G. Selected cells were sorted and plated (FIG. 2E). Ten single colonies were selected at random and sequenced. Six of the selected colonies were shown to contain construct pESD-G containing cells, a situation that was confirmed by single colony FACS analysis. Taken together, these results indicate a roughly 600-fold enrichment efficiency after one round of cell sorting.

Figure 1D:
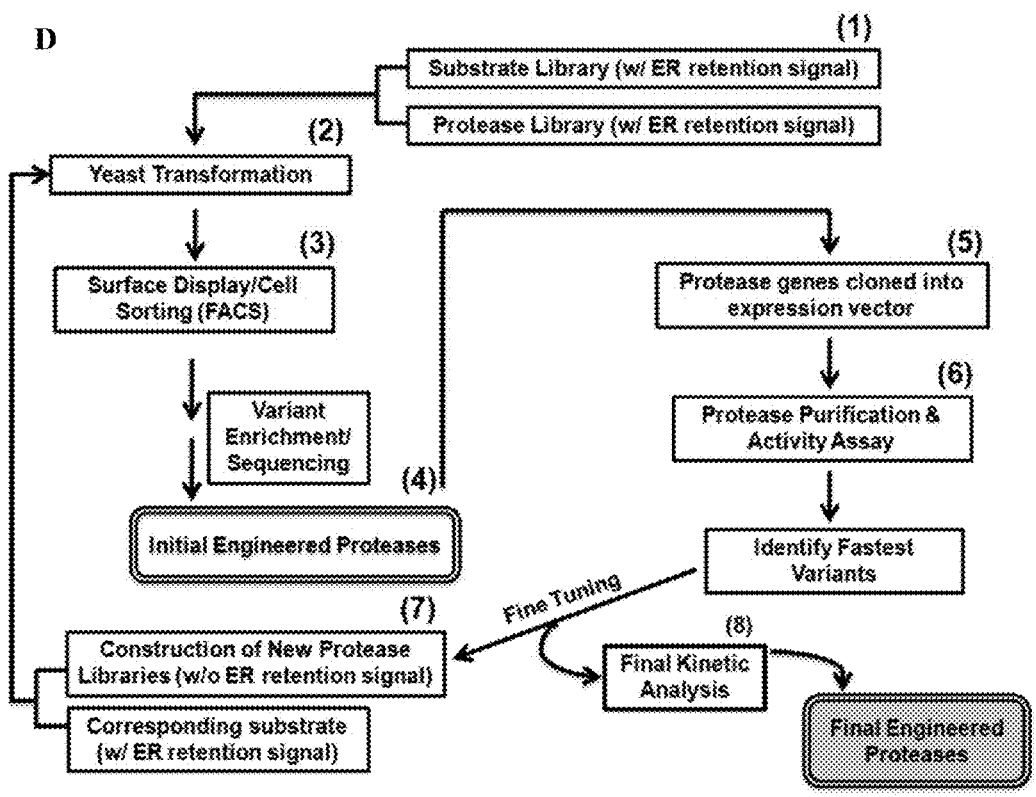
Figure 20:
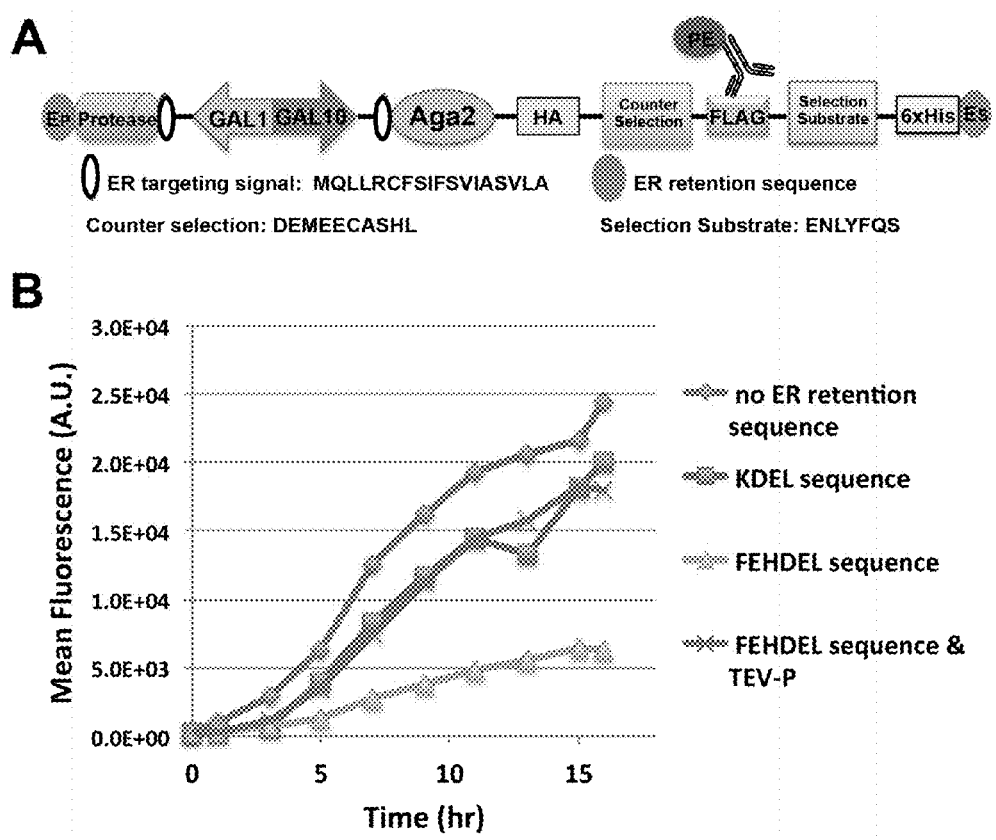
FIGS. 20A-B: ER retention effects in the YESS system.

The ER retention sequence plays an important role in modulating the sensitivity and dynamic range of the YESS system. In time-course experiments, the ER retention sequence, FEHDEL (SEQ ID NO:4), dramatically retains the protein substrate in the yeast ER (FIG. 20). Expression of both the protease and substrate constructs with the ER retention signal retards their release from the ER, thus increasing the time in which they have an opportunity to react. In the absence of the ER retention signal, the contact time as well as the protease concentration is decreased, allowing selection of enzymes that process the substrate construct with higher efficiency in later rounds of directed evolution (FIG. 1D).

Directed Evolution of TEV-P with Altered Substrate Specificity

Figure 21:
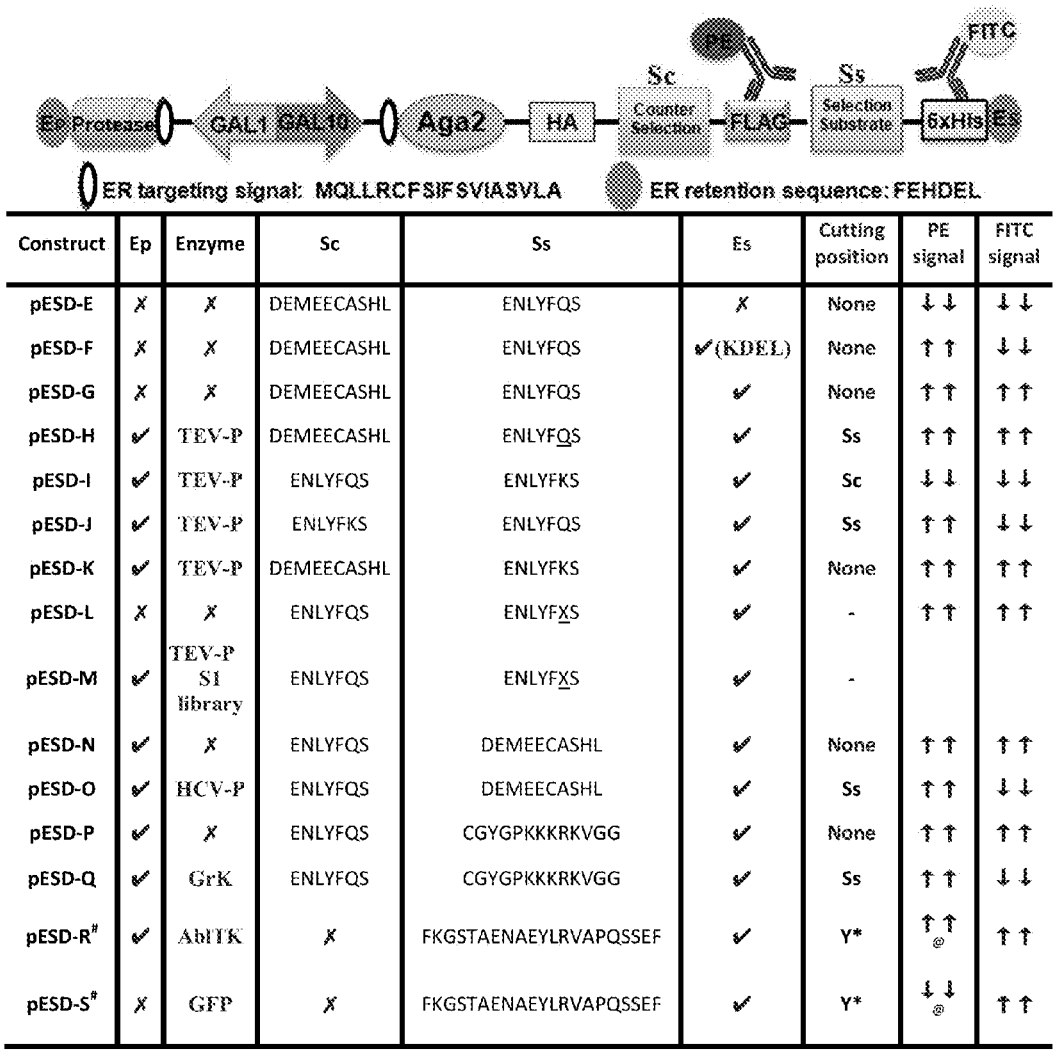
FIG. 21: pESD constructs used in this application. Ep: ER retention sequence at C-terminus of TEV-P (FEHDEL, SEQ ID NO:4); Es: ER retention sequence at C-terminus of substrates (FEHDEL (SEQ ID NO:4) if not otherwise annotated); CGYGPKKKRKVGG: human granzyme K substrate sequence (SEQ ID NO:19); DEMEECASHL: HCV-P substrate sequence (SEQ ID NO:17); ENLYFQS: TEV-P canonical substrate sequence (SEQ ID NO:18); ENLYFKS: mutated TEV-P substrate sequence (SEQ ID NO:11); AblTK: human Abelson tyrosine kinase; #: pESD-R and pESD-S do not contain the fragment of HA-Sc-FLAG in the substrate fusion polypeptide; *: tyrosine phosphorylation; @: fluorescent signal of Alexa Fluor® 647; GFP: green fluorescent protein.

After successful system validation, the inventor's sought to alter the TEV-P substrate specificity at P1 using the YESS system. In an effort to find a new enzyme-substrate combination in an efficient manner, the inventor's adopted the "library-on-library" approach. First, a substrate library randomized at the P1 position (ENLYFXS, X can be any residue, SEQ ID NO:23) was created using specifically randomized oligonucleotides inserted into the peptide 2 position of the construct without a TEV-P (pESD-A, FIG. 7G). As a prelude to library screening, a plasmid (pESD-L, FIG. 21) containing the P1 substrate construct library but lacking the TEV-P protease was constructed. In order to enrich for in-frame library members and simultaneously eliminate stop codons to minimize false positive signals for cleavage during library screening, about $10^7$ substrate library-containing yeast cells were induced with galactose followed by labeling with the anti-6xHis-FITC antibody. The 3% of cells that presented the highest FITC signal intensity were collected using FACS, then their DNA was extracted (FIG. 3A) to be used as the substrate library. In addition, any substrate that is cleaved by an endogenous protease can be eliminated through this step. A TEV-P substrate-binding pocket library was created by randomizing the four 51 pocket residues, T146, D148, H167, and S170, using the NNS codon strategy (N=any nt, S=G/C). The resulting TEV-P S1 pocket library was combined with the P1 substrate library in the pESD construct containing ER retention signals for both protease and substrate (FIG. 2A). Linearized plasmid DNA was cotransformed into yeast with linear DNA encoding the TEV-P S1 saturation library (pESD-M, FIG. 21). Homologous recombination of the substrate construct and TEV-P S1 saturation libraries in *S. cerevisiae* EBY100 cells resulted in $3.3 \times 10^7$ transformants. In this "library-on-library" construct, the counter selection substrate sequence (peptide 1) was the wild-type TEV-P preferred cleavage sequence (ENLYFQS, SEQ ID NO:18) while the P1 substrate library (ENLYFXS, SEQ ID NO:23) was cloned into the peptide 2 position. After galactose induction at 30° C., overnight, the cells were washed and labeled with anti-FLAG-PE and anti-6xHis-FITC antibodies, followed by cell sorting using FACS. After three rounds of enrichment (FIGS. 3B-E; FIGS. 18A-D) for high PE and low FITC signal intensity, the signals were divided into four regions (P1, P2, P3, and P4), which were sorted separately (FIGS. 3F-I). The sorted cells from different regions were plated, and the single colonies were picked, evaluated as single colonies by FACS, and sequenced. A total of 35 different TEV-P variant-substrate combinations were obtained, involving six different substrates (Table 3). The isolated variant-substrate combinations are summarized in Table 2, with the corresponding selected FACS analysis presented in FIG. 8. Sequencing of 50 of the selected clones led to the identification of 35 different TEV-P variant-substrate combinations that contained Pro, Thr, Asn, Leu, Glu, or His at P1 (FIGS. 8, 11, and 12; Table 3). Notably, no TEV-P variant-substrate combinations encoding the wild-type preferred sequence ENLYFQS (SEQ ID NO:18) were isolated, highlighting the utility of the counter selection substrate.

Figure 8:
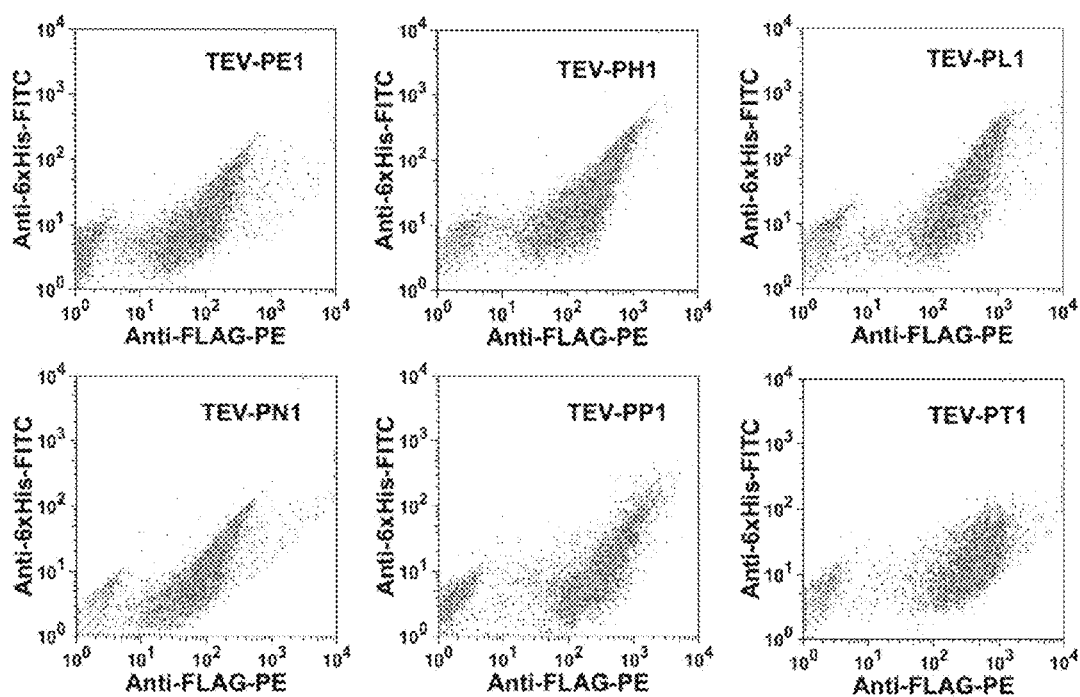
FIG. 8: FACS data of the selected TEV-P variants after the cell sorting of the S1 pocket library. The representative single colonies obtained from the S1 pocket library sorting were sequenced, grown, induced, and analyzed using FACS.
Figure 9:
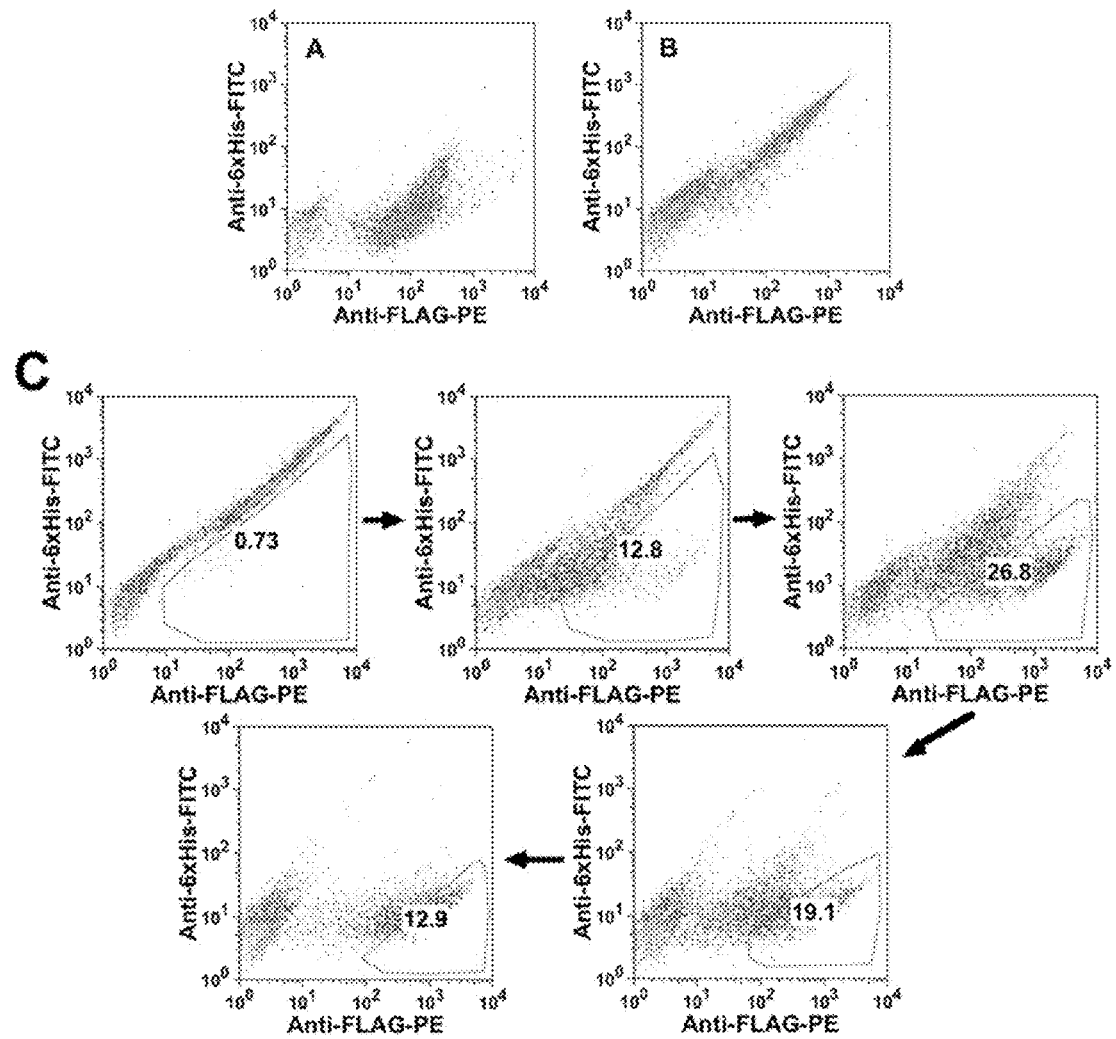
FIGS. 9A-C: FACS data from the TEV protease Variant E error-prone PCR library sorting process. The error-prone PCR library was constructed using the TEV-PE3 as the template, and the cells were sorted as stated in the Methods and Materials.
Figure 10:
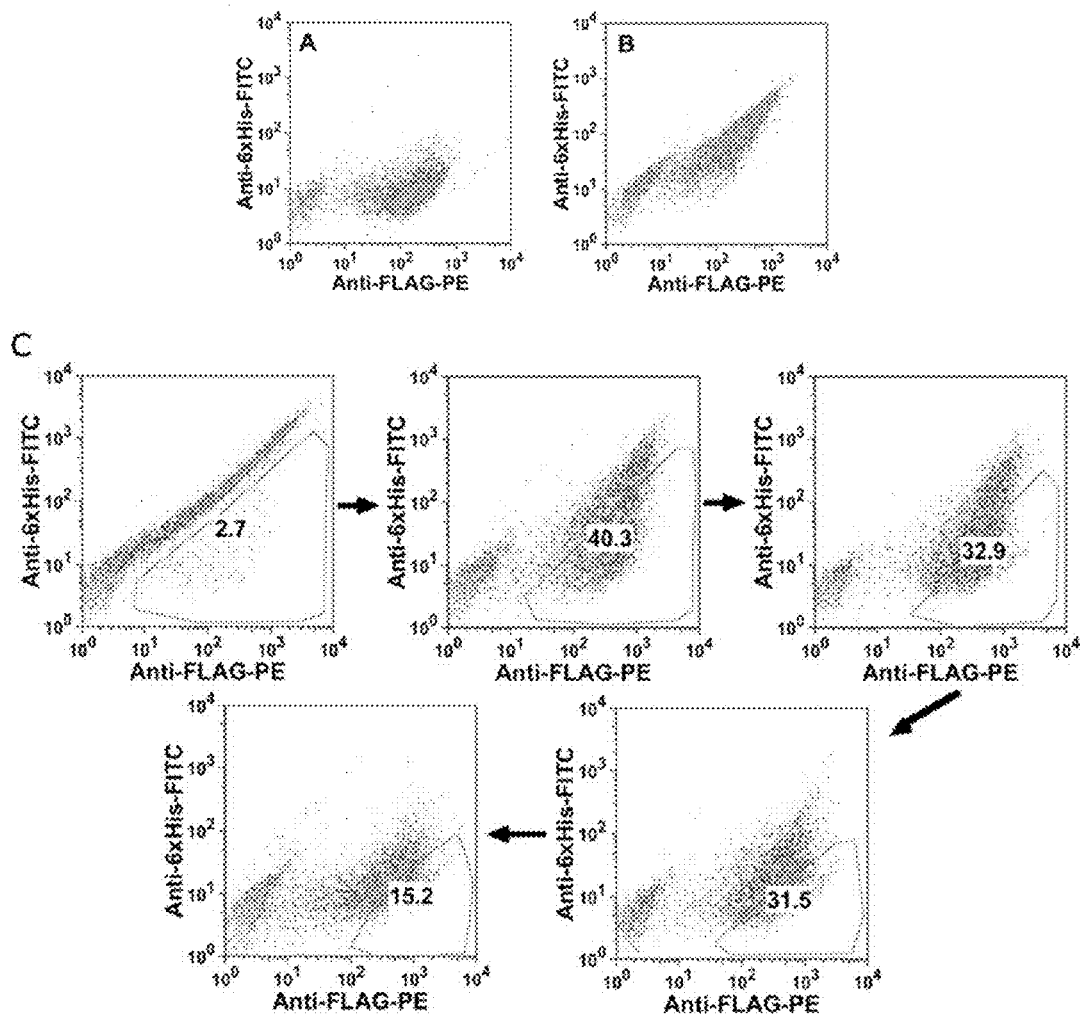
FIGS. 10A-C: FACS data from the TEV protease Variant H error-prone PCR library sorting process. The error-prone library was constructed using the TEV-PH7 as the template, and the cells were sorted as stated in the Methods and Materials.

To obtain the faster and more specific engineered TEV-P variants, second-generation libraries were constructed without ER retention signals using the most promising variants (analogous to the pESD-C construct). The idea is to decrease concentration as well as the amount of time the protease variant incubates with substrate in the ER, increasing stringency of the screen. In particular, the variants with the highest relative PE to FITC signals from the initial sorting experiment (Table 3), TEV-PE3 (P1=E) (FIG. 18E) and TEV-PH7 (P1=H) (FIG. 18F), were chosen as the templates for generating new error-prone PCR libraries. Note that the TEV-PE3 and TEV-PH7 variants were selected in combination with E and H residues, respectively, in the substrate P1 position. In particular, the PE3 and PH7 TEV-P genes were subjected to random mutagenesis by error-prone PCR (1.5%-3.0% error rate). Error-prone PCR libraries of $5 \times 10^7$ (TEV-PE3) and $2 \times 10^7$ (TEV-PH7) members were produced then recombined with their corresponding ENLYFES (SEQ ID NO:1) and ENLYFHS (SEQ ID NO:2) substrates. After five rounds of library sorting (FIGS. 9A-C; FIGS. 10A-C) using FACS, a total of seventeen different variants with relatively high PE-FITC signal ratios were obtained, including fourteen from the TEV-PE3 based error-prone PCR library and three from the TEV-H7 based error-prone PCR library (Table 5). FACS analysis of single clones identified the TEV-PE10 and TEV-PH21 clones as displaying the highest PE vs. FITC fluorescence (FIGS. 8, 11, and 12).

Characterization of Engineered TEV-P Variants

Figure 11:
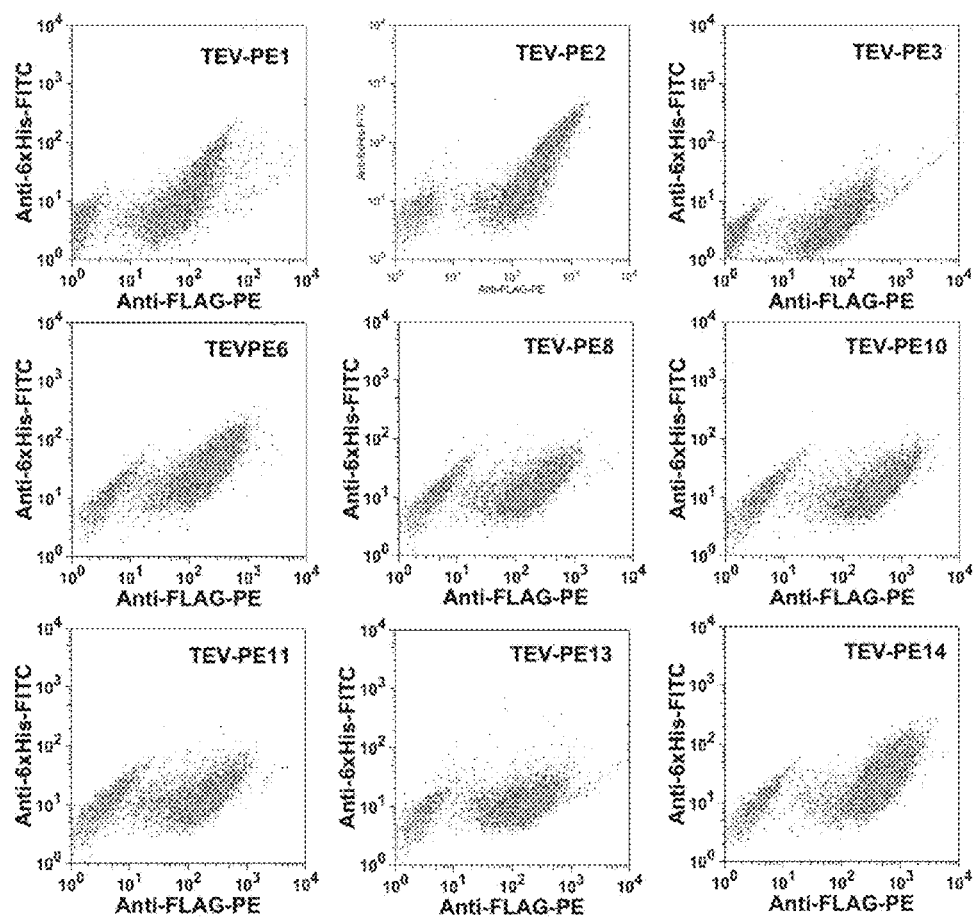
FIG. 11: FACS data of the representative variant E single colonies. The middle row shows the representative single colonies obtained for recognizing the ENLYFES (SEQ ID NO:1) substrate from the sorting of the TEV-PE3 based error-prone PCR library. The ER retention sequence was removed from the C-terminus of the protease in the construct. The variants obtained for recognizing the ENLYFES (SEQ ID NO:1) substrate were grown, induced, and analyzed using FACS.
Figure 12:
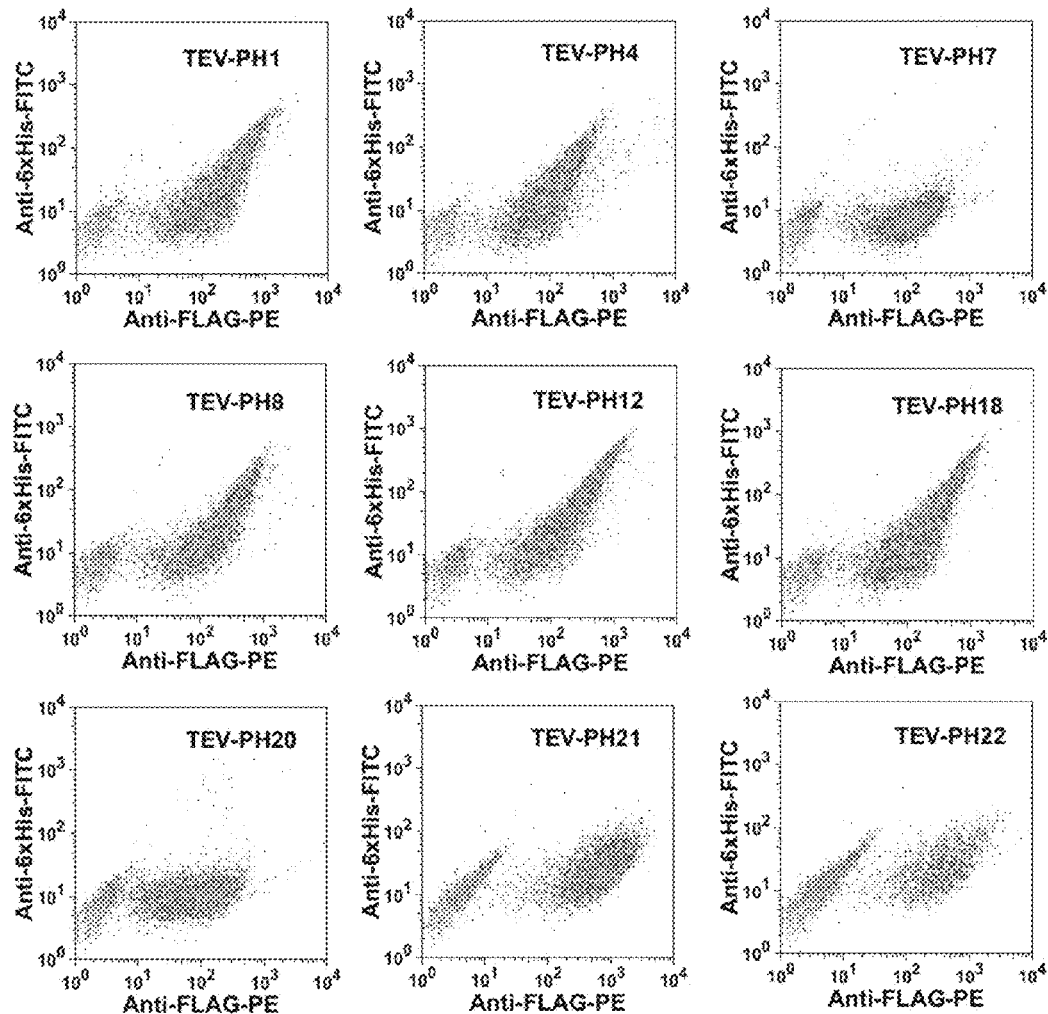
FIG. 12: FACS data of the representative TEV-PH variants. The bottom row shows the representative single colonies obtained for recognizing the ENLYFHS (SEQ ID NO:2) substrate from the sorting of the TEV-PH7 based error-prone PCR library. The ER retention sequence was removed from the C-terminus of the protease in the construct. The variants obtained for recognizing the ENLYFHS (SEQ ID NO:2) substrate were grown, induced, and analyzed using FACS.
Figure 14:
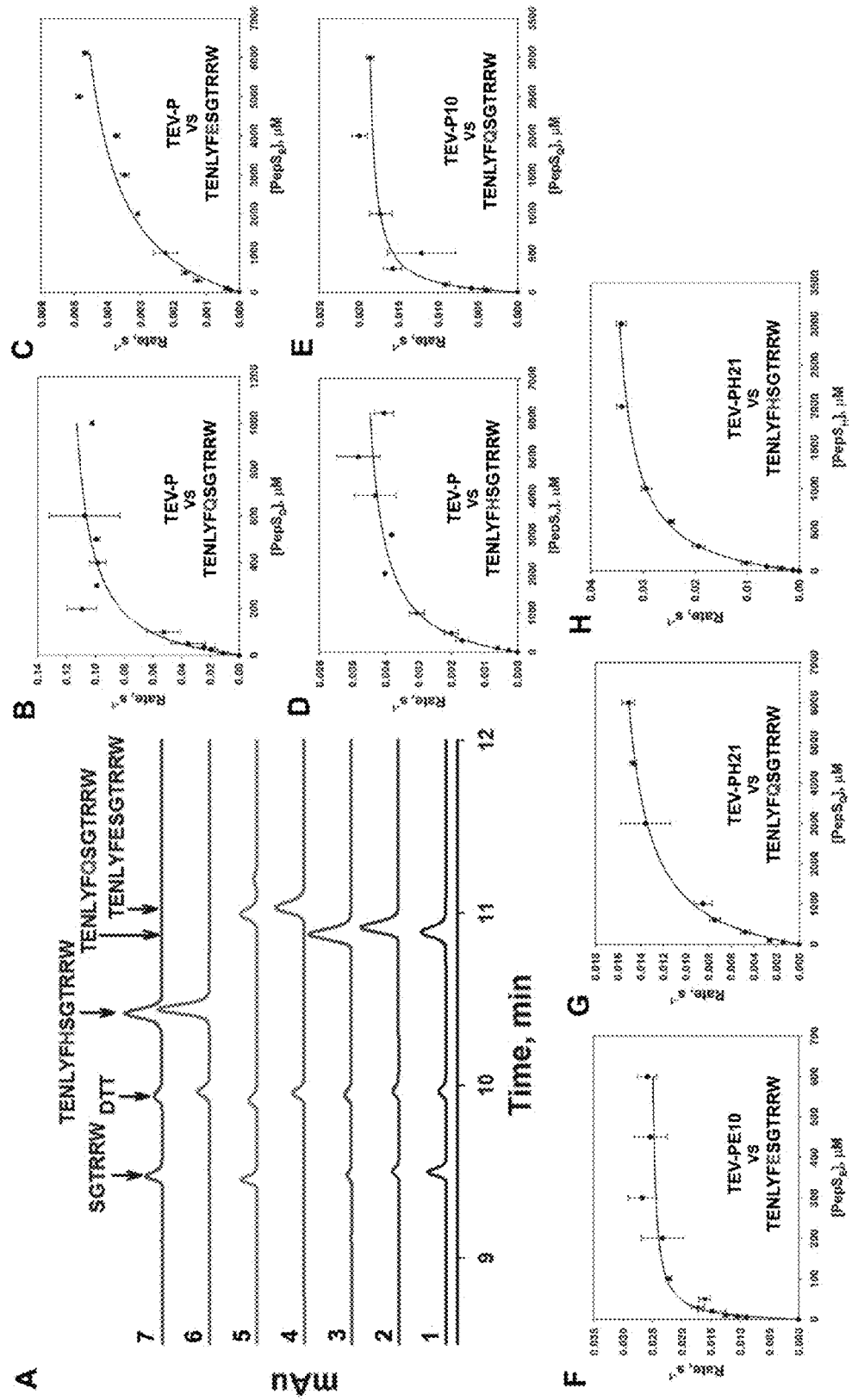
FIGS. 14A-H: The kinetic studies of the TEV-P, TEV-PE10, and TEV-PH21 against different peptide substrates through HPLC analysis. All reactions of purified protease and synthesized peptides were incubated at 30° C. for 1 h with 100 µM peptide substrates. The total reaction volume was 100 µL. The different peptides were eluted at different time points according to the acetonitrile gradients. The data were plotted with the peptide-substrate concentrations against the rates ($s^{-1}$).

After analyzing the sorted single colonies using FACS (FIG. 11; FIG. 12), the TEV-PE10 and TEV-PH21 variants were chosen for further enzymatic characterization because they exhibited the highest PE vs. FITC signals (Table 4). The variant protease genes were cloned into the prk793 expression vector with their corresponding substrate peptides (ENLYES (SEQ ID NO:50) and ENLYFHS (SEQ ID NO:2), respectively) inserted between the MBP and the 6xHis-TEV protease moiety so that the latter could be released by autocatalytic cleavage and purified by Immobilized Metal Ion Affinity Chromatography (IMAC) (FIGS. 13A and B). The MBP fusion partner aids in overall expression and refolding efficiency, but then each construct can auto-process to give TEV containing a 6xHis-tag. Following purification, the TEV-P, TEV-PE10, and TEV-PH21 were incubated with different peptide substrates encoding either Gln, Glu, or His as the P1 substrate residue (FIG. 14A) and their detailed kinetic parameters for the various protease-substrate pairs determined (See Table 7 and FIGS. 14B-H). The $k_{cat}/K_M$ value determined for wild-type TEV-P reacting with its preferred TENLYFQSGTRRW substrate (SEQ ID NO:8) is $1.20\pm0.09$ $mM^{-1}s^{-1}$, which is 375-fold and 150-fold larger than the values determined using TENLYFESGTRRW (SEQ ID NO:10) and TENLYFHSGTRRW (SEQ ID NO:9), respectively. The variant TEV-PE10, on the other hand, exhibited a 13-fold higher $k_{cat}/K_M$ value ($2.06\pm0.46$ $mM^{-1}s^{-1}$) for TENLYFESGTRRW (SEQ ID NO:10) versus TENLYFQSGTRRW (SEQ ID NO:8) ($0.16\pm0.02$ $mM^{-1}s^{-1}$), resulting in a dramatic 5000-fold reversal of substrate specificity compared to TEV-P. Similarly, TEV-PH21 exhibited a seven-fold higher $k_{cat}/K_M$ value for TENLYFHSGTRRW (SEQ ID NO:9) ($0.15\pm0.02$ $mM^{-1}s^{-1}$) versus TENLYFQSGTRRW (SEQ ID NO:8) ($2.07\pm0.13\times10^{-2}$ $mM^{-1}s^{-1}$), an also impressive 1100-fold reversal of substrate specificity compared to TEV-P.

TABLE 7

Michelis-Menten kinetics of the wild-type TEV-P and selected variants with peptide substrates

| Enzyme | Mutations | Substrate | $K_M$ (mM) | $k_{cat}$ (s$^{-1}$) | $k_{cat}/K_M$ (mM$^{-1}$s$^{-1}$) |
|---|---|---|---|---|---|
| TEV-P | none | TENLYFQSGTRRW (SEQ ID NO: 8) | $0.11 \pm 0.02$ | $0.13 \pm 0.01$ | $1.20 \pm 0.09$ |
| TEV-P | | TENLYFESGTRRW (SEQ ID NO: 10) | $1.93 \pm 0.25$ | $6.09 \pm 0.3 \times 10^{-3}$ | $3.14 \pm 0.45 \times 10^{-3}$ |
| TEV-P | | TENLYFHSGTRRW (SEQ ID NO: 9) | $0.64 \pm 0.10$ | $4.93 \pm 0.20 \times 10^{-3}$ | $7.55 \pm 0.68 \times 10^{-3}$ |
| TEV-PE10 | S120R, D148R, | TENLYFQSGTRRW (SEQ ID NO: 8) | $0.12 \pm 0.03$ | $1.94 \pm 0.1 \times 10^{-2}$ | $0.16 \pm 0.02$ |
| TEV-PE10 | T173A, N177K, M218I | TENLYFESGTRRW (SEQ ID NO: 10) | $1.28 \pm 0.18 \times 10^{-2}$ | $2.55 \pm 0.08 \times 10^{-2}$ | $2.06 \pm 0.46$ |
| TEV-PH21 | T17A, T146A, D148P, | TENLYFQSGTRRW (SEQ ID NO: 8) | $0.82 \pm 0.10$ | $1.71 \pm 0.06 \times 10^{-2}$ | $2.07 \pm 0.13 \times 10^{-2}$ |

TABLE 7 -continued

Michelis-Menten kinetics of the wild-type TEV-P and selected variants with peptide substrates

| Enzyme | Mutations | Substrate | $K_M$ (mM) | $k_{cat}$ (s$^{-1}$) | $k_{cat}/K_M$ (mM$^{-1}$s$^{-1}$) |
|---|---|---|---|---|---|
| TEV-PH21 | S153O, S168T, S170A, T173A | TENLYF<u>H</u>SGTRRW (SEQ ID NO: 9) | 0.25 ± 0.02 | 3.75 ± 0.08 × 10$^{-2}$ | 0.15 ± 0.02 |

Figure 4:
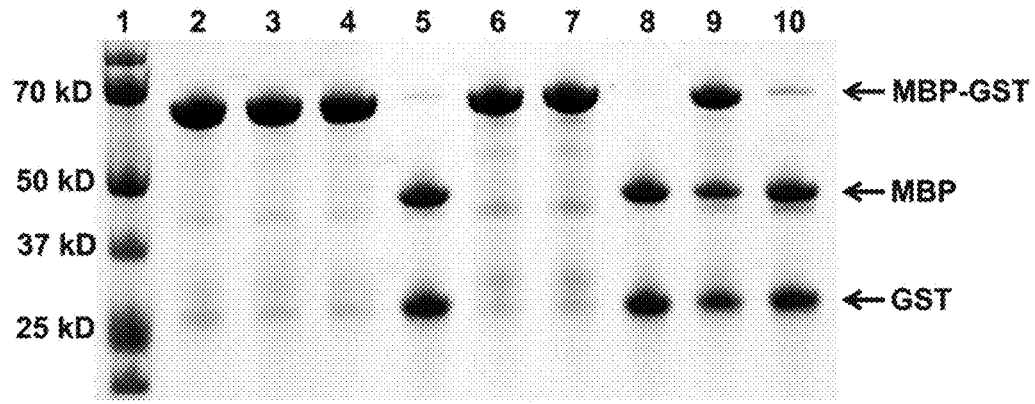
FIG. 4: SDS-PAGE analysis showing digestion of protein fusion substrates by TEV-P and its engineered variants. Reactions were incubated at 30° C., pH 8.0, for 1 h with 5 μg protein substrate mixed with or without 0.1 μg protease in 20 μL reaction buffer. Lane 1, molecular mass ladders; Lane 2, the $ProS_Q$ (MBP-ENLYFQS-GST, MBP-SEQ ID NO:18-GST) substrate only; Lane 3, the $ProS_E$ (MBP-ENLYFES-GST, MBP-SEQ ID NO:1-GST) substrate only; Lane 4, the $ProS_H$ (MBP-ENLYFHS-GST, MBP-SEQ ID NO:2-GST) substrate only; Lane 5, the $ProS_Q$ substrate incubated with the TEV-P; Lane 6, the $ProS_E$ substrate incubated with the TEV-P; Lane 7, the $ProS_H$ substrate incubated with the TEV-P; Lane 8, the $ProS_E$ substrate incubated with the TEV-PE10; Lane 9, the $ProS_H$ substrate incubated with the TEV-PH21; Lane 10, the $ProS_H$ substrate incubated with the TEV-PH21 for 3 h.

To assess the activities of the TEV-P, TEV-PE10, and TEV-PH21 variants with protein (as opposed to peptide) substrates, three different MBP-GST fusion protein substrates were created containing the sequences ENLYFQS (MBP-ENLYFQS-GST) (MBP-SEQ ID NO:18-GST), ENLYFES (MBP-ENLYFES-GST) (MBP-SEQ ID NO:1-GST), and ENLYFHS (MBP-ENLYFHS-GST) (MBP-SEQ ID NO:2-GST), respectively, within a linker inserted between the MBP and GST units (FIGS. 13A-B). Using TEV-P under conditions that lead to 95% cleavage of the MBP-ENLYFQS-GST (MBP-SEQ ID NO: 18-GST) fusion construct, approximately 3% cleavage was seen with either the MBP-ENLYF<u>E</u>S-GST (MBP-SEQ ID NO:1-GST) or MBP-ENLYF<u>H</u>S-GST (MBP-SEQ ID NO:2-GST) fusion protein substrates (FIG. 4). In contrast, the TEV-PE10 caused more than 99% cleavage of the MBP-ENLYFES-GST (MBP-SEQ ID NO:1-GST) construct and TEV-PH21 gave close to 50% cleavage of the MBP-ENLYF<u>H</u>S-GST (MBP-SEQ ID NO:2-GST) construct under these conditions. Importantly, in the latter case, longer incubation lead to complete cleavage. The protein substrates were also used to evaluate pH dependent cleavage in the range of 6.5 to 8.0. The TEV-PE10 and TEV-PH21 variants exhibited a pH dependence that is qualitatively similar to TEV-P, exhibiting the highest activity at pH 8.0 and slightly decreased activity at pH 7.2 and pH 6.5 (FIGS. 15A-C).

Using Other Proteases and Kinases with the MESS System

To assess the generality of the YESS system for other proteases, analogous constructs were created in which the hepatitis C protease (HCV-P) and the human granzyme K protease (GrK) were used in conjunction with their preferred substrate sequences, respectively. As seen in FIGS. 19A and B, yeast cells expressing the HCV-P and GrK proteases with their preferred substrates displayed relatively similar PE but low FITC signals by FACS compared to the controls lacking proteases. Furthermore, the YESS system is not only limited to protease engineering. Our preliminary experiments of using the YESS system for the human AblTK indicated that kinases might also be engineered through the YESS system (FIG. 19C). Yeast cells expressing the human AblTK with their preferred substrates displayed relatively similar FITC but high Alexa Fluor@647 signals by FACS compared to the controls lacking proteases, indicating complete tyrosine phosphorylation by human AblTK of its substrate in the YESS system. These results, identical to that seen with the analogous TEV-P construct, confirm that many other proteases and kinases will be compatible with the YESS approach.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,826,364
U.S. Pat. No. 4,284,412
U.S. Pat. No. 4,498,766
U.S. Pat. No. 4,554,101
U.S. Pat. No. 4,661,913
U.S. Pat. No. 4,714,682
U.S. Pat. No. 4,767,206
U.S. Pat. No. 4,774,189
U.S. Pat. No. 4,857,451
U.S. Pat. No. 4,897,268
U.S. Pat. No. 4,989,977
U.S. Pat. No. 5,075,109
U.S. Pat. No. 5,160,974
U.S. Pat. No. 5,478,722
U.S. Pat. No. 5,552,157
U.S. Pat. No. 5,565,213
U.S. Pat. No. 5,567,434
U.S. Pat. No. 5,738,868
U.S. Pat. No. 5,795,587
Aharoni et al., *Chem. Biol.*, 12(12):1281-1289, 2005.
Arber et al., *J. Cell Biol.*, 116:113-125, 1992.
Benatuil et al., *Protein Eng. Des. Sel.*, 23(4):155-159, 2010.
Boder and Wittrup, *Nat. Biotechnol.*, 15(6):553-557, 1997.
Chanalia et al., *Rev. Med. Microbiol.*, 22(4):6, 2011.
Chao et al., *Nat. Protoc.*, 1(2):755-768, 2006.
Chen et al., *Proc. Natl. Acad. Sci. USA*, 108(28):11399-11404, 2011.
Cohen and Lijnen, *Blood*, 78(12):3114-3124, 1991.
Copic et al., *Genetics*, 182:757-769, 2009.
Craik et al., *Biochem. J.*, 435(1):1-16, 2011.
Denecke et al., *EMBO J.*, 11(6):2345-2355, 1992.
Dougherty and Parks, *Virology*, 172145, 1989.
Dougherty et al., *Embo J.*, 7(5):1281-1287, 1988.
Dougherty et al., *Virology*, 172:302, 1989.
Drag and Salvesen, *Nat. Rev. Drug Discov.*, 9:690-701, 2010.
Drummond et al., *J. Mol. Biol.*, 350(4):806-816, 2005.
Gai et al., *Curr. Opin. Struct. Biol.*, 17:467-473, 2007.
Gera et al., *Methods*, 2012 (Epub ahead of print))
Gould and Tawfik, *Biochemistry*, 44(14):5444-5452, 2005.
Gray et al., *Cell*, 142(4):637-646, 2010.
Gupta et al., *Appl. Microbiol. Biotechnol.*, 59(1):15-32, 2002.

Han et al., *Appl. Environ. Microbiol.*, 78(9):3249, 2012/Hedstrom et al., *Science*, 255(5049):1249-1253, 1992.
Hedstrom, *Chem. Rev.*, 102(12):4501-4524, 2002.
Hegde and Keenan, *Nat Rev Mol Cell Biol.*, 12(12):787-98, 2011.
Huang et al., *Genetics*, 182(1):173-89, 2009.
Jung et al., *Proc. Natl. Acad. Sci. U.S.A.*, 107:604-609, 2010.
Kapust et al., *Biochem. Biophys. Res. Commun.*, 294:949-955, 2002a.
Kim et al., *Anal. Biochem.*, 284(1):42-48, 2000.
Kim et al., *Appl Microbiol Biotechnol.*, 88(4):893-903, 2010.
Kyte and Doolittle, *J. Mol. Biol.*, 157(1):105-132, 1982.
Lee et al., *Bioresource Tech.*, 102:9179-9184, 2011.
Lim et al., *J. Biol. Chem.*, 282(13):9722-9732, 2007.
Lin et al., *J. Immunol. Methods*, 375:159-165, 2012
Marnett and Craik, *Trends Biotechnol.*, 23(2):59-64, 2005.
Mohanty et al., *Protein Expr. Purif.*, 27:109-114, 2003.
Monnat et al., *Molec. Biol. Cell*, 11:3469-3484, 2000.
Nallamsrtty et al., *Protein Expr. Purif.*, 38(1):108-15, 2004.
O'Loughlin et al., *Mol. Biol. Evol.*, 23(4):764-772, 2006.
Overall and Blobel, *Nat. Rev. Mol. Cell. Biol.*, 8(3):245-257, 2007.
Park and Rapoport, *Annu Rev Biophys.*, 41:21-40, 2012.
PCT Appln. WO 2008/137475.
Pelham et al., *Embo J.*, 7(6):1757-1762, 1988.
Phan et al., *J. Biol. Chem.*, 277(52):50564-50572, 2002.
Ramachandran et al., *Nat. Rev. Drug Discov.*, 11(1):69-86, 2012.
Rapoport, *Nature*, 450(7170):663-9, 2007.
Remington: The Science and Practice of Pharmacy, 21$^{st}$ Ed. Lippincott Williams and Wilkins, 2005.
Remington: The Science and Practice of Pharmacy, 21$^{st}$ Ed., Pharmaceutical Press, 2011.
Schechter and Berger, A *Biochem. Biophys. Res. Commun.*, 27(2):157-162, 1967.
Schilling and Overall, *Nat. Biotechnol.*, 26(6):685-694, 2008.
Sellamuthu et al., *Biochem. Biophys. Res. Commun.*, 371(1): 122-126, 2008.
Sellamuthu et al., *PLoS One*, 6(7):e22554, 2011.
Semenza et al., *Cell*, 61(7):1349-1357, 1990.
Small et al., *Proteomics*, 4(6):1581-90, 2004.
Teasdale and Jackson, *Cell Dev. Biol.* 12, 27-54, 1996.
Tropea et al., *Methods Mol. Biol.*, 498:297-307, 2009.
Varadarajan et al., *Angew. Chem. Int. Ed. Engl.*, 47(41):7861-7863, 2008.
Varadarajan et al., *J. Am. Chem. Soc.*, 131(50):18186-18190, 2009a.
Varadarajan et al., *Nat. Chem. Biol.*, 4(5):290-294, 2008.
Varadarajan et al., *Nat. Protoc.*, 4(6):893-901, 2009b.
Varadarajan et al., *Proc. Natl. Acad. Sci. USA*, 102(19):6855-6860, 2005.
Villa et al., *J. Biol. Chem.*, 278(43):42545-42550, 2003.
Waugh, *Protein Expr. Purif.*, 80:283-293, 2011.
Wehr et al., *Nat. Methods*, 3:985-993, 2006.

What is claimed is:

1. A nucleic acid vector for engineering protease variants, wherein the nucleic acid vector encodes two separately expressed fusion proteins, wherein the first fusion protein comprise, in an N- to C-terminal direction:
   (i) a first endoplasmic reticulum (ER) targeting sequence;
   (ii) a surface expression sequence;
   (iii) a first peptide sequence that is a counterselection substrate sequence for the enzyme of the second fusion protein;
   (iv) a first epitope tag sequence;
   (v) a second peptide sequence that is a selection substrate sequence for the enzyme of the second fusion protein;
   (vi) a second epitope tag sequence; and
   (vii) a first endoplasmic reticulum (ER) retention sequence,
   wherein the second fusion protein comprises, in an N- to C-terminal direction:
   (viii) a second endoplasmic reticulum (ER) targeting sequence;
   (ix) an enzyme, wherein the enzyme is a protease; and
   (x) a second endoplasmic reticulum (ER) retention sequence.

2. The nucleic acid of claim 1, wherein the nucleic acid encoding the first fusion protein is operably linked to a first promoter; and wherein the nucleic acid encoding the second fusion protein is operably linked to a second promoter.

3. The nucleic acid of claim 2, wherein the first promoter and the second promoter are expressable in yeast.

4. The nucleic acid of claim 2, wherein the first promoter is Gal1 or Gal10.

5. The nucleic acid of claim 2, wherein the second promoter is Gal1 or Gal10.

6. The nucleic acid of claim 2, wherein the nucleic acid comprises one or more enhancers.

7. The nucleic acid of claim 1, wherein at least a portion of the first peptide is randomized.

8. The nucleic acid of claim 1, wherein the first peptide is a sequence that is unrelated to the native substrate or shares no or essentially no sequence identity with the native substrate of the protease.

9. The nucleic acid of claim 1, wherein the first peptide is a mutated native substrate of the protease.

10. The nucleic acid of claim 9, wherein the first peptide has 1, 2, 3, 4, or 5 mutations, additions, or deletions as compared to the native substrate of the protease.

11. The nucleic acid of claim 1, wherein at least a portion of the second peptide is randomized.

12. The nucleic acid of claim 1, wherein the second peptide is the native substrate of the protease.

13. The nucleic acid of claim 1, wherein the protease is a human protease.

14. The nucleic acid of claim 13 wherein the protease is a TEV-protease, rTPA, a coagulation factor, factor 7, factor 9, human trypsin, a granzyme, a caspase, trypsin, human granzyme K, or a human caspase.

15. The nucleic acid of claim 1, wherein at least a portion of the protease is randomized.

16. The nucleic acid of claim 1, wherein the protease has 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, additions, or deletions as compared to the wild-type protease.

17. The nucleic acid of claim 1, wherein the first endoplasmic reticulum (ER) targeting sequence and the second endoplasmic reticulum (ER) targeting sequence are MQLLRCFSIFSVIASVLA (SEQ ID NO:3).

18. The nucleic acid of claim 1, wherein the first endoplasmic reticulum (ER) retention sequence and the second endoplasmic reticulum (ER) retention sequence are FEHDEL (SEQ ID NO:4), KDEL (SEQ ID NO:5), HDEL (SEQ ID NO:6), or RDEL (SEQ ID NO:7).

19. The nucleic acid of claim 1, wherein the nucleic acid further encodes a third epitope tag sequence.

20. The nucleic acid of claim 19, wherein the third epitope tag sequence is a hemagglutinin epitope tag.

21. The nucleic acid of claim 19, wherein the third epitope tag is comprised in the first fusion construct.

22. The nucleic acid of claim 19, wherein the third epitope tag is located between (ii) and (iii).

23. A cell comprising the nucleic acid vector of claim 1.

24. The cell of claim 23, wherein the cell is a yeast cell.

25. A method for producing a protease, comprising:
   (i) expressing one or more nucleic acid of claim 1 in a plurality of cells;
   (ii) purifying or separating cells based on the presence or absence of an antibody that selectively binds the first epitope tag sequence or the second epitope tag sequence, and
   (iii) isolating or purifying the protease.

26. The method of claim 25, wherein the cell is a yeast cell.

27. The method of claim 25, wherein the nucleic acid further encodes a third epitope tag.

28. The method of claim 27, further comprising purifying cells that express the third epitope tag.

29. The method of claim 25, wherein the antibody is labeled with a fluorophore.

30. The method of claim 25, wherein the isolating or purifying the protease comprises FACS.

31. The method of claim 25, further comprising isolating the nucleic acid.

32. The method of claim 31, further comprising further randomizing a portion of the nucleic acid.

33. The method of claim 25, further comprising further characterizing the protease encoded by the nucleic acid.

34. The method of claim 33, further comprising repeating steps (i) and (ii).

35. A nucleic acid vector for engineering protease and substrate variants, wherein the nucleic acid vector encodes two separately expressed fusion proteins, wherein the first fusion protein comprises, in an N- to C-terminal direction:
   (i) a first endoplasmic reticulum (ER) targeting sequence;
   (ii) a surface expression sequence;
   (iii) a first epitope tag sequence;
   (iv) a first peptide sequence that is a selection substrate sequence for the enzyme of the second fusion protein;
   (v) a second epitope tag sequence;
   (vi) a second peptide sequence that is a counterselection substrate sequence for the enzyme of the second fusion protein;
   (vii) a third epitope tag sequence; and
   (viii) a first endoplasmic reticulum (ER) retention sequence, wherein the second fusion protein comprises, in an N- to C-terminal direction:
   (ix) a second endoplasmic reticulum (ER) targeting sequence;
   (x) an enzyme, wherein the enzyme is a protease; and
   (xi) a second endoplasmic reticulum (ER) retention sequence.

36. The nucleic acid of claim 35, wherein the nucleic acid encoding the first fusion protein is operably linked to a first promoter; and wherein the nucleic acid encoding the second fusion protein is operably linked to a second promoter.

37. The nucleic acid of claim 36, wherein the first promoter and the second promoter are expressable in yeast.

38. The nucleic acid of claim 36, wherein the first promoter is Gal1 or Gal10.

39. The nucleic acid of claim 36, wherein the second promoter is Gal1 or Gal10.

40. The nucleic acid of claim 36, wherein the nucleic acid comprises one or more enhancers.

41. The nucleic acid of claim 35, wherein at least a portion of the first peptide is randomized.

42. The nucleic acid of claim 35, wherein the first peptide is the native substrate of the protease.

43. The nucleic acid of claim 35, wherein at least a portion of the second peptide is randomized.

44. The nucleic acid of claim 35, wherein the second peptide is a sequence that is unrelated to the native substrate or shares no or essentially no sequence identity with the native substrate of the protease.

45. The nucleic acid of claim 35, wherein the second peptide is a mutated native substrate of the protease.

46. The nucleic acid of claim 35, wherein the second peptide has 1, 2, 3, 4, or 5 mutations, additions, or deletions as compared to the native substrate of the protease.

47. The nucleic acid of claim 35, wherein the protease is a human protease.

48. The nucleic acid of claim 47 wherein the protease is a TEV-protease, rTPA, a coagulation factor, factor 7, factor 9, human trypsin, a granzyme, a caspase, trypsin, human granzyme K, or a human caspase.

49. The nucleic acid of claim 35, wherein at least a portion of the protease is randomized.

50. The nucleic acid of claim 35, wherein the protease has 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations, additions, or deletions as compared to the wild-type protease.

51. The nucleic acid of claim 35, wherein the first endoplasmic reticulum (ER) targeting sequence and the second endoplasmic reticulum (ER) targeting sequence are MQLLRCFSIFSVIASVLA (SEQ ID NO:3).

52. The nucleic acid of claim 35, wherein the first endoplasmic reticulum (ER) retention sequence and the second endoplasmic reticulum (ER) retention sequence are FEHDEL (SEQ ID NO:4), KDEL (SEQ ID NO:5), HDEL (SEQ ID NO:6), or RDEL (SEQ ID NO:7).

53. The nucleic acid of claim 35, wherein the third epitope tag sequence is a hemagglutinin epitope tag.

54. A cell comprising the nucleic acid vector of claim 35.

55. The cell of claim 54, wherein the cell is a yeast cell.

56. A method for producing a protease, comprising:
   (i) expressing one or more nucleic acid of claim 35 in a plurality of cells;
   (ii) purifying or separating cells based on the presence or absence of an antibody that selectively binds the first epitope tag sequence or the second epitope tag sequence, and
   (iii) isolating or purifying the protease.

57. The method of claim 56, wherein the cell is a yeast cell.

58. The method of claim 56, wherein the antibody is labeled with a fluorophore.

59. The method of claim 56, wherein the isolating or purifying the protease comprises FACS.

60. The method of claim 56, further comprising isolating the nucleic acid.

61. The method of claim 60, further comprising further randomizing a portion of the nucleic acid.

62. The method of claim 56, further comprising further characterizing the protease encoded by the nucleic acid.

63. The method of claim 62, further comprising repeating steps (i) and (ii).

64. A nucleic acid vector for engineering kinase variants, wherein the nucleic acid vector encodes two separately expressed fusion proteins, wherein the first fusion protein comprises, in an N- to C-terminal direction:
  (i) a first endoplasmic reticulum (ER) targeting sequence;
  (ii) a surface expression sequence;
  (ii) an epitope tag sequence and a peptide sequence that is a selection substrate sequence for the enzyme of the second fusion protein; and
  (iii) a first endoplasmic reticulum (ER) retention sequence, wherein the second fusion protein comprises, in an N- to C-terminal direction:
    (iv) a second endoplasmic reticulum (ER) targeting sequence;
    (ix) an enzyme, wherein the enzyme is a protein kinase; and
    (x) a second endoplasmic reticulum (ER) retention sequence.

65. The nucleic acid of claim 64, wherein the nucleic acid encoding the first fusion protein is operably linked to a first promoter; and wherein the nucleic acid encoding the second fusion protein is operably linked to a second promoter.

66. The nucleic acid of claim 65, wherein the first promoter and the second promoter are expressable in yeast.

67. The nucleic acid of claim 65, wherein the first promoter is Gal1 or Gal10.

68. The nucleic acid of claim 65, wherein the second promoter is Gal1 or Gal10.

69. The nucleic acid of claim 65, wherein the nucleic acid comprises one or more enhancers.

70. The nucleic acid of claim 64, wherein at least a portion of the peptide sequence is randomized.

71. The nucleic acid of claim 64, wherein the peptide sequence is the native substrate of the kinase.

72. The nucleic acid of claim 64, wherein the kinase is a tyrosine kinase, an AGC kinase, a CAMK (CaM kinase), a CMGC kinase, a CK1 kinase, a STE kinase, or a TKL kinase, or a thymidine kinase (TK kinase).

73. The nucleic acid of claim 64, wherein the first endoplasmic reticulum (ER) targeting sequence and the second endoplasmic reticulum (ER) targeting sequence are MQLL-RCFSIFSVIASVLA (SEQ ID NO:3).

74. The nucleic acid of claim 64, wherein the first endoplasmic reticulum (ER) retention sequence and the second endoplasmic reticulum (ER) retention sequence are FEHDEL (SEQ ID NO:4), KDEL (SEQ ID NO:5), HDEL (SEQ ID NO:6), or RDEL (SEQ ID NO:7).

75. A cell comprising the nucleic acid vector of claim 64.

76. The cell of claim 75, wherein the cell is a yeast cell.

77. A method for producing a kinase, comprising:
  (i) expressing one or more nucleic acid of claim 64 in a plurality of cells;
  (ii) purifying or separating cells based on the presence or absence of an antibody that selectively binds the first epitope tag sequence or the second epitope tag sequence, and
  (iii) isolating or purifying the kinase.

78. The method of claim 77, wherein the cell is a yeast cell.

79. The method of claim 77, wherein the antibody is labeled with a fluorophore.

80. The method of claim 77, wherein the isolating or purifying the kinase comprises FACS.

81. The method of claim 77, further comprising isolating the nucleic acid.

82. The method of claim 81, further comprising further randomizing a portion of the nucleic acid.

83. The method of claim 77, further comprising further characterizing the kinase encoded by the nucleic acid.

84. The method of claim 83, further comprising repeating steps (i) and (ii).

\* \* \* \* \*

UNITED STATES PATENT AND TRADEMARK OFFICE
CERTIFICATE OF CORRECTION

| | | |
|---|---|---|
| PATENT NO. | : 8,945,855 B2 | Page 1 of 1 |
| APPLICATION NO. | : 13/926749 | |
| DATED | : February 3, 2015 | |
| INVENTOR(S) | : Iverson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 25 days.

Signed and Sealed this
Thirteenth Day of October, 2015

Michelle K. Lee
*Director of the United States Patent and Trademark Office*